US012351654B2

(12) United States Patent
Trapp et al.

(10) Patent No.: US 12,351,654 B2
(45) Date of Patent: Jul. 8, 2025

(54) POLYMERS, ARTICLES, AND CHEMICALS MADE FROM HIGH CONCENTRATED RECYCLE DERIVED SYNGAS

(71) Applicant: Eastman Chemical Company, Kingsport, TN (US)

(72) Inventors: William Lewis Trapp, Kingsport, TN (US); Justin William Murphy, Kingsport, TN (US); Nathan Mitchell West, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 681 days.

(21) Appl. No.: 17/593,861

(22) PCT Filed: Mar. 26, 2020

(86) PCT No.: PCT/US2020/024891
§ 371 (c)(1),
(2) Date: Sep. 27, 2021

(87) PCT Pub. No.: WO2020/205415
PCT Pub. Date: Oct. 8, 2020

(65) Prior Publication Data
US 2022/0162344 A1    May 26, 2022

Related U.S. Application Data

(60) Provisional application No. 62/906,823, filed on Sep. 27, 2019, provisional application No. 62/825,858, filed on Mar. 29, 2019.

(51) Int. Cl.
*C08B 3/06* (2006.01)
*C01B 3/36* (2006.01)
*C07C 29/151* (2006.01)
*C07C 51/09* (2006.01)
*C07C 51/12* (2006.01)
*C07C 67/08* (2006.01)
*C08L 1/12* (2006.01)
*C08L 1/14* (2006.01)
*C10J 3/46* (2006.01)
*C10J 3/78* (2006.01)
*D01F 2/28* (2006.01)

(52) U.S. Cl.
CPC ............... *C08B 3/06* (2013.01); *C01B 3/36* (2013.01); *C07C 29/1518* (2013.01); *C07C 51/09* (2013.01); *C07C 51/12* (2013.01); *C07C 67/08* (2013.01); *C08L 1/12* (2013.01); *C08L 1/14* (2013.01); *C10J 3/466* (2013.01); *C10J 3/78* (2013.01); *D01F 2/28* (2013.01); C01B 2203/025 (2013.01); C01B 2203/061 (2013.01); C08L 2201/06 (2013.01); C08L 2203/12 (2013.01); C08L 2207/20 (2013.01); C10J 2300/093 (2013.01); *C10J 2300/0946* (2013.01); *C10J 2300/1656* (2013.01); *C10J 2300/1665* (2013.01)

(58) Field of Classification Search
None
See application file for complete search history.

(56) References Cited

U.S. PATENT DOCUMENTS

| 3,817,725 | A  | 6/1974  | Sieg et al. |
| 3,841,851 | A  | 10/1974 | Kaiser |
| 3,909,364 | A  | 9/1975  | Singh |
| 4,052,173 | A  | 10/1977 | Schulz |
| 4,152,119 | A  | 5/1979  | Schulz |
| 4,225,457 | A  | 9/1980  | Schulz |
| 4,886,000 | A  | 12/1989 | Hölter et al. |
| 5,323,714 | A  | 6/1994  | Cox |
| 5,656,042 | A  | 8/1997  | Khan et al. |
| 5,821,111 | A  | 10/1998 | Grady et al. |
| 5,922,090 | A  | 7/1999  | Fujimura et al. |
| 5,984,985 | A  | 11/1999 | Malone |
| 6,063,355 | A  | 5/2000  | Fujimura et al. |
| 6,321,666 | B1 | 11/2001 | Tigonen |
| 6,401,635 | B1 | 6/2002  | Nieminen et al. |
| 6,439,135 | B1 | 8/2002  | Pope |
| 7,425,315 | B2 | 9/2008  | Kruesi |
| 7,500,997 | B2 | 3/2009  | Norbeck et al. |

(Continued)

FOREIGN PATENT DOCUMENTS

| CA | 2 937 445 A1 | 1/2018 |
| CN | 1102605 C    | 3/2003 |

(Continued)

OTHER PUBLICATIONS

Co-pending U.S. Appl. No. 17/310,649, filed Aug. 16, 2021; Trapp et al.
Co-pending U.S. Appl. No. 17/310,661 filed Aug. 16, 2021; Trapp et al.
Co-pending U.S. Appl. No. 17/593,628, filed Sep. 22, 2021; Trapp et al.
Agrawal; "Compositional Analysis of Solid Waste and Refuse Derived Fuels by Thermogravimetry;" Compositional Analysis by Thermogravimetry; ASTM STP 997; C.M. Earnest, Ed .; American Society for Testing and Materials; Philadelphia; 1988; pp. 259-271.
Alter; "The Origins of Municipal Solid Waste: The Relations Between Residues from Packaging Materials and Food;" Waste Management & Research; 7; 1989; pp. 103-114.

(Continued)

*Primary Examiner* — Layla D Berry
(74) *Attorney, Agent, or Firm* — Robert C. Morriss

(57) ABSTRACT

High concentrations of recycle polymer are gasified in a partial oxidation gasifier to make a syngas useful to make a variety of chemicals and polymers, such as cellulose ester. Polymers such as cellulose esters can be made that are obtained from sustainable sources, recycle sources, and are biodegradable. Circularity in the manufacture of textiles and/or plastics made from the fibers of such cellulose esters can now be achieved. The process of making such a syngas from high concentrations of recycle polymer (e.g. textiles and/or plastics) includes campaigning for the production of syngas.

20 Claims, No Drawings

(56) References Cited

U.S. PATENT DOCUMENTS

| | | |
|---|---|---|
| 8,083,818 B2 | 12/2011 | Ploeg et al. |
| 8,118,894 B2 | 2/2012 | Norbeck et al. |
| 8,202,913 B2 | 6/2012 | Robinson et al. |
| 8,246,700 B1 | 8/2012 | Kutsin |
| 8,303,676 B1 | 11/2012 | Weaver et al. |
| 8,349,034 B2 | 1/2013 | Calabrese et al. |
| 8,349,039 B2 | 1/2013 | Robinson |
| 8,361,428 B2 | 1/2013 | Raman et al. |
| 8,580,152 B2 | 11/2013 | Sutradhar et al. |
| 8,585,789 B2 | 11/2013 | Sutradhar et al. |
| 8,617,424 B2 | 12/2013 | Badhe et al. |
| 8,722,958 B2 | 5/2014 | Kashimoto |
| 8,734,547 B2 | 5/2014 | Rappas et al. |
| 8,759,596 B2 | 6/2014 | Yie et al. |
| 8,828,105 B2 | 9/2014 | Calabrese et al. |
| 8,863,518 B2 | 10/2014 | Koseoglu |
| 8,915,199 B2 | 12/2014 | Bohlig et al. |
| 8,916,661 B2 | 12/2014 | Bradin |
| 8,957,275 B2 | 2/2015 | Stein et al. |
| 8,999,021 B2 | 4/2015 | Sutradhar et al. |
| 9,023,124 B2 | 5/2015 | Weaver et al. |
| 9,034,061 B2 | 5/2015 | Robinson et al. |
| 9,133,405 B2 | 9/2015 | Abughazaleh |
| 9,139,785 B2 | 9/2015 | Tsantrizos |
| 9,200,207 B2 | 12/2015 | Huang et al. |
| 9,416,077 B2 | 8/2016 | Kelfkens et al. |
| 9,698,439 B2 | 7/2017 | Weaver et al. |
| 9,702,552 B2 | 7/2017 | Ali et al. |
| 9,834,728 B2 | 12/2017 | Fleckner et al. |
| 9,982,205 B2 | 5/2018 | Pichach |
| 10,329,501 B2 | 6/2019 | Bai et al. |
| 2001/0006036 A1 | 7/2001 | Kleiss |
| 2002/0113228 A1 | 8/2002 | Kim et al. |
| 2004/0031424 A1 | 2/2004 | Pope |
| 2004/0103831 A1 | 6/2004 | Pope |
| 2004/0244289 A1 | 12/2004 | Morozumi et al. |
| 2005/0000162 A1 | 1/2005 | Bishop et al. |
| 2006/0219139 A1 | 10/2006 | Pope et al. |
| 2007/0045455 A1 | 3/2007 | Tuzson et al. |
| 2007/0204512 A1 | 9/2007 | Self et al. |
| 2008/0081844 A1* | 4/2008 | Shires ............... C10K 1/20 518/703 |
| 2008/0134579 A1* | 6/2008 | Kulkarni ............ C10J 3/725 48/202 |
| 2009/0217587 A1 | 9/2009 | Raman et al. |
| 2009/0217588 A1 | 9/2009 | Hippo et al. |
| 2010/0038325 A1 | 2/2010 | Benson et al. |
| 2010/0042557 A1 | 2/2010 | Block et al. |
| 2010/0139534 A1 | 6/2010 | Tsantrizos |
| 2010/0186291 A1 | 7/2010 | Yie et al. |
| 2011/0036014 A1* | 2/2011 | Tsangaris ........... C10J 3/721 48/197 FM |
| 2011/0185624 A1 | 8/2011 | Hall |
| 2011/0318515 A1 | 12/2011 | Dubois et al. |
| 2012/0032452 A1 | 2/2012 | Kuku |
| 2012/0266793 A1 | 10/2012 | Bohlig et al. |
| 2013/0082210 A1 | 4/2013 | Gautam et al. |
| 2013/0144087 A1 | 6/2013 | Arora |
| 2013/0269252 A1 | 10/2013 | Tsangaris et al. |
| 2014/0290593 A1 | 10/2014 | Krammer |
| 2015/0096222 A1 | 4/2015 | Calabrese et al. |
| 2015/0211736 A1 | 7/2015 | Bohlig et al. |
| 2015/0337206 A1 | 11/2015 | Iwasa |
| 2016/0002546 A1 | 1/2016 | Bai |
| 2016/0151765 A1 | 6/2016 | Kamata et al. |
| 2017/0088783 A1 | 3/2017 | Nawrocki |
| 2017/0312718 A1 | 11/2017 | Tawfik |
| 2020/0248082 A1* | 8/2020 | Trapp ................ C10K 1/101 |

FOREIGN PATENT DOCUMENTS

| | | |
|---|---|---|
| CN | 101735011 A | 6/2010 |
| CN | 201626935 U | 11/2010 |
| CN | 101805636 B | 7/2013 |
| CN | 203923112 U | 11/2014 |
| CN | 104212471 A | 12/2014 |
| CN | 104479758 A | 4/2015 |
| CN | 104629806 A | 5/2015 |
| CN | 103205279 B | 7/2015 |
| CN | 105219437 A | 1/2016 |
| CN | 105299712 A | 2/2016 |
| CN | 103979491 B | 7/2016 |
| CN | 106381181 A | 2/2017 |
| CN | 106947509 A | 7/2017 |
| CN | 104789268 B | 12/2017 |
| CN | 107497467 A | 12/2017 |
| CN | 105462615 B | 4/2018 |
| CN | 105779017 B | 7/2018 |
| CN | 108557760 A | 9/2018 |
| DE | 42 00 341 A1 | 5/1993 |
| DE | 44 36 226 A1 | 4/1996 |
| DE | 44 46 803 A1 | 6/1996 |
| DE | 10 2016 002 029 B4 | 10/2018 |
| EP | 0 257 019 A2 | 2/1988 |
| EP | 1 462 505 A1 | 9/2004 |
| EP | 3 392 563 A1 | 10/2018 |
| GB | 2556665 A | 6/2018 |
| JP | 10-236801 A | 9/1998 |
| JP | 10-310783 A | 11/1998 |
| JP | 2000-328070 A | 11/2000 |
| JP | 2001-098276 A | 4/2001 |
| JP | 2002-038172 A | 2/2002 |
| JP | 2003-238966 A | 8/2003 |
| JP | 2003-246989 A | 9/2003 |
| JP | 2004-315639 A | 11/2004 |
| JP | 2006-328328 A | 12/2006 |
| JP | 3980426 B2 | 7/2007 |
| JP | 2008-063185 A | 3/2008 |
| JP | 2008-249212 A | 10/2008 |
| JP | 2009-235189 A | 10/2009 |
| JP | 2009-300006 A | 12/2009 |
| JP | 2011-006619 A | 1/2011 |
| JP | 2017-180922 A | 10/2017 |
| JP | 2017-193676 A | 10/2017 |
| JP | 2017-195742 A | 10/2017 |
| JP | 6280484 B2 | 2/2018 |
| JP | 2018-043224 A | 3/2018 |
| JP | 2018-053012 A | 4/2018 |
| JP | 2018-123184 A | 8/2018 |
| JP | 2018-123689 A | 8/2018 |
| KR | 10-2002-0010902 A | 2/2002 |
| KR | 10-0639113 B1 | 10/2006 |
| KR | 10-2011-0000554 A | 1/2011 |
| KR | 10-1669004 B1 | 10/2016 |
| KR | 10-1721823 B1 | 4/2017 |
| WO | WO 94/17161 A1 | 8/1994 |
| WO | WO 2014/043552 A1 | 3/2014 |
| WO | WO 2017/080933 A1 | 5/2017 |
| WO | WO 2017/103527 A1 | 6/2017 |
| WO | WO 2017/115019 A1 | 7/2017 |
| WO | WO 2018/052337 A1 | 3/2018 |

OTHER PUBLICATIONS

Ashida et al.; "Co-pyrolysis of hydrothermally upgraded brown coal and waste plastics;" The Japan Institute of Energy; pp. 97-98.

Barton; "Processing of Urban Waste to Provide Feedstock for Fuel/Energy Recovery;" CEC International Conference, Pyrolysis and Gasification; Luxembourg; Warren Spring Lab Report No. W89026; May 1989; pp. 57-71.

Behzadi et al.; "Liquid Fuel from Plastic Wastes Using Extrusion—Rotary Kiln Reactors;" Chapter 19; Feedstock Recycling and Pyrolysis of Waste Plastics: Converting Waste Plastics into Diesel and Other Fuels; 2006; pp. 531-548.

Bhaskar et al.; "Pyrolysis studies of PP/PE/PS/PVC/HIPS-Br plastics mixed with PET and dehalogenation (Br, Cl) of the liquid products;" J. Anal. Appl. Pyrolysis; 72; 2004; pp. 27-33.

Blazsó; "Recent trends in analytical and applied pyrolysis of polymers;" Journal of Analytical and Applied Pyrolysis; 39; 1997; pp. 1-25.

(56) References Cited

OTHER PUBLICATIONS

Campbell et al.; "The potential for adding plastic waste fuel at a coal gasification power plant;" Waste Manage Res; 2001; 19; ; pp. 526-532.
De Marco et al.; "Recycling polymeric wastes by means of pyrolysis;" J Chem Technol Biotechnol; 77; online: 2002; pp. 817-824.
Elam et al.; "An Integrated Approach to the Recovery of Fuels and Chemicals from Mixed Waste Carpets Through Thermocatalytic Processing;" American Chemical Society, Division of Fuel Chemistry; 1997; 42(4); pp. 993-997.
Encyclopedia of Polymer Science and Technology; Copyright John Wiley & Sons, Inc.; vol. 7; pp. 657-678.
Feng et al.; "Pyrolysis Characteristics and Kinetics of Waste Plastics and Coal Powder;" Journal of Iron and Steel Research; vol. 18; No. 11; Nov. 2006; pp. 11-14, 26.
Fernandez; "La Recuperacion de Los Residuos Plasticos;" Ingenieria Quimica; Oct. 1997; pp. 153-157.
Fernandez; "Reciclado Quimico de Plasticos;" Revista de Plasticos Modernos; No. 477; Marzo 96; pp. 290-301.
García et al.; "Comparison between product yields in the pyrolysis and combustion of different refuse;" J. Anal. Appl. Pyrolysis; 68-69; 2003; pp. 577-598.
Helt et al.; "Liquids from Municipal Solid Waste;" Chapter 8; Soltes and Milne; Pyrolysis Oils from Biomass; ACS Symposium Series; American Chemical Society; Washington, DC; 1988; pp. 79-91.
Huczko et al.; "Plasma Gasification of Surrogate and Real Waste Plastics;" Thermal Solid Waste Utilisation in Regular and Industrial Facilities; 2000; pp. 155-165.
Hujuri et al.; "Modeling pyrolysis kinetics of plastic mixtures;" Polymer Degradation and Stability; 93; 2008; pp. 1832-1837.
Jung; "Pyrolysis and Gasification of Industrial Waste Towards Substitution Fuels Valorisation;" High Temperature Materials and Process Special Issue; vol. 27; No. 5; 2008; pp. 299-304.
Kaminsky; "Chemical Recycling of Mixed Plastics by Pyrolysis;" Advances in Polymer Technology; vol. 14; No. 4; 1995; pp. 337-344.
Kaminsky et al.; "Olefins from polyolefins and mixed plastics by pyrolysis;" Journal of Analytical and Applied Pyrolysis; 32; 1995; pp. 19-27.
Kaminsky et al.; "Pyrolysis of Plastic Waste and Scrap Tires Using a Fluidized-Bed Process;" Chapter 31; Jones and Radding; Thermal Conversion of Solid Wastes and Biomass; ACS Symposium Series; American Chemical Society; Washington, DC; 1995; pp. 423-439.
Kelly et al.; "A Low Cost and High Quality Solid Fuel From Biomass and Coal Fines;" Final Report; DOE Contract No. DE-AC26-99FT40157; Mar. 1, 1999 to May 31, 2000; Altex Technologies Corporation; Jul. 2001; pp. 1-122.
Kim et al.; "Pyrolysis of a fraction of mixed plastic wastes depleted in PVC;" Journal of Analytical and Applied Pyrolysis; 40-41; 1997; pp. 365-372.
Lin; "Recycling Technology of Poly(ethylene Terephthalate) Materials;" Macromol. Symp.; 135; 1998; pp. 129-135.
Luska et al.; "Piroliza jako jedna z metod recyklingu odpadow polimerowych;" Elastomery; Nr 5; pp. 30-36.
Mackey; "A Review of Advanced Recycling Technology;" Chapter 14; Rader et al.; Plastics, Rubber, and Paper Recycling; ACS Symposium Series; American Chemical Society; Washington, DC; 1995; pp. 161-169.
Mallya et al.; "Effects of Feedstock Components on Municipal Solid Waste Pyrolysis;" A.V. Bridgwater et al. (eds.), Research in Thermochemical Biomass Conversion; 1988; pp. 111-126.
Notification of Transmittal of the International Search Report and the Written Opinion of the International Searching Authority, or the Declaration, with Date of Mailing Jun. 30, 2020 received in International Application No. PCT/US2020/024841.
Notification of Transmittal of the International Search Report and the Written Opinion of the International Searching Authority, or the Declaration, with Date of Mailing Jul. 10, 2020 received in International Application No. PCT/US2020/024858.
Notification of Transmittal of the International Search Report and the Written Opinion of the International Searching Authority, or the Declaration, with Date of Mailing Jul. 10, 2020 received in International Application No. PCT/US2020/024851.
Notification of Transmittal of the International Search Report and the Written Opinion of the International Searching Authority, or the Declaration, with Date of Mailing Jul. 10, 2020 received in International Application No. PCT/US2020/024867.
Notification of Transmittal of the International Search Report and the Written Opinion of the International Searching Authority, or the Declaration, with Date of Mailing Jul. 10, 2020 received in International Application No. PCT/US2020/024833.
Notification of Transmittal of the International Search Report and the Written Opinion of the International Searching Authority, or the Declaration, with Date of Mailing Jul. 16, 2020 received in International Application No. PCT/US2020/024836.
Notification of Transmittal of the International Search Report and the Written Opinion of the International Searching Authority, or the Declaration, with Date of Mailing Jul. 17, 2020 received in International Application No. PCT/US2020/024855.
Notification of Transmittal of the International Search Report and the Written Opinion of the International Searching Authority, or the Declaration, with Date of Mailing Jul. 10, 2020 received in International Application No. PCT/US2020/024891.
Notification of Transmittal of the International Search Report and the Written Opinion of the International Searching Authority, or the Declaration, with Date of Mailing Jul. 21, 2020 received in International Application No. PCT/US2020/024887.
Okuwaki; "Feedstock recycling of plastics in Japan;" Polymer Degradation and Stability; 85; 2004; pp. 981-988.
Parra et al.; "Textural characterization of activated carbons obtained from poly(ethylene terephthalate) by carbon dioxide activation;" Studies in Surface Science and Catalysis; 144; pp. 537-543.
Parra et al.; "Textural development and hydrogen adsorption of carbon materials from PET waste;" Journal of Alloys and Compounds; 379; 2004; pp. 280-289.
Piao et al.; "Research and Development on Gasification Technology of Organic Waste Material (OWM) by using Entrained-Flow;" Journal of the Japan Institute of Energy; 82; 2003; pp. 671-678.
Pober et al.; "The Nature of Pyrolytic Oil from Municipal Solid Waste;" Chapter V; Fuels Waste; 1977; pp. 73-85.
Probert et al.; "Harnessing Energy from Domestic, Municipal and Industrial Refuse;" Applied Energy; 27; 1987; pp. 89-168.
Rago et al.; "Torrefaction of textile waste for production of energy-dense biochar using mass loss as a synthetic indicator;" Journal of Environmental Chemical Engineering; 6; 2018; pp. 811-822.
Roy et al.; "Preliminary Feasibility Study of the Biomass Vacuum Pyrolysis Process;" A.V. Bridgwater et al. (eds.); Research in Thermochemical Biomass Conversion; pp. 585-596.
Saha et al.; "Model-free method for isothermal and non-isothermal decomposition kinetics analysis of PET sample;" Thermochimica Acta; 444; 2006; pp. 46-52.
San José et al.; "Fluidodinamica de Los Lechos de Borbor Conicos (Spouted Beds) Para el Tratamiento de REsiduos de Materiales Plasticos;" Informacion Tecnologica; vol. 13; No. 5; 2002; pp. 21-24.
Savage et al.; "Screening Shredded Municipal Solid Waste;" Compost Science Journal of Waste Recycling; Jan./Feb. 1976; pp. 7-11.
Senneca et al.; "Oxidative pyrolysis of solid fuels;" J. Anal. Appl. Pyrolysis; 71; 2004; pp. 959-970.
Shah et al.; "Conversion of Waste Plastic to Oil: Direct Liquefaction versus Pyrolysis and Hydroprocessing;" Energy & Fuels; 13; 1999; pp. 832-838.
Shoji et al.; "Thermal weight analysis of the jet floor gasification process of wasteTen;" Journal of Chemical Engineering; pp. 27-34 (machine translation).
Straka et al.; "Co-pyrolysis of Waste Polymers with Coal;" Macromol. Symp.; 135; 1998; pp. 19-23.
Vasile et al.; "Thermal and catalytic decomposition of mixed plastics;" Journal of Analytical and Applied Pyrolysis; 57; 2001; pp. 287-303.

(56) References Cited

OTHER PUBLICATIONS

Vivero et al.; "Effects of plastic wastes on coal pyrolysis behavior and the structure of semicokes;" J. Anal. Appl. Pyrolysis; 74; 2005; pp. 327-336.
Wilkins et al.; "Review of pyrolysis and combustion products of municipal and industrial wastes;" Journal of Environmental Science & Health Part A; 18:6; 1983; pp. 747-772.
Williams et al.; "Interaction of Plastics in Mixed-Plastics Pyrolysis;" Energy & Fuels; 13; 1999; pp. 188-196.
Williams et al.; "The Pyrolysis of Individual Plastics and a Plastic Mixture in a Fixed Bed Reactor;" J. Chem. Tech. Biotechnol.; 70; 1997; pp. 9-20.
Williams et al.; "The pyrolysis of municipal solid waste;" Journal of the Institute of Energy; Dec. 1992; 65; pp. 192-200.
Williams et al.; "Recycling plastic waste by pyrolysis;" Journal of the Institute of Energy; Jun. 1998; 71; pp. 81-93.
Zhiyuan et al.; "The release law of benzene, radon and fife in the process of pyrococosatic and plastic pyrolytic process;" Environmental Chemistry; vol. 27; No. 6; Nov. 2008; pp. 766-769 (machine translation).

\* cited by examiner

POLYMERS, ARTICLES, AND CHEMICALS MADE FROM HIGH CONCENTRATED RECYCLE DERIVED SYNGAS

CROSS-REFERENCE TO RELATED APPLICATION(S)

This application is a national stage filing under 35 USC § 371 of International Application Number PCT/US2020/024891, filed on, Mar. 26, 2020 which claims the benefit of the filing date to U.S. Provisional Application No. 62/825,858, filed on Mar. 29, 2019 and 62/906,823 filed on Sep. 27, 2019, the entire disclosures of which are incorporated by reference herein.

BACKGROUND

There have been significant efforts underway for recycling various products, and advancement have been made to progress from not only recycling products but to also provide a circular economy such that the life span of a portion of products does not end in a landfill as non-biodegradable material or combusted as carbon dioxide and water. An even more daunting challenge to establishing circularity in at least a portion of a product is the use of the recycled product to make the raw materials fit for making the same types of products as what was recycled.

There remains a need to continue the development of circularity in a variety of products.

A variety of means for the recycle, reuse, or reduction of waste stocks such as biomass, solid municipal waste, high concentrated recycle polymer, and paper have been articulated, among which is the gasification of such waste stocks. In such proposals, waste gasifiers, which are typically air supplied fluidized bed gasifiers that are fed with a variety of component sizes and mixed stock types have been proposed. Such waste gasifiers typically operate at low to medium temperatures in the range of 500° C. to 1000° C. using air as an oxidizer, and given the lower operating temperature, incomplete oxidation reactions occur resulting the generation of high quantities of residues that can appear in both the gas phase (syngas stream) and bottoms solid phase; e.g. tarry substances. The types of residues and their quantity will vary depending on the feedstock composition. Further, while waste gasifiers have the advantage of accepting highly variable sizes and mixed feedstocks, the resulting syngas compositions are also widely variable over time rendering them unusable for making chemicals without installation of expensive post treatments systems to clean up and purify the syngas streams existing the gasifier vessel. Even with purification processes, the hydrogen/carbon monoxide/carbon dioxide ratios can remain highly variable. As a result of the expense to install systems to purify the syngas stream exiting the gasifier vessel suitable for chemicals synthesis, or their compositional variability, or their low throughput, or by reason of a combination of these factors, waste gasifier generated syngas streams are typically used to generate energy, e.g. steam or electricity, or are used as fuel stocks.

Mixed solid municipal wastes (MSW) have been investigated as a feed to a gasifier. MSW compositions contain a variety of solids, including bottles, sheets, films, paper, rubber, cardboard, cups, trays, wood, leather, textiles, glass, metal, etc. After separation of combustibles from non-combustibles (e.g. glass, metal, dirt), the mix of combustibles nevertheless remains highly variable in time from hour to hour, day to day, week to week, month to month, season to season, and by the source location. The variability lies both in form, e.g. bottles, garments, other textiles, personal care items, sheets, films, paper, cardboard, cups, trays, etc., and variability in compositional mix, e.g. polycarbonate, polyethylene, polypropylene, polyethylene terephthalate, polyamides, epoxy resins, acrylonitrilebutadiene, acrylics, alkyds, nylons, polyacetals, polystyrene, polyurethanes, vinyls, styrene acrylonitriles, ureas and melamines, wood, cellulosics, leather, food wastes, etc., variability in source location, and variability in the large variety of mechanical handling processes commercially practiced which employ different physical and chemical separation methods. In fixed bed and fluidized bed gasifiers, this can result in an unacceptable syngas composition variability over time, particularly when the syngas is needed to synthesize chemicals which require a very consistent rate and quality of a high concentrated recycle waste textiles and plastics derived syngas or syngas ingredients.

Additionally, the components of MSW such as textiles and/or plastics have a fixed carbon content that is lower than solid fossil fuel sources such as coal or petcoke. As a result, textiles and/or plastics will combust and generate the syngas components at a more rapid rate than, for example, coal. Carbon monoxide generated from textiles or plastics will, therefore, have a longer residence time to convert to carbon dioxide under coal gasification conditions. While high concentrated recycle polymer (e.g., textiles and plastics) have a high heat value ("HHV"), even in some cases equal to or exceeding coal, its use can also result in the generation of undesirable amounts of carbon dioxide in the raw syngas stream, particularly at high temperatures and pressures, along with a reduction in the amount of carbon monoxide that could have been produced by feeding only a fossil fuel.

It would be desirable to provide a circular life cycle of waste materials, e.g., plastics and/or textiles, that includes recycling post-consumer or postindustrial plastics and/or textiles back to new chemicals which reduces or avoids the drawbacks discussed above.

SUMMARY

It has been determined that fixed bed waste gasifiers designed to accept combustible MSW streams are not attractive options for generating a syngas stream for making chemicals. The option of separating desirable components from an MSW stream, such as textiles and/or plastics, or collecting textiles and/or plastics, as feeds to a gasifier has been considered. However, the volumes of available textiles and/or plastics as isolated feedstocks are low and insufficient to feed typical commercial scale entrainment or fixed/moving bed gasifier operating at capacity, and particularly those producing syngas for making chemicals.

It would be desirable to incorporate textiles and/or plastics, rather than an MSW stream, into a feedstock to a gasifier producing a syngas stream suitable for making chemicals. It would also be desirable to accommodate the gasification process for the low volume availability of textile and/or plastic recycle feedstocks in commercial scale gasifiers producing syngas. It would also be desirable to operate the gasification process that minimizes the generation of carbon dioxide. It would also be desirable to conduct the gasification process in a manner that generates more carbon monoxide per mole of carbon dioxide relative to MSW feedstocks to gasifiers operated at lower temperature and/or lower pressure in waste gasifiers, and to reduce the quantity of incomplete oxidation residues (e.g. tar, char, etc.) relative to waste gasifiers. It is also desirably to conduct the operations on a commercial scale.

We have discovered the desirability and opportunities to not only employ circularity in a portion of consumer or industrial polymers and products, but also to combine the circularity with producing the same raw materials used to make the polymers and articles that were the subject of recycle. In addition, there is provided a means to combine circularity with remaking at least a portion of such polymers and products with biodegradable material and with material from sustainable sources to develop a new generation of products having circular, biodegradable, and sustainable features. Many attempts have been made to develop circularity into products, but many of such attempts are not commercially scalable in a cost-efficient manner.

An example of a polymer or article that is a candidate for accomplishing one or more of the objectives is a cellulose ester and the fibers or other consumer products made from high concentrated recycle derived cellulose esters. Cellulose, one of the raw materials to make a high concentrated recycle derived cellulose ester, is a sustainable and renewable material in that it is obtained from plant material such as wood. However, the acyl groups attached to the cellulose backbone are generally made from intermediate chemicals derived fossil fuels (e.g., oil, natural gas, coal). The present invention offers a way to include both renewable and recycled content in high concentrated recycle derived cellulose esters by providing high concentrated recycle derived cellulose esters that are made from cellulose and organic compounds, e.g., acids or their anhydrides, derived from recycled, reused or other environmentally favored raw material.

In an aspect, a method is provided to incorporate recycle textiles and/or plastics ("Recycle Polymer") into a gasifier feedstock at high concentration to produce a high concentrated recycle derived syngas stream suitable for making chemicals. It embodiments, a high concentrated recycle derived syngas stream is generated that is suitable for chemicals synthesis in which more carbon monoxide is formed in the high concentrated recycle derived syngas using feedstocks containing high concentrations of recycle polymer relative to lower temperature and/or lower pressure MSW fed fixed bed waste gasifiers, and to reduce the quantity of incomplete oxidation residues (e.g. tar, char, etc.). In embodiments, a high concentrated recycle derived syngas stream output from a gasifier vessel is generated which is sufficiently compositionally consistent over time and suitable for making chemicals. In embodiments, a process is provided where it is possible to conduct the operations efficiently, in a stable manner, and on a commercial scale. From the high concentrated recycle derived syngas made by such a process, chemicals can be made which ultimately will form a raw material to make a variety of polymers or articles, including high concentrated recycle derived cellulose esters.

There is now provided a high concentrated recycle derived cellulose ester reactant, a high concentrated recycle derived cellulose ester, a high concentrated recycle derived acetic acid, a high concentrated recycle derived acetic anhydride, a high concentrated recycle derived methanol, a high concentrated recycle derived methyl acetate, a high concentrated recycle derived cellulose ester fiber, a high concentrated recycle derived textile, and/or a high concentrated recycle derived nonwoven web.

There is also provided a process of making a high concentrated recycle derived polymer reactant, comprising making a high concentrated recycle derived syngas, and reacting said high concentrated recycle derived syngas to make the high concentrated recycle derived polymer reactant optionally through one or more high concentrated recycle derived chemical intermediates.

There is also provided a process of making a high concentrated recycle derived polymer, comprising reacting a high concentrated recycle derived polymer reactant with a second reactant to make said polymer.

There is also provide a process for preparing a high concentrated recycle derived polymer comprising:
a. making a high concentrated recycle derived syngas by gasifying solid fossil fuels and high concentrated recycle polymer;
b. using the high concentrated recycle derived syngas as a feedstock in a reaction scheme to produce at least high concentrated recycle derived polymer reactant for preparing a polymer; and
c. reacting said at least one polymer reactant to prepare a high concentrated recycle derived polymer.

There is further provided a process of making a high concentrated recycle derived fiber, comprising making a high concentrated recycle derived polymer and spinning said polymer into the fiber.

There is also provided a circular manufacturing process comprising:
(i) providing a first recycle polymer, and
(ii) gasifying a high concentration of said recycle polymer to produce a high concentrated recycle derived syngas, and
(iii) reacting said high concentrated recycle derived syngas to make a high concentrated recycle derived textile and/or plastic through intermediates which all have their origin in part to said high concentrated recycle derived syngas.

There is also provided a high concentrated recycle derived cellulose ester that is synthesized from (i) a raw material that is sustainable, and (ii) a raw material at least a portion of which is obtained, through one or more intermediate steps, from a high concentration of recycle polymers, wherein the cellulose ester is biodegradable.

There is also provided an integrated process for preparing a high concentrated recycle derived cellulose ester comprising:
a. preparing a high concentrated recycle derived syngas obtained by gasifying a solid fossil fuel source and high concentration of recycle polymer;
b. preparing at least one high concentrated recycle derived chemical intermediate from said high concentrated recycle derived syngas;
c. reacting said high concentrated recycle derived chemical intermediate in a reaction scheme to prepare at least one high concentrated recycle derived cellulose reactant as a raw material for preparing a high concentrated recycle derived cellulose ester, and/or selecting said high concentrated recycle derived chemical intermediate to be at least one high concentrated recycle derived cellulose reactant for preparing a high concentrated recycle derived cellulose ester; and
d. reacting said at least one high concentrated recycle derived cellulose reactant to prepare said high concentrated recycle derived cellulose ester.

A high concentration of recycle polymer can be used in a gasification process reliably, with high quality and a consistent composition, while minimizing generation of carbon dioxide. There is also provided a process for the production of a high concentrated recycle polymer derived syngas to make at least one chemical comprising campaigning the production of a syngas from a single gasifier between one or more first feedstock streams to produce a first syngas for a first period of time, and transitioning to one or more second feedstock streams to produce a second syngas for a second period of time, wherein the one or more first feedstock streams comprises a solid fossil fuel and said one or more second feedstock streams comprise textiles and/or plastics, wherein the amount of textiles and/or plastics fed to the gasifier in the second time period is higher than the amount, if any, of textiles and/or plastics fed to the gasifier in the first time period, and the gasifier is operated at a lower gasification temperature during at least a portion of the second time period than the gasification temperature in the first time period, said second syngas being a high concentrated recycle polymer derived syngas.

DETAILED DESCRIPTION

Unless otherwise stated, reference to the weight of the feedstock composition includes all solids, and if present liquids, fed to the gasifier, and unless otherwise stated, does not include the weight of any gases in the feedstock composition as fed to the injector or gasifier.

Reference made throughout to a high concentrated recycle derived syngas, a high concentrated recycle derived chemical intermediate, high concentrated recycle derived cellulose ester reactants, high concentrated recycle derived cellulose ester polymers, their fibers, articles made from the fibers including nonwoven webs, yarns, cloth, fabric, and textiles includes, in each case, that at least a portion are derived, directly or indirectly, from a source of recycle polymer that is gasified in high concentrations.

By a "high concentrated recycle derived" gas, chemical compound, polymer, fiber, nonwoven web, sheet, film, textile, or any other product (collectively a "material") is meant that at least a portion of the material finds its immediate source, or its ultimate source through one or more intermediate materials, from a high concentration of recycle polymers that are gasified. Desirably, at least a portion of each gas, compound or reactant in a chain to make the material of interest finds at least a portion of its source in high concentrated recycle polymers that are gasified.

By a "high concentration" is meant that a second feedstock contains recycle polymer (e.g. textiles and/or plastics) in an amount that is higher than the amount of recycle polymer used, if any, in a first feedstock to the same gasifier at different times, and the second feedstock contains at least more than 2 wt. % recycle polymer based on the weight of all solid fuel fed to the gasifier.

By gasifying a high concentrated recycle polymer in a gasifier that makes syngas of a quantity and quality suitable for making chemicals, a variety of chemicals and polymer can now be made containing the molecular components of the high concentrated recycle derived syngas.

There is now provided a high concentrated recycle derived cellulose ester reactant, a high concentrated recycle derived cellulose ester, a high concentrated recycle derived acetic acid, a high concentrated recycle derived acetic anhydride, a high concentrated recycle derived methanol, a high concentrated recycle derived methyl acetate, a high concentrated recycle derived cellulose ester fiber, a high concentrated recycle derived textile, and/or a high concentrated recycle derived nonwoven web.

As an example, reference is made to making a cellulose ester. In one embodiment, a high concentrated recycle derived cellulose ester composition is provided comprising at least one high concentrated recycle derived cellulose ester having at least one substituent on an anhydroglucose unit (AU) derived from high concentrated recycle derived syngas.

In embodiments, the high concentrated recycle derived cellulose ester utilized in this invention can be any that is known in the art. High concentrated recycle derived cellulose esters that can be used for the present invention generally comprise repeating units of the structure:

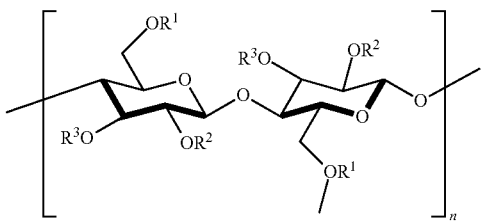

wherein $R^1$, $R^2$, and $R^3$ are selected independently from the group consisting of hydrogen or straight chain alkanoyl having from 2 to 10 carbon atoms. For high concentrated recycle derived cellulose esters, the substitution level is usually express in terms of degree of substitution (DS), which is the average number of non-OH substitutents per anhydroglucose unit (AGU). Generally, conventional cellulose contains three hydroxyl groups in each AGU unit that can be substituted; therefore, DS can have a value between zero and three. However, low molecular weight cellulose mixed esters can have a total degree of substitution slightly above 3, due to end group contributions. Native cellulose is a large polysaccharide with a degree of polymerization from 250-5,000 even after pulping and purification, and thus the assumption that the maximum DS is 3.0 is approximately correct. However, as the degree of polymerization is lowered, as in low molecular weight cellulose mixed esters, the end groups of the polysaccharide backbone become relatively more significant, thereby resulting in a DS that can range in excess of 3.0. Low molecular weight cellulose mixed esters are discussed in more detail subsequently in this disclosure. Because DS is a statistical mean value, a value of 1 does not assure that every AGU has a single substitutent. In some cases, there can be unsubstituted anhydroglucose units, some with two and some with three substitutents, and typically the value will be a non-integer. Total DS is defined as the average number of all of substituents per anhydroglucose unit. The degree of substitution per AGU can also refer to a particular substitutent, such as, for example, hydroxyl, acetyl, butyryl, or propionyl. In embodiments, the degree of polymerization for the cellulose ester is lower than that of the native cellulose. In embodiments, n is an integer in a range from 25 to 250, or 25 to 200, or 25 to 150, or 25 to 100, or 25 to 75.

In embodiments, the high concentrated recycle derived cellulose ester utilized can be a cellulose triester or a secondary high concentrated recycle derived cellulose ester. Examples of cellulose triesters include, but are not limited to, cellulose triacetate, cellulose tripropionate, or cellulose tributyrate. Examples of secondary high concentrated recycle derived cellulose esters include cellulose acetate, cellulose acetate propionate, and cellulose acetate butyrate.

In one embodiment, the high concentrated recycle derived cellulose ester can be chosen from cellulose acetate (CA), cellulose propionate (CP), cellulose butyrate (CB), cellulose acetate propionate (CAP), cellulose acetate butyrate (CAB), cellulose propionate butyrate (CPB), and the like, or combinations thereof. Examples of such high concentrated recycle derived cellulose esters are described in U.S. Pat. Nos. 1,698,049; 1,683,347; 1,880,808; 1,880,560; 1,984,147, 2,129,052; and 3,617,201, incorporated herein by reference in their entirety to the extent that they do not contradict the statements herein.

In embodiments, the high concentrated recycle derived cellulose esters have at least 2 anhydroglucose rings and can have between at least 50 and up to 5,000 anhydroglucose rings. The number of anhydroglucose units per molecule is defined as the degree of polymerization (DP) of the high concentrated recycle derived cellulose ester. In embodiments, high concentrated recycle derived cellulose esters can have an inherent viscosity (IV) of about 0.2 to about 3.0 deciliters/gram, or about 0.5 to about 1.8, or about 1 to about 1.5, as measured at a temperature of 25° C. for a 0.25-gram sample in 100 ml of a 60/40 by weight solution of phenol/tetrachloroethane. Examples of high concentrated recycle derived cellulose esters include, but are not limited to, cellulose acetate, cellulose diacetate, cellulose propionate, cellulose butyrate, cellulose acetate propionate (CAP), cellulose acetate butyrate (CAB), cellulose propionate butyrate, and the like. In embodiments, high concentrated recycle derived cellulose esters useful herein can have a DS/AGU of about 2 to about 2.99, and the substituting ester can comprise acetyl, propionyl, butyryl, or any combinations of these. In another embodiment, the total DS/AGU ranges from about 2 to about 2.99 and the DS/AGU of acetyl ranges from about 0 to 2.2, with the remainder of the ester groups comprising propionyl, butyryl or combinations thereof.

High concentrated recycle derived cellulose esters can be produced by any method known in the art. Examples of processes for producing high concentrated recycle derived cellulose esters are taught in Kirk-Othmer, Encyclopedia of Chemical Technology, 5th Edition, Vol. 5, Wiley-Interscience, New York (2004), pp. 394-444. Cellulose, the starting material for producing high concentrated recycle derived cellulose esters, can be obtained in different grades and sources such as from cotton linters, softwood pulp, hardwood pulp, corn fiber and other agricultural sources, and bacterial cellulose, among others.

One method of producing high concentrated recycle derived cellulose esters is esterification of the cellulose by mixing cellulose with the appropriate high concentrated recycle derived organic acids, high concentrated recycle derived acid anhydrides, and catalysts. Cellulose is then converted to a cellulose triester. Ester hydrolysis is then performed by adding a water-acid mixture to the cellulose triester, which can then be filtered to remove any gel particles or fibers. Water is then added to the mixture to precipitate the high concentrated recycle derived cellulose ester. The high concentrated recycle derived cellulose ester can then be washed with water to remove reaction by-products followed by dewatering and drying.

The cellulose triesters to be hydrolyzed can have three substitutents selected independently from alkanoyls having from 2 to 10 carbon atoms. Examples of cellulose triesters include cellulose triacetate, cellulose tripropionate, and cellulose tributyrate or mixed triesters of cellulose such as cellulose acetate propionate, and cellulose acetate butyrate. These high concentrated recycle derived cellulose esters can be prepared by a number of methods known to those skilled in the art. For example, high concentrated recycle derived cellulose esters can be prepared by heterogeneous acylation of cellulose in a mixture of carboxylic acid and anhydride, at least one of which and at least a portion of which are a high concentrated recycle derived cellulose reactant, in the presence of a catalyst such as H2SO4. Cellulose triesters can also be prepared by the homogeneous acylation of cellulose dissolved in an appropriate solvent such as LiCl/DMAc or LiCl/NMP.

Those skilled in the art will understand that the commercial term of cellulose triesters also encompasses high concentrated recycle derived cellulose esters that are not completely substituted with acyl groups. For example, cellulose triacetate commercially available from Eastman Chemical Company, Kingsport, TN, U.S.A., typically has a DS from about 2.85 to about 2.99.

After esterification of the cellulose to the triester, part of the acyl substitutents can be removed by hydrolysis or by alcoholysis to give a secondary high concentrated recycle derived cellulose ester. As noted previously, depending on the particular method employed, the distribution of the acyl substituents can be random or non-random. Secondary high concentrated recycle derived cellulose esters can also be prepared directly with no hydrolysis by using a limiting amount of acylating reagent. This process is particularly useful when the reaction is conducted in a solvent that will dissolve cellulose. All of these methods yield high concentrated recycle derived cellulose esters that are useful in this invention.

In embodiments, the secondary high concentrated recycle derived cellulose esters useful in the present invention have an absolute weight average molecular weight (Mw) from about 5,000 to about 400,000 as measured by gel permeation chromatography (GPC) according to ASTM D6474. The following method is used to calculate the absolute weight average molecular weight values (Mw) for CE. The solvent is THF stabilized with BHT Preservative. The instrumentation for the THF/high concentrated recycle derived cellulose ester procedure consists of the following Agilent 1200 series components: degasser, isocratic pump, auto-sampler, column oven, UV/Vis detector and a refractive index detector. The test temperature is 30° C. and flow rate is 1.0 ml/min. A sample solution of 25 mg high concentrated recycle derived cellulose ester in 10 ml THF with BHT preservative and 10 µl toluene flow rate marker is made. The injection volume is 50 µl. The column set is Polymer Laboratories 5 µm PLgel, Guard+Mixed C+Oligopore. The detection is by refractive index. The calibrants are monodisperse polystyrene standards, Mw=580 to 3,220,000 from Polymer Laboratories. The universal calibration parameters are as follows: PS (K=0.0001280 and a=0.7120) and CE (K=0.00007572 and a=0.8424). The universal calibration parameters above were determined by light scattering and viscometery to yield the correct weight average molecular weights. In a further embodiment, the Mw is from about 15,000 to about 300,000. In yet further embodiments, the Mw ranges from about 10,000 to about 250,000; from about 15000 to 200000; from about 20,000 to about 150,000; from about 50,000 to about 150,000, or from about 70,000 to about 120,000.

The most common commercial secondary high concentrated recycle derived cellulose esters are prepared by initial acid catalyzed heterogeneous acylation of cellulose to form the cellulose triester. After a homogeneous solution in the corresponding carboxylic acid of the cellulose triester is obtained, the cellulose triester is then subjected to hydrolysis until the desired degree of substitution is obtained. After isolation, a random secondary high concentrated recycle derived cellulose ester is obtained. That is, the relative degree of substitution (RDS) at each hydroxyl is roughly equal.

The high concentrated recycle derived cellulose esters useful in the present invention can be prepared using techniques known in the art, and can be chosen from various types of high concentrated recycle derived cellulose esters, such as for example the high concentrated recycle derived cellulose esters that can be obtained from Eastman Chemical Company, Kingsport, TN, U.S.A., e.g., Eastman™ Cellulose Acetate Propionate CAP 482-20, Eastman™ Cellulose Acetate Propionate CAP 141-20, Eastman™ Cellulose Acetate Butyrate CAB 381-20, Cellulose Acetate Butyrate CAB 171-15 and Eastman™ Cellulose Acetate CA 398-30.

In embodiments, the high concentrated recycle derived cellulose esters can contain chemical functionality and are described herein as either derivatized, modified, or functionalized high concentrated recycle derived cellulose esters. Functionalized high concentrated recycle derived cellulose esters can be produced by reacting the free hydroxyl groups of high concentrated recycle derived cellulose esters with a bifunctional reactant that has one linking group for grafting to the high concentrated recycle derived cellulose ester and one functional group to provide a new chemical group to the high concentrated recycle derived cellulose ester. Examples of such bifunctional reactants include succinic anhydride which links through an ester bond and provides acid functionality; mercaptosilanes which links through alkoxysilane bonds and provides mercapto functionality; and isocyanotoethyl methacrylate which links through a urethane bond and gives methacrylate functionality.

In embodiments, the high concentrated recycle derived cellulose esters can be prepared by converting cellulose to high concentrated recycle derived cellulose esters with reactants that are obtained, through one or more intermediate steps, from a high concentrated recycle derived syngas source. In embodiments, such reactants can be high concentrated recycle derived cellulose reactants that include organic acids and/or acid anhydrides, at least one of which is high concentrated recycle derived, used in the esterification or acylation reactions of the cellulose, e.g., as discussed herein.

By "high concentrated recycle derived syngas" is meant high concentrated recycle derived syngas obtained from a synthesis gas obtained by gasifying a solid fossil fuel source and a high concentrated recycle textile and/or plastic source, as described in the various embodiments more fully herein below. In embodiments, the feedstock (for the synthesis gas operation) can be in the form of a combination of one or more particulated fossil fuel sources and high concentrated recycle plastics and/or textiles.

Reference to the formation of a high concentrated recycle derived syngas, the manufacture and use of high concentrated recycle derived chemical intermediates or high concentrated recycle derived cellulose reactants, means that at least a portion of such gas or chemicals are used to make chemicals or polymers. For example, reference to the use of a high concentrated recycle derived cellulose ester reactant to make a high concentrated recycle derived cellulose ester does not imply that the entire amount of the reactant used to make the high concentrated recycle derived cellulose ester is derived from a textile and/or plastic, but rather that at least a portion of the batch or stream of the high concentrated recycle derived cellulose ester reactant contains a high concentrated recycle derived cellulose ester reactant, or put another way, at least a portion of the acyl groups on the high concentrated recycle derived cellulose ester were obtained from reactants, that through one or more intermediate steps, were obtained from a high concentrated recycle derived syngas.

In embodiments, the high concentrated recycle derived syngas is utilized to make at least one high concentrated recycle derived chemical intermediate in a reaction scheme to make a high concentrated recycle derived cellulose ester (CE intermediate). In embodiments, the high concentrated recycle derived syngas can be a component of feedstock (used to make at least one CE intermediate) that includes other sources of high concentrated recycle derived syngas, hydrogen, carbon monoxide, or combinations thereof. In embodiments, the only source of high concentrated recycle derived syngas used to make the CE intermediates is the high concentrated recycle derived syngas.

Reference to a reaction scheme means reacting a reactant to make one or more intermediates that are used to make the desired end chemical or polymer, and all the reaction process to accomplish the manufacture of the chemical or polymer In embodiments, the high concentrated recycle derived intermediates made directly from, or through one or more intermediate steps from, high concentrated recycle derived syngas can include methanol, acetic acid, methyl acetate, acetic anhydride and combinations thereof. In embodiments, the high concentrated recycle derived chemical intermediates can be derived from at least one reactant or made into at least one product in one or more of the following reactions: (1) high concentrated recycle derived syngas conversion to methanol; (2) high concentrated recycle derived syngas conversion to acetic acid; (3) methanol conversion to acetic acid, e.g., carbonylation of methanol to produce acetic acid; (4) producing methyl acetate from methanol and acetic acid; and (5) conversion of methyl acetate to acetic anhydride, e.g., carbonylation of methyl acetate and methanol to acetic acid and acetic anhydride.

In embodiments, high concentrated recycle derived syngas is used to produce at least one high concentrated recycle derived cellulose reactant. In embodiments, the high concentrated recycle derived syngas is used to produce at least one high concentrated recycle derived cellulose ester.

In embodiments, the high concentrated recycle derived syngas is utilized to make acetic anhydride. In embodiments, high concentrated recycle derived syngas that comprises high concentrated recycle derived syngas is first converted to methanol and this methanol is then used in a reaction scheme to make acetic anhydride. "RDS acetic anhydride" refers to acetic anhydride that is derived from high concentrated recycle derived syngas. Derived from means that at least some of the feedstock source material (that is used in any reaction scheme to make a CE intermediate) has some content of high concentrated recycle derived syngas.

In embodiments, the RDS acetic anhydride is utilized as a CE intermediate reactant for the esterification of cellulose to prepare a high concentrated recycle derived cellulose ester, as discussed more fully above. In embodiments, the RDS acetic acid is utilized as a reactant to prepare cellulose acetate or cellulose diacetate.

In embodiments, the RDS acetic anhydride is utilized to make a biodegradable high concentrated recycle derived cellulose ester.

In one aspect, a high concentrated recycle derived cellulose ester composition is provided that comprises at least one high concentrated recycle derived cellulose ester having at least one substituent on an anhydroglucose unit (AGU) derived from high concentrated recycle derived syngas. In embodiments, the substituent is a combination of acetyl and propionyl functional groups. In embodiments, the substituent is a combination of acetyl and butyryl functional groups. In embodiments, the substituent is any combination of organic acid functional groups. In an embodiment, the at least one substituent is an acetyl functional group.

In embodiments, the high concentrated recycle derived cellulose ester is cellulose di-acetate (CDA). In an embodiment, the high concentrated recycle derived cellulose ester is cellulose tri-acetate (CTA).

In embodiments, the high concentrated recycle derived cellulose ester is prepared from a high concentrated recycle derived cellulose reactant that comprises acetic anhydride that is derived from high concentrated recycle derived syngas.

In embodiments, the high concentrated recycle derived syngas comprises gasification products from a gasification feedstock. In an embodiment, the gasification products are produced by a gasification process using a gasification feedstock that comprises high concentrated recycle polymer. In embodiments, the gasification feedstock comprises coal.

In embodiments, the gasification feedstock comprises a liquid slurry that comprises coal and high concentrated recycle polymer. In embodiments, the gasification process comprises gasifying said gasification feedstock in the presence of oxygen.

In one aspect, a high concentrated recycle derived cellulose ester composition is provided that comprises at least one high concentrated recycle derived cellulose ester having at least one substituent on an anhydroglucose unit (AGU) derived from one or more high concentrated recycle derived chemical intermediates, at least one of which is obtained at least in part from high concentrated recycle derived syngas.

In aspects, an article is provided that comprises the high concentrated recycle derived cellulose ester compositions, as described herein. In embodiments, the article is a textile fabric. In embodiments, the article is biodegradable and/or compositable. In embodiments, a staple fiber is provided that comprises a high concentrated recycle derived cellulose ester composition that comprises cellulose acetate, as described herein. In embodiments, the cellulose ester composition can further comprise one or more of the additives of fillers described herein (with respect to possible feedstock plastics). In embodiments, an article is provided that comprises such a composition. In embodiments, the article is a durable thermoplastic article.

In embodiments, the high concentrated recycle derived cellulose ester is biodegradable. In embodiments, the high concentrated recycle derived cellulose ester is biodegradable and contains content derived from a renewable source, e.g., cellulose from wood or cotton linter, and content derived from a recycled material source, e.g., high concentrated recycle polymer. Thus, in embodiments, a thermoplastic material is provided that is biodegradable and contains both renewable and recycled content, i.e., made from renewable and recycled sources.

In one aspect, the invention is directed to a fiber comprising at least one high concentrated recycle derived cellulose ester, as described herein. In embodiments, sheets, webs or fabrics are provided that comprise such fibers. In embodiments, the sheets, webs or fabrics can be woven or non-woven. In embodiments, the sheets, webs or fabrics can be wet laid or dry laid.

In embodiments, the invention is directed to a spun yarn that comprises at least one high concentrated recycle derived cellulose ester, as described herein. In embodiments, fibers comprising at least one high concentrated recycle derived cellulose ester can be prepared by spinning fibers. The fibers can be spun as a continuous fiber or can be cut to a desired length.

In embodiments, the invention can include fibers, filaments, yarns and nonwoven fabrics as described in WO2018/160588 A1, published on Sep. 7, 2018 (Applicant: Eastman Chemical Company), the contents of which is incorporated herein by reference, with the proviso that the fibers, filaments, yarns or nonwoven fabrics comprise at least one high concentrated recycle derived cellulose ester having high concentrated recycle derived content, as described more fully herein.

In embodiments, the invention is directed to a textile fabric comprising fibers that comprise at least one high concentrated recycle derived cellulose ester, as described herein. In embodiments, the textile fabric can be prepared from fibers made with such high concentrated recycle derived cellulose esters. Such fibers can be used to make slivers, spun yarns, nonwoven webs, cloth, fabric, whether woven, knitted, or made from dry laid nonwovens. The fibers can be filaments or staple fibers.

It has been found that slivers can be successfully formed from CA staple fibers and further processed successfully to spun yarns to make textile fabric. CA staple fibers may be environmentally-friendly, exhibit thermoplastic behavior, have a soft feel similar to that of cotton, and can be processed using both new and existing processing equipment. A CA staple fiber means a cellulose acetate staple fiber, and a "staple fiber" refers to a fiber cut from a continuous filament or tow band of continuous filaments. A carded sliver, spun yarn, or textile fabric "obtained from" a described element includes any number and type of intervening steps or process operations.

Staple fibers and filaments as described herein may be formed from one or more high concentrated recycle derived cellulose esters including, but not limited to, cellulose acetate, cellulose propionate, cellulose butyrate, cellulose acetate formate, cellulose acetate propionate, cellulose acetate butyrate, cellulose propionate butyrate, and mixtures thereof. Although described herein with reference to "cellulose acetate," it should be understood that one or more of the above cellulose acid esters or mixed esters may also be used to form the fibers, nonwovens, and articles as described herein. Various types of high concentrated recycle derived cellulose esters are described, for example, in U.S. Pat. Nos. 1,698,049; 1,683,347; 1,880,808; 1,880,560; 1,984,147, 2,129,052; and 3,617,201, each of which is incorporated herein by reference to the extent not inconsistent with the present disclosure. In some cases, other types of treated or regenerated cellulose (e.g., viscose, rayon, or lyocell) may or may not be used in forming staple fibers as described herein.

When the staple fiber or filament is formed from cellulose acetate, it may be formed from cellulose diacetate, cellulose triacetate, or mixtures thereof. The cellulose acetate (or other high concentrated recycle derived cellulose ester) useful in embodiments of the present invention can have a degree of substitution in the range of from 1.9 to 2.9. As used herein, the term "degree of substitution" or "DS" refers to the average number of acyl substituents per anhydroglucose ring of the cellulose polymer, wherein the maximum degree of substitution is 3.0, as described above. In some cases, the cellulose acetate used to form fibers as described herein may have an average degree of substitution of at least about 1.95, 2.0, 2.05, 2.1, 2.15, 2.2, 2.25, or 2.3 and/or not more than about 2.9, 2.85, 2.8, 2.75, 2.7, 2.65, 2.6, 2.55, 2.5, 2.45, 2.4, or 2.35, with greater than 90, 91, 92, 93, 94, 95, 96, 97, 98, or 99 percent of the cellulose acetate having a degree of substitution greater than 2.15, 2.2, or 2.25. In some cases, greater than 90 percent of the cellulose acetate can have a degree of substitution greater than 2.2, 2.25, 2.3, or 2.35. Typically, acetyl groups can make up at least about 1, 5, 10, 15, 20, 25, 30, 35, 40, 45, 50, 55, or 60 percent and/or not more than about 99, 95, 90, 85, 80, 75, or 70 percent of the total acyl substituents.

In embodiments, the cellulose acetate may have a weight-average molecular weight (Mw) of not more than 90,000, measured using gel permeation chromatography with N-methyl-2-pyrrolidone (NMP) as the solvent. In some cases, the cellulose acetate may have a molecular weight of at least about 10,000, at least about 20,000, 25,000, 30,000, 35,000, 40,000, or 45,000 and/or not more than about 100,000, 95,000, 90,000, 85,000, 80,000, 75,000, 70,000, 65,000, 60,000, or 50,000.

In embodiments, the invention is directed to a staple fiber or filament formed from cellulose acetate, as described herein. In embodiments, the fiber is at least partially coated with at least one finish. In embodiments, the fiber has a denier per filament of less than about 3.0 and a crimp frequency of less than 22 crimps per inch (CPI). In embodiments, a plurality of the fibers exhibits a fiber-to-fiber staple pad coefficient of friction of not more than about 0.70.

In aspects, a carded nonwoven web or a carded sliver is provided comprising CA staple fibers that comprise cellulose acetate prepared according to the methods described herein. A carded sliver is a continuous bundle or strand of loose untwisted fibers that are aligned generally relatively parallel to each other. This alignment is conducted by subjecting the fibers to a carding process.

Other types of fibers suitable for use in a blend with high concentrated recycle derived cellulose ester staple fibers and filament can include natural and/or synthetic fibers including, but not limited to, cotton, rayon, viscose) or other types of regenerated cellulose such as Cupro, Tencel, Modal, and Lyocell cellulose, acetates such as polyvinylacetate, wool, glass, polyamides including nylon, polyesters such as polyethylene terephthalate (PET), polycyclohexylenedimethylene terephthalate (PCT) and other copolymers, olefinic polymers such as polypropylene and polyethylene, polycarbonates, poly sulfates, poly sulfones, polyethers, acrylics, acrylonitrile copolymers, polyvinylchloride (PVC), poly lactic acid, poly glycolic acid and combinations thereof.

In embodiments, the fibers, and yarns and nonwovens and cloths, fabrics and textiles formed therefrom can be biodegradable, meaning that such fibers are expected to decompose under certain environmental conditions. The degree of degradation can be characterized by the weight loss of a sample over a given period of exposure to certain environmental conditions. In some cases, the material used to form the staple fibers, the fibers, or the nonwoven webs or articles produced from the fibers can exhibit a weight loss of at least about 5, 10, 15, or 20 percent after burial in soil for 60 days and/or a weight loss of at least about 15, 20, 25, 30, or 35 percent after 15 days of exposure to a typical municipal composter. However, the rate of degradation may vary depending on the particular end use of the fibers, as well as the composition of the remaining article, and the specific test. Exemplary test conditions are provided in U.S. Pat. Nos. 5,970,988 and 6,571,802.

In some embodiments, the high concentrated recycle derived cellulose ester fibers may be biodegradable fibers and such fibers may be used to form fibrous articles such as textiles, nonwoven fabrics, filters, and yarns. It has been found that high concentrated recycle derived cellulose ester fibers as described herein exhibit enhanced levels of environmental non-persistence, characterized by better-than-expected degradation under various environmental conditions. Fibers and fibrous articles described herein may meet or exceed passing standards set by international test methods and authorities for industrial compostability, home compostability, and/or soil biodegradability.

To be considered "compostable," a material must meet the following four criteria: (1) the material must be biodegradable; (2) the material must be disintegrable; (3) the material must not contain more than a maximum amount of heavy metals; and (4) the material must not be ecotoxic. As used herein, the term "biodegradable" generally refers to the tendency of a material to chemically decompose under certain environmental conditions. Biodegradability is an intrinsic property of the material itself, and the material can exhibit different degrees of biodegradability, depending on the specific conditions to which it is exposed. The term "disintegrable" refers to the tendency of a material to physically decompose into smaller fragments when exposed to certain conditions. Disintegration depends both on the material itself, as well as the physical size and configuration of the article being tested. Ecotoxicity measures the impact of the material on plant life, and the heavy metal content of the material is determined according to the procedures laid out in the standard test method.

The high concentrated recycle derived cellulose ester fibers can exhibit a biodegradation of at least 70 percent in a period of not more than 50 days, when tested under aerobic composting conditions at ambient temperature (28° C.±2° C.) according to ISO 14855-1 (2012). In some cases, the high concentrated recycle derived cellulose ester fibers can exhibit a biodegradation of at least 70 percent in a period of not more than 49, 48, 47, 46, 45, 44, 43, 42, 41, 40, 39, 38, or 37 days when tested under these conditions, also called "home composting conditions." These conditions may not be aqueous or anaerobic. In some cases, the high concentrated recycle derived cellulose ester fibers can exhibit a total biodegradation of at least about 71, 72, 73, 74, 75, 76, 77, 78, 79, 80, 81, 82, 83, 84, 85, 86, 87, or 88 percent, when tested under according to ISO 14855-1 (2012) for a period of 50 days under home composting conditions. This may represent a relative biodegradation of at least about 95, 97, 99, 100, 101, 102, or 103 percent, when compared to cellulose subjected to identical test conditions.

To be considered "biodegradable," under home composting conditions according to the French norm NF T 51-800 and the Australian standard AS 5810, a material must exhibit a biodegradation of at least 90 percent in total (e.g., as compared to the initial sample), or a biodegradation of at least 90 percent of the maximum degradation of a suitable reference material after a plateau has been reached for both the reference and test item. The maximum test duration for biodegradation under home compositing conditions is 1 year. The high concentrated recycle derived cellulose ester fibers as described herein may exhibit a biodegradation of at least 90 percent within not more than 1 year, measured according 14855-1 (2012) under home composting conditions. In some cases, the high concentrated recycle derived cellulose ester fibers may exhibit a biodegradation of at least about 91, 92, 93, 94, 95, 96, 97, 98, 99, or 99.5 percent within not more than 1 year, or the fibers may exhibit 100 percent biodegradation within not more than 1 year, measured according 14855-1 (2012) under home composting conditions.

Additionally, or in the alternative, the fibers described herein may exhibit a biodegradation of at least 90 percent within not more than about 350, 325, 300, 275, 250, 225, 220, 210, 200, 190, 180, 170, 160, 150, 140, 130, 120, 110, 100, 90, 80, 70, 60, or 50 days, measured according 14855-1 (2012) under home composting conditions. In some cases, the fibers can be at least about 97, 98, 99, or 99.5 percent biodegradable within not more than about 70, 65, 60, or 50 days of testing according to ISO 14855-1 (2012) under home composting conditions. As a result, the high concentrated recycle derived cellulose ester fibers may be considered biodegradable according to, for example, French Standard NF T 51-800 and Australian Standard AS 5810 when tested under home composting conditions.

The high concentrated recycle derived cellulose ester fibers can exhibit a biodegradation of at least 60 percent in a period of not more than 45 days, when tested under aerobic composting conditions at a temperature of 58° C. (±2° C.) according to ISO 14855-1 (2012). In some cases, the fibers can exhibit a biodegradation of at least 60 percent in a period of not more than 44, 43, 42, 41, 40, 39, 38, 37, 36, 35, 34, 33, 32, 31, 30, 29, 28, or 27 days when tested under these conditions, also called "industrial composting conditions." These may not be aqueous or anaerobic conditions. In some cases, the fibers can exhibit a total biodegradation of at least about 65, 70, 75, 80, 85, 87, 88, 89, 90, 91, 92, 93, 94, or 95 percent, when tested under according to ISO 14855-1 (2012) for a period of 45 days under industrial composting conditions. This may represent a relative biodegradation of at least about 95, 97, 99, 100, 102, 105, 107, 110, 112, 115, 117, or 119 percent, when compared to cellulose fibers subjected to identical test conditions.

To be considered "biodegradable," under industrial composting conditions according to ASTM D6400 and ISO 17088, at least 90 percent of the organic carbon in the whole item (or for each constituent present in an amount of more than 1% by dry mass) must be converted to carbon dioxide by the end of the test period when compared to the control or in absolute. According to European standard ED 13432 (2000), a material must exhibit a biodegradation of at least 90 percent in total, or a biodegradation of at least 90 percent of the maximum degradation of a suitable reference material after a plateau has been reached for both the reference and test item. The maximum test duration for biodegradability under industrial compositing conditions is 180 days. The high concentrated recycle derived cellulose ester fibers described herein may exhibit a biodegradation of at least 90 percent within not more than 180 days, measured according 14855-1 (2012) under industrial composting conditions. In some cases, the high concentrated recycle derived cellulose ester fibers may exhibit a biodegradation of at least about 91, 92, 93, 94, 95, 96, 97, 98, 99, or 99.5 percent within not more than 180 days, or the fibers may exhibit 100 percent biodegradation within not more than 180 days, measured according 14855-1 (2012) under industrial composting conditions.

Additionally, or in the alternative, high concentrated recycle derived cellulose ester fibers described herein may exhibit a biodegradation of least 90 percent within not more than about 175, 170, 165, 160, 155, 150, 145, 140, 135, 130, 125, 120, 115, 110, 105, 100, 95, 90, 85, 80, 75, 70, 65, 60, 55, 50, or 45 days, measured according 14855-1 (2012) under industrial composting conditions. In some cases, the high concentrated recycle derived cellulose ester fibers can be at least about 97, 98, 99, or 99.5 percent biodegradable within not more than about 65, 60, 55, 50, or 45 days of testing according to ISO 14855-1 (2012) under industrial composting conditions. As a result, the high concentrated recycle derived cellulose ester fibers described herein may be considered biodegradable according ASTM D6400 and ISO 17088 when tested under industrial composting conditions.

The fibers or fibrous articles may exhibit a biodegradation in soil of at least 60 percent within not more than 130 days, measured according to ISO 17556 (2012) under aerobic conditions at ambient temperature. In some cases, the fibers can exhibit a biodegradation of at least 60 percent in a period of not more than 130, 120, 110, 100, 90, 80, or 75 days when tested under these conditions, also called "soil composting conditions." These may not be aqueous or anaerobic conditions. In some cases, the fibers can exhibit a total biodegradation of at least about 65, 70, 72, 75, 77, 80, 82, or 85 percent, when tested under according to ISO 17556 (2012) for a period of 195 days under soil composting conditions. This may represent a relative biodegradation of at least about 70, 75, 80, 85, 90, or 95 percent, when compared to cellulose fibers subjected to identical test conditions.

In order to be considered "biodegradable," under soil composting conditions according the OK biodegradable SOIL conformity mark of Vinçotte and the DIN Geprüft Biodegradable in soil certification scheme of DIN CERTCO, a material must exhibit a biodegradation of at least 90 percent in total (e.g., as compared to the initial sample), or a biodegradation of at least 90 percent of the maximum degradation of a suitable reference material after a plateau has been reached for both the reference and test item. The maximum test duration for biodegradability under soil compositing conditions is 2 years. The high concentrated recycle derived cellulose ester fibers as described herein may exhibit a biodegradation of at least 90 percent within not more than 2 years, 1.75 years, 1 year, 9 months, or 6 months measured according ISO 17556 (2012) under soil composting conditions. In some cases, the high concentrated recycle derived cellulose ester fibers may exhibit a biodegradation of at least about 91, 92, 93, 94, 95, 96, 97, 98, 99, or 99.5 percent within not more than 2 years, or the fibers may exhibit 100 percent biodegradation within not more than 2 years, measured according ISO 17556 (2012) under soil composting conditions.

Additionally, or in the alternative, high concentrated recycle derived cellulose ester fibers described herein may exhibit a biodegradation of at least 90 percent within not more than about 700, 650, 600, 550, 500, 450, 400, 350, 300, 275, 250, 240, 230, 220, 210, 200, or 195 days, measured according 17556 (2012) under soil composting conditions. In some cases, the high concentrated recycle derived cellulose ester fibers can be at least about 97, 98, 99, or 99.5 percent biodegradable within not more than about 225, 220, 215, 210, 205, 200, or 195 days of testing according to ISO 17556 (2012) under soil composting conditions. As a result, the high concentrated recycle derived cellulose ester fibers described herein may meet the requirements to receive The OK biodegradable SOIL conformity mark of Vinçotte and to meet the standards of the DIN Geprüft Biodegradable in soil certification scheme of DIN CERTCO.

In some embodiments, high concentrated recycle derived cellulose ester fibers (or fibrous articles) of the present invention may include less than 1, 0.75, 0.50, or 0.25 weight percent of components of unknown biodegradability. In some cases, the fibers or fibrous articles described herein may include no components of unknown biodegradability.

In addition to being biodegradable under industrial and/or home composting conditions, high concentrated recycle derived cellulose ester fibers or fibrous articles as described herein may also be compostable under home and/or industrial conditions. As described previously, a material is considered compostable if it meets or exceeds the requirements set forth in EN 13432 for biodegradability, ability to disintegrate, heavy metal content, and ecotoxicity. The high concentrated recycle derived cellulose ester fibers or fibrous articles described herein may exhibit sufficient compostability under home and/or industrial composting conditions to meet the requirements to receive the OK compost and OK compost HOME conformity marks from Vinçotte.

In some cases, the high concentrated recycle derived cellulose ester and fibers and fibrous articles described herein may have a volatile solids concentration, heavy metals and fluorine content that fulfill all of the requirements laid out by EN 13432 (2000). Additionally, the high concentrated recycle derived cellulose ester fibers may not cause a negative effect on compost quality (including chemical parameters and ecotoxicity tests).

In some cases, the high concentrated recycle derived cellulose ester fibers or fibrous articles can exhibit a disintegration of at least 90 percent within not more than 26 weeks, measured according to ISO 16929 (2013) under industrial composting conditions. In some cases, the fibers or fibrous articles may exhibit a disintegration of at least about 91, 92, 93, 94, 95, 96, 97, 98, 99, or 99.5 percent under industrial composting conditions within not more than 26 weeks, or the fibers or articles may be 100 percent disintegrated under industrial composting conditions within not more than 26 weeks. Alternatively, or in addition, the fibers or articles may exhibit a disintegration of at least 90 percent under industrial composting conditions within not more than about 26, 25, 24, 23, 22, 21, 20, 19, 18, 17, 16, 15, 14, 13, 12, 11, or 10 weeks, measured according to ISO 16929 (2013). In some cases, the high concentrated recycle derived cellulose ester fibers or fibrous articles described herein may be at least 97, 98, 99, or 99.5 percent disintegrated within not more than 12, 11, 10, 9, or 8 weeks under industrial composting conditions, measured according to ISO 16929 (2013).

In some cases, the high concentrated recycle derived cellulose ester fibers or fibrous articles can exhibit a disintegration of at least 90 percent within not more than 26 weeks, measured according to ISO 16929 (2013) under home composting conditions. In some cases, the fibers or fibrous articles may exhibit a disintegration of at least about 91, 92, 93, 94, 95, 96, 97, 98, 99, or 99.5 percent under home composting conditions within not more than 26 weeks, or the fibers or articles may be 100 percent disintegrated under home composting conditions within not more than 26 weeks. Alternatively, or in addition, the fibers or articles may exhibit a disintegration of at least 90 percent within not more than about 26, 25, 24, 23, 22, 21, 20, 19, 18, 17, 16, or 15 weeks under home composting conditions, measured according to ISO 16929 (2013). In some cases, the high concentrated recycle derived cellulose ester fibers or fibrous articles described herein may be at least 97, 98, 99, or 99.5 percent disintegrated within not more than 20, 19, 18, 17, 16, 15, 14, 13, or 12 weeks, measured under home composting conditions according to ISO 16929 (2013).

In embodiments, cellulose acetate fibers are provided that comprise high concentrated recycle derived content and are biodegradable and/or compostable. It is believed that the cellulose acetate fibers can achieve higher levels of biodegradability and/or compostability without use of additives that have traditionally been used to facilitate environmental non-persistence of similar fibers. Such additives can include, for example, photodegradation agents, biodegradation agents, decomposition accelerating agents, and various types of other additives. Despite being substantially free of these types of additives, in embodiments, the cellulose acetate fibers and articles can be provided that exhibit enhanced biodegradability and compostability when tested under industrial, home, and/or soil conditions, as discussed herein.

In some embodiments, the cellulose acetate fibers described herein may be substantially free of photodegradation agents. For example, the fibers may include not more than about 1, 0.75, 0.50, 0.25, 0.10, 0.05, 0.025, 0.01, 0.005, 0.0025, or 0.001 weight percent of photodegradation agent, based on the total weight of the fiber, or the fibers may include no photodegradation agents. Examples of such photodegradation agents include, but are not limited to, pigments which act as photooxidation catalysts and are optionally augmented by the presence of one or more metal salts, oxidizable promoters, and combinations thereof. Pigments can include coated or uncoated anatase or rutile titanium dioxide, which may be present alone or in combination with one or more of the augmenting components such as, for example, various types of metals. Other examples of photodegradation agents include benzoins, benzoin alkyl ethers, benzophenone and its derivatives, acetophenone and its derivatives, quinones, thioxanthones, phthalocyanine and other photosensitizers, ethylene-carbon monoxide copolymer, aromatic ketone-metal salt sensitizers, and combinations thereof.

In some embodiments, the cellulose acetate fibers described herein may be substantially free of biodegradation agents and/or decomposition agents. For example, the fibers may include not more than about 1, 0.75, 0.50, 0.25, 0.10, 0.05, 0.025, 0.01, 0.005, 0.0025, 0.0020, 0.0015, 0.001, 0.0005 weight percent of biodegradation agents and/or decomposition agents, based on the total weight of the fiber, or the fibers may include no biodegradation and/or decomposition agents. Examples of such biodegradation and decomposition agents include, but are not limited to, salts of oxygen acid of phosphorus, esters of oxygen acid of phosphorus or salts thereof, carbonic acids or salts thereof, oxygen acids of phosphorus, oxygen acids of sulfur, oxygen acids of nitrogen, partial esters or hydrogen salts of these oxygen acids, carbonic acid and its hydrogen salt, sulfonic acids, and carboxylic acids.

Other examples of such biodegradation and decomposition agents include an organic acid selected from the group consisting of oxo acids having 2 to 6 carbon atoms per molecule, saturated dicarboxylic acids having 2 to 6 carbon atoms per molecule, and lower alkyl esters of the oxo acids or the saturated dicarboxylic acids with alcohols having from 1 to 4 carbon atoms. Biodegradation agents may also comprise enzymes such as, for example, a lipase, a cellulase, an esterase, and combinations thereof. Other types of biodegradation and decomposition agents can include cellulose phosphate, starch phosphate, calcium secondary phosphate, calcium tertiary phosphate, calcium phosphate hydroxide, glycolic acid, lactic acid, citric acid, tartaric acid, malic acid, oxalic acid, malonic acid, succinic acid, succinic anhydride, glutaric acid, acetic acid, and combinations thereof.

Cellulose acetate fibers described herein may also be substantially free of several other types of additives that have been added to other fibers to encourage environmental non-persistence. Examples of these additives can include, but are not limited to, polyesters, including aliphatic and low molecular weight (e.g., less than 5000) polyesters, enzymes, microorganisms, water soluble polymers, modified cellulose acetate, water-dispersible additives, nitrogen-containing compounds, hydroxy-functional compounds, oxygen-containing heterocyclic compounds, sulfur-containing heterocyclic compounds, anhydrides, monoepoxides, and combinations thereof. In some cases, the fibers described herein may include not more than about 0.5, 0.4, 0.3, 0.25, 0.1, 0.075, 0.05, 0.025, 0.01, 0.0075, 0.005, 0.0025, or 0.001 weight percent of these types of additives, or the cellulose acetate fibers may not include any of these types of additives.

In embodiments, durable articles are provided that comprise the high concentrated recycle derived cellulose esters, as described herein. In embodiments, the durable articles are made from moldable thermoplastic material comprising the high concentrated recycle derived cellulose esters, as described herein. In embodiments, the moldable thermoplastic material comprises high concentrated recycle derived cellulose esters chosen from cellulose acetate propionate, cellulose acetate butyrate, or combinations thereof.

In embodiments, an integrated process for preparing a high concentrated recycle derived cellulose ester is provide which comprises the processing steps of: (1) preparing a high concentrated recycle derived syngas obtained by gasifying a solid fossil fuel source and high concentrated recycle polymer; (2) preparing at least one high concentrated recycle derived chemical intermediate from said high concentrated recycle derived syngas; (3) reacting said high concentrated recycle derived chemical intermediate in a reaction scheme to prepare at least one high concentrated recycle derived cellulose reactant for preparing a high concentrated recycle derived cellulose ester, and/or selecting said high concentrated recycle derived chemical intermediate to be at least one high concentrated recycle derived cellulose reactant for preparing a high concentrated recycle derived cellulose ester; and (4) reacting said at least one high concentrated recycle derived cellulose reactant to prepare said high concentrated recycle derived cellulose ester; wherein said high concentrated recycle derived cellulose ester comprises at least one substituent on an anhydroglucose unit (AGU) derived from high concentrated recycle derived syngas.

In embodiments, the processing steps (1) to (4) are carried out in a system that is in fluid and/or gaseous communication (i.e., including the possibility of a combination of fluid and gaseous communication). It should be understood that the high concentrated recycle derived chemical intermediates, in one or more of the reaction schemes for producing high concentrated recycle derived cellulose esters starting from high concentrated recycle derived syngas, may be temporarily stored in storage vessels and later reintroduced to the integrated process system, or at time are sealed off through valves, and are nevertheless considered to be in fluid communication upstream and downstream. Further, the entire process need not be in gaseous and/or fluid communication simultaneously to be considered in gaseous communication provided that piping can be traced from one vessel to another to close the loop.

In embodiments, the at least one high concentrated recycle derived chemical intermediate is chosen from methanol, methyl acetate, acetic anhydride, acetic acid, or combinations thereof. In embodiments, one high concentrated recycle derived chemical intermediate is methanol, and the methanol is used in a reaction scheme to make a second high concentrated recycle derived chemical intermediate that is acetic anhydride. In embodiments, the high concentrated recycle derived cellulose reactant is acetic anhydride.

Unless otherwise stated, reference to the weight of the feedstock composition or stream includes all solids, and if present liquids, fed to the gasifier, and unless otherwise stated, does not include the weight of any gases in the feedstock composition as fed to the injector or gasifier. A composition or a stream are used interchangeably.

The phrase "at least a portion" includes at least a portion and up to and including the entire amount or time period.

The phrase "textiles and/or plastics" means textiles and/or plastics in any form, size, or shape, including their shape and size as articles, size reduced, or densified whether as agglomerates or extrudates. The textiles and/or plastics can include only textiles, only plastics, or a mix of textiles and plastics. The phrase "textiles and/or plastics" provides support for stating or claiming that the textiles and/or plastics can be size reduced, or aggregated, or densified, or agglomerated, or extruded or pelletized.

The phrase "textiles and/or plastics" when used in conjunction with an amount means the cumulative amount of the textiles and plastics to the extent that either are present. For example, textiles or plastics in an amount of at least 15% means that, if textiles and plastics are used, the cumulative amount is at least 15%, and if only textiles are used then the textiles are in an amount of at least 15%, and if only plastics are used then the plastics are in an amount of at least 15%.

In embodiments, textile and/or plastic aggregates employed in the feedstock stream to the gasifier are solid at 25° C. at 1 atm. The textile and/or plastic aggregates are a collection of particles, briquettes, agglomerates, pellets, or rods, or any other shape or size that different from the native shape of the textile from which the aggregate is made. Textile and/or plastic aggregates can be merely size reduced textile and/or plastics, or they can be densified textile and/or plastics. The densified textile and/or plastic aggregates can be agglomerates, or they can be extrudates or pellets.

A feedstock stream or composition is used interchangeably with a fossil fuel feedstock stream or composition and contains at least a fossil fuel in the form or a solid or liquid, and a recycle plastic. When weight percentages are express based on the feedstock stream or fuel feedstock, they exclude the oxidant.

A PIA or PIA reactant or composition or compound is associated with, or originates from, a recycle textile, size reduced textiles, densified textiles, a recycle plastic, size reduced plastics, densified plastics, or a recycle derived syngas if any one of them are subjected to partial oxidation gasification, regardless of when the allotment is taken, realized, or consumed. For example, a PIA can be associated with a densified textile and/or plastic that is gasified even though the allotment is taken and deposited into a recycle inventory or transferred to a PIA when recycle textiles and/or plastics are received or possessed or owned by a syngas manufacturer and even though the densified textile and/or plastic is not gasified at the time the allotment is taken. Further, an allotment that is associated with or originates from gasifying a densified textile and/or plastic does not limit the timing of taking or recognizing the allotment or depositing the allotment into a recycle inventory. An allotment taken when a recycle polymer (textile and/or plastic, size reduced textile and/or plastic, or densified textile and/or plastic) is owned, possessed, or receiving by a syngas manufacturer and deposited into a recycle inventory is an allotment that is associated with or originates from gasifying a densified textile and/or plastic even though, at the time of taking or depositing the allotment, the densified textile and/or plastic has not yet been gasified.

As used throughout, the phrase "originates" or "origin" is synonymous to "associated with."

For purposes of classifying materials in the feedstock stream or composition, a solid fossil fuel used can be coal, petcoke, or any other solid at 25° C. and 1 atmosphere that is a byproduct from refining oil or petroleum. The fossil fuel portion of the feedstock composition is to be distinguished from recycle plastics, even if the recycle plastics are carbonaceous and in part derived from raw materials obtained from refining crude oil. A fossil fuel can include liquid fossil fuels, such as liquid hydrocarbons or streams obtained from refining crude oil, or waste streams from chemical synthetic processes.

There is provided a process for the production of a high concentrated recycle polymer derived syngas to make at least one chemical comprising campaigning the production of a syngas from a single gasifier between a first feedstock to produce a first syngas for a first period of time, and transitioning to a second feedstock to produce a second syngas for a second period of time, wherein the first feedstock comprises a solid fossil fuel or a liquid hydrocarbon fuel and said second feedstock comprises recycle polymer (e.g. textiles and/or plastics) in an amount that is higher than the amount, if any, used in the first feedstock, and the gasifier is operated at a lower gasification temperature during at least a portion of the second time period than the gasification temperature in the first time period, and the second syngas is the high concentration recycle polymer derived syngas.

Generally, in a synthesis gas operation one or more feedstock composition(s) comprised of fossil fuel sources (e.g. coal, petcoke, liquid hydrocarbons) and textile and/or plastic aggregates as an individual stream or combined with the fossil fuel source streams, and optionally water and other chemical additives, are fed or injected along with an oxidizer gas into a gasification reaction zone or chamber of a synthesis gas generator (gasifier) and gasified in the presence of an oxidizer such as oxygen, also fed to the gasifier. A hot gas stream is produced in the gasification zone, optionally refractory lined, at high temperature and high pressure generating a molten slag, soot, ash and gases including hydrogen, carbon monoxide, carbon dioxide and can include other gases such as methane, hydrogen sulfide and nitrogen depending on the fuel source and reaction conditions. The hot gas stream is produced in the reaction zone is cooled using a syngas cooler or in a quench water bath at the base of the gasifier which also solidifies ash and slag and separates solids from the gases. The quench water bath also acts as a seal to maintain the internal temperature and pressure in the gasifier while the slag, soot and ash are removed into a lock hopper. The cooled product gas stream removed from the gasifier (the raw syngas stream) can be further treated with water to remove remaining solids such as soot, and then further treated to remove acid gas (e.g. hydrogen sulfide) after optionally further cooling and shifting the ratio of carbon monoxide to hydrogen.

In embodiments, the textiles and/or plastics employed in the feedstock stream to the gasifier are solid when measured at 25° C. at 1 atm. In embodiments, the textiles and/or plastics are textile and/or plastic aggregates. Textile and/or plastic aggregates are a collection of particles, briquettes, rods, shredded pieces, or any other shape or size that different from the native shape of the textile and/or plastic from which the textile and/or plastic aggregates is made. Textile and/or plastic aggregates can be merely loose size reduced textile and/or plastics, or they can be densified textiles and/or plastics. The densified textile and/or plastic aggregates can be agglomerates, or they can be extruded or pellets.

Textiles as used herein are natural and/or synthetic fibers, rovings, yarns, nonwoven webs, cloth, fabrics and products made from or containing any of the aforementioned items, provided that the textiles are either post-consumer or post-industrial textiles. Textiles can be woven, knitted, knotted, stitched, tufted, pressing of fibers together such as would be done in a felting operation, embroidered, laced, crocheted, braided, or nonwoven webs and materials. Textiles as used herein include fabrics, and fibers separated from a textile or other product containing fibers, scrap or off spec fibers or yarns or fabrics, or any other source of loose fibers and yarns. A textile also includes staple fibers, continuous fibers, threads, tow bands, twisted and/or spun yarns, grey fabrics made from yarns, finished fabrics produced by wet processing gray fabrics, and garments made from the finished fabrics or any other fabrics. Textiles include apparels, interior furnishings, and industrial types of textiles. Textiles also include post-industrial textiles or post-consumer textiles or both.

Examples of textiles in the apparel category (things humans wear or made for the body) include sports coats, suits, trousers and casual or work pants, shirts, socks, sportswear, dresses, intimate apparel, outerwear such as rain jackets, cold temperature jackets and coats, sweaters, protective clothing, uniforms, and accessories such as scarves, hats, and gloves. Examples of textiles in the interior furnishing category include furniture upholstery and slipcovers, carpets and rugs, curtains, bedding such as sheets, pillow covers, duvets, comforters, mattress covers; linens, tablecloths, towels, washcloths, and blankets. Examples of industrial textiles include transportation (auto, airplanes, trains, buses) seats, floor mats, trunk liners, and headliners; outdoor furniture and cushions, tents, backpacks, luggage, ropes, conveyor belts, calendar roll felts, polishing cloths, rags, soil erosion fabrics and geotextiles, agricultural mats and screens, personal protective equipment, bullet proof vests, medical bandages, sutures, tapes, and the like.

The nonwoven webs that are classified as textiles do not include the category of wet laid nonwoven webs and articles made therefrom. While a variety of articles having the same function can be made from a dry or wet laid process, the article made from the dry laid nonwoven web is classified as a textile. Examples of suitable articles that may be formed from dry laid nonwoven webs as described herein can include those for personal, consumer, industrial, food service, medical, and other types of end uses. Specific examples can include, but are not limited to, baby wipes, flushable wipes, disposable diapers, training pants, feminine hygiene products such as sanitary napkins and tampons, adult incontinence pads, underwear, or briefs, and pet training pads. Other examples include a variety of different dry or wet wipes, including those for consumer (such as personal care or household) and industrial (such as food service, health care, or specialty) use. Nonwoven webs can also be used as padding for pillows, mattresses, and upholstery, batting for quilts and comforters. In the medical and industrial fields, nonwoven webs of the present invention may be used for medical and industrial face masks, protective clothing, caps, and shoe covers, disposable sheets, surgical gowns, drapes, bandages, and medical dressings. Additionally, nonwoven webs as described herein may be used for environmental fabrics such as geotextiles and tarps, oil and chemical absorbent pads, as well as building materials such as acoustic or thermal insulation, tents, lumber and soil covers and sheeting. Nonwoven webs may also be used for other consumer end use applications, such as for, carpet backing, packaging for consumer, industrial, and agricultural goods, thermal or acoustic insulation, and in various types of apparel. The dry laid nonwoven webs as described herein may also be used for a variety of filtration applications, including transportation (e.g., automotive or aeronautical), commercial, residential, industrial, or other specialty applications. Examples can include filter elements for consumer or industrial air or liquid filters (e.g., gasoline, oil, water), including nanofiber webs used for microfiltration, as well as end uses like tea bags, coffee filters, and dryer sheets. Further, nonwoven webs as described herein may be used to form a variety of components for use in automobiles, including, but not limited to, brake pads, trunk liners, carpet tufting, and under padding.

The textiles can include single type or multiple type of natural fibers and/or single type or multiple type of synthetic fibers. Examples of textile fiber combinations include all natural, all synthetic, two or more type of natural fibers, two or more types of synthetic fibers, one type of natural fiber and one type of synthetic fiber, one type of natural fibers and two or more types of synthetic fibers, two or more types of natural fibers and one type of synthetic fibers, and two or more types of natural fibers and two or more types of synthetic fibers.

Polymers used to make the synthetic fibers can be thermoplastic or thermosetting polymers. The polymer number average molecular weight can be at least 300, or at least 500, or at least 1000, or at least 5,000, or at least 10,000, or at least 20,000, or at least 30,000, or at least 50,000 or at least 70,000 or at least 90,000 or at least 100,000 or at least 130,000. The weight average molecular weight of the polymers can be at least 300, or at least 500, or at least 1000, or at least 5,000, or at least 10,000, or at least 20,000, or at least 30,000, or at least 50,000, or at least 70,000, or at least 90,000, or at least 100,000, or at least 130,000, or at least 150,000, or at least 300,000.

Natural fibers include those that are plant derived or animal derived. Natural fibers can be cellulosics, hemicellulosics, and lignins. Examples of plant derived natural fibers include hardwood pulp, softwood pulp, and wood flour; and other plant fibers including those in wheat straw, rice straw, abaca, coir, cotton, flax, hemp, jute, bagasse, kapok, papyrus, ramie, rattan, vine, kenaf, abaca, henequen, sisal, soy, cereal straw, bamboo, reeds, esparto grass, bagasse, Sabai grass, milkweed floss fibers, pineapple leaf fibers, switch grass, lignin-containing plants, and the like. Examples of animal derived fibers include wool, silk, mohair, cashmere, goat hair, horsehair, avian fibers, camel hair, angora wool, and alpaca wool.

Synthetic fibers are those fibers that are, at least in part, synthesized or derivatized through chemical reactions, or regenerated, and include, but are not limited to, rayon, viscose, mercerized fibers or other types of regenerated cellulose (conversion of natural cellulose to a soluble cellulosic derivative and subsequent regeneration) such as lyocell (also known as Tencel), Cupro, Modal, acetates such as polyvinylacetate, polyamides including nylon, polyesters such as those polyethylene terephthalate (PET), copolyesters including those made with IPA, CHDM and/or 2,2,4,4-tetramethyl-1,3-cyclobutanediol, polycyclohexylenedimethylene terephthalate (PCT) and other copolymers, olefinic polymers such as polypropylene and polyethylene, polycarbonates, poly sulfates, poly sulfones, polyethers such as polyether-urea known as Spandex or elastane, polyacrylates, acrylonitrile copolymers, polyvinylchloride (PVC), polylactic acid, polyglycolic acid, sulfopolyester fibers, and combinations thereof.

The textiles and/or plastics are post-consumer and/or post-industrial (also known as pre-consumer) textiles and/or plastics. Post-consumer textiles and/or plastics are those that have been used at least once for its intended application for any duration of time regardless of wear. Post-industrial size reduced textiles and/or plastics include rework, regrind, scrap, trim, out of specification textiles and/or plastics that have not been used for their intended application, or any textiles and/or plastics that have not been used by the end consumer.

The plastics are made from polymers that can be thermoplastic or thermosetting polymers. The polymer number average molecular weight can be at least 300, or at least 500, or at least 1000, or at least 5,000, or at least 10,000, or at least 20,000, or at least 30,000, or at least 50,000 or at least 70,000 or at least 90,000 or at least 100,000 or at least 130,000. The weight average molecular weight of the polymers can be at least 300, or at least 500, or at least 1000, or at least 5,000, or at least 10,000, or at least 20,000, or at least 30,000, or at least 50,000, or at least 70,000, or at least 90,000, or at least 100,000, or at least 130,000, or at least 150,000, or at least 300,000.

Examples of plastics (i.e. organic synthetic polymers that are solid at 25° C. at 1 atm) include acrylobutadienestyrene (ABS), cellulosics such as cellulose acetate, cellulose diacetate, cellulose triacetate, cellulose acetate propionate, cellulose acetate butyrate, and regenerated cellulose; epoxy, polyamides, phenolic resins, polyacetal, polycarbonates, polyesters including PET (polyethylene terephthalate) and copolyesters such as those containing residues of TMCD (2,2,4,4-tetramethyl-1,3-cyclobutanediol), CHDM (cyclohexanedimethanol), propylene glycol, or NPG (neopentylglycol) monomers, high density polyethylene, low density polyethylene, crosslinked polyethylene, polyphenylene-based alloys, polypropylene and copolymers thereof, other polyolefins, polystyrene, poly(methyl methacrylate), polytetrafluoroethylene, styrenic containing polymers, polyurethane, vinyl-based polymers, styrene acrylonitrile, thermoplastic elastomers other than tires which include thermoplastic elastomers, epoxy, and urea containing polymers and melamines.

In embodiments, the first and/or second feedstocks contain thermosetting polymers. Examples of the amounts of thermosetting polymers present in the first and/or second feedstocks can be at least 5 wt. %, or at least 10 wt. %, or at least 15 wt. %, or at least 20 wt. %, or at least 25 wt. %, or at least 30 wt. %, or at least 40 wt. %, or at least 50 wt. %, or at least 60 wt. %, or at least 70 wt. %, or at least 80 wt. %, or at least 90 wt. %, or at least 95 wt. %, or at least 97 wt. %, or at least 98 wt. %, or 100 wt. %, based on the weight of all plastics in the respective feedstock to the gasifier.

Examples of families of articles containing one or more of the above polymers that can be size reduced through granulation or pulverization, or can be first densified followed by size reduction of the densified material, fed to the gasifier include packaging, engineering plastics, building and construction articles, household and houseware articles, furniture, lawn and garden, and automotive plastics. Examples of types of articles include bottles (for all types of applications such as beverage, food, detergents, cosmetics, personal care, etc.), bottle caps, cigarette filters and rods, eyeglass frames, cups, lids, trays, plumbing pipes (e.g. PBT, PVC, and PEX pipes), cable insulations, sheets, carrier bags, automotive moldings, bedding, seat cushions, seat covers, beverage machine fronts, fuel tanks, acrylic sheeting, buckets, audio tape, plumbing pipes, septic tanks, toys, cling film, agricultural film, milk carton coatings, electrical cable coating, heavy duty industrial bags, sound insulation, helmets, surf boards, stretch film, industrial packaging film, thin-walled containers, crates and boxes, and industrial wrapping and film, packaging made from flashspun high density polyethylene such as used for envelopes or medical packaging or house wrap, building insulation, diapers, sports equipment, eyeglass lenses, CD's and DVD's, food packaging, microwave-proof containers, garden furniture, medical packaging and appliances, luggage, and kitchen appliances.

Any of plastics used to make a feedstock to the gasifier can be formulated with the additives and fillers that include plasticizers, waxes, compatibilizers, biodegradation promoters, dyes, pigments, colorants, luster control agents, lubricants, anti-oxidants, viscosity modifiers, antifungal agents, anti-fogging agents, heat stabilizers, impact modifiers, flame retardants, corrosion inhibitors, antibacterial agents, softening agents, fragrances, and mold release agents.

The plasticizer reduces the melt temperature, the $T_g$, and/or the melt viscosity of the polymer used to make the plastic articles. Examples of plasticizers include phosphate plasticizers, benzoate plasticizers, adipate plasticizer, phthalate plasticizer, a glycolic acid ester, a citric acid ester plasticizer and a hydroxyl-functional plasticizer. More specifically, examples of plasticizers include triphenyl phosphate, tricresyl phosphate, cresyldiphenyl phosphate, octyldiphenyl phosphate, diphenylbiphenyl phosphate, trioctyl phosphate, tributyl phosphate, diethyl phthalate, dimethoxyethyl phthalate, dimethyl phthalate, dioctyl phthalate, dibutyl phthalate, di-2-ethylhexyl phthalate, butylbenzyl phthalate, dibenzyl phthalate, butyl phthalyl butyl glycolate, ethyl phthalyl ethyl glycolate, methyl phthalyl ethyl glycolate, triethyl citrate, tri-n-butyl citrate, acetyltriethyl citrate, acetyl-tri-n-butyl citrate, and acetyl-tri-n-(2-ethylhexyl) citrate, triacetin (glycerol triacetate), diethylene glycol diacetate, triethylene glycol diacetate, and tripropionin, diethylene glycol dibenzoate, rosin, hydrogenated rosin, stabilized rosin, and their monofunctional alcohol esters or polyol esters; a modified rosin including, but not limited to, maleic- and phenol-modified rosins and their esters; terpene resins; phenol-modified terpene resins; coumarin-indene resins; phenolic resins; alkylphenol-acetylene resins; and phenol-formaldehyde resins.

Some examples of plasticizers are those that are biodegradable. Examples of these plasticizers include triacetin, triethyl citrate, acetyl triethyl citrate, polyethylene glycol, the benzoate containing plasticizers such as the Benzoflex™ plasticizer series, poly (alkyl succinates) such as poly (butyl succinate), polyethersulfones, adipate based plasticizers, soybean oil epoxides such as the Paraplex™ plasticizer series, sucrose based plasticizers, dibutyl sebacate, tributyrin, sucrose acetate isobutyrate, the Resolflex™ series of plasticizers, triphenyl phosphate, glycolates, 2,2,4-trimethylpentane-1,3-diyl bis(2-methylpropanoate), and polycaprolactones.

The amount of plasticizer in the polymer used to make the plastic articles can range from about 0.5 to about 50 weight percent based on the weight of the polymer. Other ranges can be from about 5 to about 35 weight percent based on the weight of the polymer, from about 5 to about 30, and from about 10 to about 20.

Waxes have also been used to increase firmness. See, for example, U.S. Pat. No. 2,904,050, incorporated herein by reference.

The compatibilizer can be either a non-reactive compatibilizer or a reactive compatibilizer. The compatibilizer can enhance the ability of the first polymer to reach a desired small particle size to improve the dispersion of the first polymer into a second polymer, such as into an elastomer. The compatibilizers used can also improve mechanical and physical properties of the elastomeric composition compositions by improving the interfacial interaction/bonding between a first polymer and an elastomer or a second polymer.

The amount of compatibilizer in the polymer can range from about 1 wt. % to about 40 wt. %, from about 5 wt. % to about 20 wt. %, or about 10 to about 20 wt. % based on the weight of the polymer.

If desired, biodegradation and decomposition agents, e.g. hydrolysis assistant or any intentional degradation promoter additives can be added to or contained in the polymer, added either during manufacture of the polymer or subsequent to its manufacture and melt or solvent blended together. Those additives can promote hydrolysis by releasing acidic or basic residues, and/or accelerate photo (UV) or oxidative degradation and/or promote the growth of selective microbial colony to aid the disintegration and biodegradation in compost and soil medium. In addition to promoting the degradation, these additives can have an additional function such as improving the processability of the article or improving mechanical properties.

One set of examples of decomposition agents include inorganic carbonate, synthetic carbonate, nepheline syenite, talc, magnesium hydroxide, aluminum hydroxide, diatomaceous earth, natural or synthetic silica, calcined clay, and the like. If used, it is desirable that these fillers are dispersed well in the polymer matrix. The fillers can be used singly, or in a combination of two or more.

Another set of examples is aromatic ketones used as an oxidative decomposition agent, including benzophenone, anthraquinone, anthrone, acetylbenzophenone, 4-octylbenzophenone, and the like. These aromatic ketones may be used singly, or in a combination of two or more.

Other examples include transition metal compounds used as oxidative decomposition agents, such as salts of cobalt or magnesium, preferably aliphatic carboxylic acid (C12 to C20) salts of cobalt or magnesium, and more preferably cobalt stearate, cobalt oleate, magnesium stearate, and magnesium oleate; or anatase-form titanium dioxide, or titanium dioxide may be used. Mixed phase titanium dioxide particles may be used in which both rutile and anatase crystalline structures are present in the same particle. The particles of photoactive agent can have a relatively high surface area, for example from about 10 to about 300 sq. m/g, or from 20 to 200 sq. m/g, as measured by the BET surface area method. The photoactive agent can be added to the plasticizer if desired. These transition metal compounds can be used singly, or in a combination of two or more.

Examples of rare earth compounds used as an oxidative decomposition agent include rare earths belonging to periodic table Group 3A, and oxides thereof. Specific examples thereof include cerium (Ce), yttrium (Y), neodymium (Nd), rare earth oxides, hydroxides, rare earth sulfates, rare earth nitrates, rare earth acetates, rare earth chlorides, rare earth carboxylates, and the like. More specific examples thereof include cerium oxide, ceric sulfate, ceric ammonium Sulfate, ceric ammonium nitrate, cerium acetate, lanthanum nitrate, cerium chloride, cerium nitrate, cerium hydroxide, cerium octylate, lanthanum oxide, yttrium oxide, Scandium oxide, and the like. These rare earth compounds may be used singly, or in a combination of two or more.

Examples of basic additives used as an oxidative decomposition agent include alkaline earth metal oxides, alkaline earth metal hydroxides, alkaline earth metal carbonates, alkali metal carbonates, alkali metal bicarbonates, $ZηO$ and basic Al2O3. At least one basic additive can be MgO, Mg(OH)2, MgCO3, CaO, Ca(OH)2, CaCO3, NaHCO3, Na2CO3, K2CO3, ZrηO KHCO3 or basic Al2O3. In one aspect, alkaline earth metal oxides, $ZηO$ and basic A12O3 can be used as a basic additive.

Examples of organic acid additives used as an oxidative decomposition agents include acetic acid, propionic acid, butyric acid, valeric acid, citric acid, tartaric acid, oxalic acid, malic acid, benzoic acid, formate, acetate, propionate, butyrate, valerate citrate, tartarate, oxalate, malate, maleic acid, maleate, phthalic acid, phthalate, benzoate, and combinations thereof.

Examples of other hydrophilic polymer or biodegradation promoter may include glycols, polyethers, and polyalcohols or other biodegradable polymers such as poly(glycolic acid), poly(lactic acid), polydioxanes, polyoxalates, poly(α-esters), polycarbonates, polyanhydrides, polyacetals, polycaprolactones, poly(orthoesters), polyamino acids, aliphatic polyesters such as poly(butylene)succinate, poly(ethylene) succinate, starch, regenerated cellulose, or aliphatic-aromatic polyesters such as PBAT.

Colorants can include carbon black, iron oxides such as red or blue iron oxides, titanium dioxide, silicon dioxide, cadmium red, calcium carbonate, kaolin clay, aluminum hydroxide, barium sulfate, zinc oxide, aluminum oxide, and organic pigments such as azo and disazo and triazo pigments, condensed azo, azo lakes, naphthol pigments, anthrapyrimidine, benzimidazolone, carbazole, diketopyrrolopyrrole, flavanthrone, indigoid pigments, isoindolinone, isoindoline, isoviolanthrone, metal complex pigments, oxazine, perylene, perinone, pyranthrone, pyrazoloquinazolone, quinophthalone, triarylcarbonium pigments, triphendioxazine, xanthene, thioindigo, indanthrone, isoindanthrone, anthanthrone, anthraquinone, isodibenzanthrone, triphendioxazine, quinacridone and phthalocyanine series, especially copper phthalocyanme and its nuclear halogenated derivatives, and also lakes of acid, basic and mordant dyes, and isoindolinone pigments, as well as plant and vegetable dyes, and any other available colorant or dye.

Luster control agents for adjusting the glossiness and fillers include silica, talc, clay, barium sulfate, barium carbonate, calcium sulfate, calcium carbonate, magnesium carbonate, and the like.

Suitable flame retardants include silica, metal oxides, phosphates, catechol phosphates, resorcinol phosphates, borates, inorganic hydrates, and aromatic polyhalides.

Antifungal and/or antibacterial agents include polyene antifungals (e.g., natamycin, rimocidin, filipin, nystatin, amphotericin B, candicin, and hamycin), imidazole antifungals such as miconazole (available as MICATIN® from WellSpring Pharmaceutical Corporation), ketoconazole (commercially available as NIZORAL® from McNeil consumer Healthcare), clotrimazole (commercially available as LOTRAMIN® and LOTRAMIN AF® available from Merck and CANESTEN® available from Bayer), econazole, omoconazole, bifonazole, butoconazole, fenticonazole, isoconazole, oxiconazole, sertaconazole (commercially available as ERTACZO® from OrthoDematologics), sulconazole, and tioconazole; triazole antifungals such as fluconazole, itraconazole, isavuconazole, ravuconazole, posaconazole, voriconazole, terconazole, and albaconazole), thiazole antifungals (e.g., abafungin), allylamine antifungals (e.g., terbinafine (commercially available as LAMISIL® from Novartis Consumer Health, Inc.), naftifine (commercially available as NAFTIN® available from Merz Pharmaceuticals), and butenafine (commercially available as LOTRAMIN ULTRA® from Merck), echinocandin antifungals (e.g., anidulafungin, caspofungin, and micafungin), polygodial, benzoic acid, ciclopirox, tolnaftate (e.g., commercially available as TINACTIN® from MDS Consumer Care, Inc.), undecylenic acid, flucytosine, 5-fluorocytosine, griseofulvin, haloprogin, caprylic acid, and any combination thereof.

Viscosity modifiers in modifying the melt flow index or viscosity of the polymer, and include polyethylene glycols and polypropylene glycols, and glycerin.

Fragrances can be added if desired. Examples of fragrances include spices, spice extracts, herb extracts, essential oils, smelling salts, volatile organic compounds, volatile small molecules, methyl formate, methyl acetate, methyl butyrate, ethyl acetate, ethyl butyrate, isoamyl acetate, pentyl butyrate, pentyl pentanoate, octyl acetate, myrcene, geraniol, nerol, citral, citronellal, citronellol, linalool, nerolidol, limonene, camphor, terpineol, alpha-ionone, thujone, benzaldehyde, eugenol, isoeugenol, cinnamaldehyde, ethyl maltol, vanilla, vannillin, cinnamyl alcohol, anisole, anethole, estragole, thymol, furaneol, methanol, rosemary, lavender, citrus, freesia, apricot blossoms, greens, peach, jasmine, rosewood, pine, thyme, oakmoss, musk, vetiver, myrrh, blackcurrant, bergamot, grapefruit, acacia, passiflora, sandalwood, tonka bean, mandarin, neroli, violet leaves, gardenia, red fruits, ylang-ylang, acacia farnesiana, mimosa, tonka bean, woods, ambergris, daffodil, hyacinth, narcissus, black currant bud, iris, raspberry, lily of the valley, sandalwood, vetiver, cedarwood, neroli, strawberry, carnation, oregano, honey, civet, heliotrope, caramel, coumarin, patchouli, dewberry, helonial, coriander, pimento berry, labdanum, cassie, aldehydes, orchid, amber, orris, tuberose, palmarosa, cinnamon, nutmeg, moss, styrax, pineapple, foxglove, tulip, wisteria, clematis, ambergris, gums, resins, civet, plum, castoreum, civet, myrrh, geranium, rose violet, jonquil, spicy carnation, galbanum, petitgrain, iris, honeysuckle, pepper, raspberry, benzoin, mango, coconut, hesperides, castoreum, osmanthus, mousse de chene, nectarine, mint, anise, cinnamon, orris, apricot, plumeria, marigold, rose otto, narcissus, tolu balsam, frankincense, amber, orange blossom, bourbon vetiver, opopanax, white musk, papaya, sugar candy, jackfruit, honeydew, lotus blossom, muguet, mulberry, absinthe, ginger, juniper berries, spicebush, peony, violet, lemon, lime, hibiscus, white rum, basil, lavender, balsamics, fo-ti-tieng, osmanthus, karo karunde, white orchid, calla lilies, white rose, rhubrum lily, tagetes, ambergris, ivy, grass, seringa, spearmint, clary sage, cottonwood, grapes, brimbelle, lotus, cyclamen, orchid, glycine, tiare flower, ginger lily, green osmanthus, passion flower, blue rose, bay rum, cassie, African tagetes, Anatolian rose, Auvergne narcissus, British broom, British broom chocolate, Bulgarian rose, Chinese patchouli, Chinese gardenia, Calabrian mandarin, Comoros Island tuberose, Ceylonese cardamom, Caribbean passion fruit, Damascena rose, Georgia peach, white Madonna lily, Egyptian jasmine, Egyptian marigold, Ethiopian civet, Farnesian cassie, Florentine iris, French jasmine, French jonquil, French hyacinth, Guinea oranges, Guyana wacapua, Grasse petitgrain, Grasse rose, Grasse tuberose, Haitian vetiver, Hawaiian pineapple, Israeli basil, Indian sandalwood, Indian Ocean vanilla, Italian bergamot, Italian iris, Jamaican pepper, May rose, Madagascar ylang-ylang, Madagascar vanilla, Moroccan jasmine, Moroccan rose, Moroccan oakmoss, Moroccan orange blossom, Mysore sandalwood, Oriental rose, Russian leather, Russian coriander, Sicilian mandarin, South African marigold, South American tonka bean, Singapore patchouli, Spanish orange blossom, Sicilian lime, Reunion Island vetiver, Turkish rose, Thai benzoin, Tunisian orange blossom, Yugoslavian oakmoss, Virginian cedarwood, Utah yarrow, West Indian rosewood, and the like, and any combination thereof.

In embodiments, the first and/or second feedstocks contain plastics at least a portion of which are obtained from cellulosics, such as cellulose derivates having an acyl degree of substitution of less than 3, or 1.8 to 2.8, such as cellulose acetate, cellulose diacetate, cellulose triacetate, cellulose acetate propionate, cellulose acetate butyrate.

In embodiments, the first and/or second feedstocks contain plastics at least a portion of which are obtained from polymers having repeating terephthalate units, such as polyethylene terephthalate, polypropylene terephthalate, polybutylene terephthalate, and copolyesters thereof.

In embodiments, the first and/or second feedstocks contain plastics at least a portion of which are obtained from copolyesters having multiple dicyclohexane dimethanol moeities, 2,2,4,4-tetramethyl-1,3-cyclobutanediol moieties, or combinations thereof.

In embodiments, the first and/or second feedstocks contain plastics at least a portion of which are obtained from low-density polyethylene, high density polyethylene, linear low-density polyethylene, polypropylene, polymethylpentene, polybutene-1, and copolymers thereof.

In embodiments, the first and/or second feedstocks contain plastics at least a portion of which are obtained from high density polyethylene or fuel tanks.

In embodiments, the first and/or second feedstocks contain plastics at least a portion of which are obtained from eyeglass frames.

In embodiments, the first and/or second feedstocks contain plastics at least a portion of which are obtained from crosslinked polyethylene. An example of the first and/or second feedstocks is one which is obtained from or includes crosslinked polyethylene pipes or size reduced portions thereof. Crosslinked polyethylene is also commonly referred to as PEX. Its structure contains cross-linked bonds in the polymer to convert the thermoplastic polyethylene to a polymer which has more thermosetting characteristic. In embodiments the cross-linked polyethylene is a thermoset polymer. The crosslinked polyethylene can be obtained by crosslinking any polyethylene (LDPE, LLDPE, HDPE), but typically is obtained by crosslinking low density polyethylene. The method of crosslinking is not limited, and can be accomplished during and after extrusion. The degree of crosslinking can be at least 50%. In embodiments, the degree of crosslinking satisfied ASTM F876. In embodiments, the degree of crosslinking is from 60 to 92%, or from 65 to 89%.

The cross-linking methods may be by irradiating a tube with an electron beam, the Engel crosslinking method by mixing a peroxide with the polyethylene and crosslinking occurring before extrusion as in the long die. Crosslinking the polyethylene can also be accomplished in a silane or vinylsilane based process or in an azo based process. The types of crosslinked polyethylene include PE-Xa (peroxide crosslinked with at least 75% crosslinking), PE-Xb (moisture cure or silane based with at least 65% crosslinking), PE-Xc (electron beam based with at least 60% crosslinking), and PE-Xd (azo based with at least 60% crosslinking).

In embodiments, the first and/or second feedstocks contain plastics at least a portion of which are obtained from plastic bottles.

In embodiments, the first and/or second feedstocks contain plastics at least a portion of which are obtained from diapers.

In embodiments, the first and/or second feedstocks contain plastics at least a portion of which are obtained from Styrofoam, or expanded polystyrene.

In embodiments, the first and/or second feedstocks contain plastics at least a portion of which are obtained from flashspun high density polyethylene.

Suitable plastics (i.e. organic synthetic polymers that are solid at 25° C. at 1 atm.) include those having or classified within a resin ID code numbered 1-7 within the chasing arrow triangle established by the SPI. In embodiments, at least a portion of the feedstock to the gasifier, or at least a portion of the plastic recycle fed to the gasifier, contains one or more plastics that are not generally recycled. These would include plastics having numbers 3 (polyvinyl chloride), 5 (polypropylene), 6 (polystyrene), and 7 (other). In embodiments, the recycle plastics fed to the gasifier, or at least a portion of the feedstock, contains less than 10 wt. %, or not more than 5 wt. %, or not more than 3 wt. %, or not more than 2 wt. %, or not more than 1 wt. %, or not more than 0.5 wt. %, or not more than 0.2 wt. %, or not more than 0.1 wt. %, or not more and 0.05 wt. % plastics having or corresponding to number 3 designation (polyvinyl chloride), or optionally plastics with a number 3 and 6 designation, or optionally with a number 3, 6 and 7 designation, based on the weight of all plastics fed to the gasifier or gasification zone. In embodiments, the first and/or second feedstocks contain at least 1 wt. %, or at least 2 wt. %, or at least 3 wt. %, or at least 5 wt. %, or at least 7 wt. %, or at least 10 wt. %, or at least 12 wt. %, or at least 15 wt. %, or at least 20 wt. %, or at least 25 wt. %, or at least 30 wt. %, or at least 40 wt. %, or at least or more than 50 wt. %, or at least 65 wt. %, or at least 85 wt. %, or at least 90 wt. % plastics having or corresponding to a number 5, or a number 6, or a number 7, or a combination thereof, based on the weight of the plastics in the feedstock or fed to the gasifier or gasification zone. In embodiments, the first and/or second feedstocks can comprise at least 30, 35, 40, 45, 50, 55, 60, 65, 70, 75, 80, 85, 90, 95, or 99 weight percent of at least one, two, three, or four different kinds of resin ID codes. In embodiments, the first and/or second feedstocks contain less than 25, 20, 15, 10, 5, or 1 weight percent of polyvinyl chloride.

One of the advantages of gasifying plastics is that many plastics that would otherwise be landfilled because they cannot be re-melted (e.g. ground and melt extruded to renewed articles) can now be recycled and made into renewed products. An example of such a plastic is a thermoset plastic. In embodiments, the feedstock contains plastics at least a portion of which cannot be melt extruded into a renewed product.

One of the advantages of gasifying plastics is that many plastics that would otherwise be landfilled because they cannot or are not mechanically recycled due to the presence of an additive, coating, or dye/pigment can now be recycled and made into renewed products. For example, some plastics which are heavily dyed, or contain additives that are suited for only a limited kind of application, or have coatings can all impair the functionality or appearance of renewed products. Other plastics are typically not mechanically recycled through a process in which the plastic is melted because they are difficult to chop, granulate, or pulverize without first going through the step of densification, which adds costs. These plastics that are typically not mechanically recycled have a Resin ID code of 4, 5, 6, or 7, or combinations thereof.

In embodiments, the first and/or second feedstocks contain plastics at least a portion of which cannot or are not mechanically recycled, optionally within a 10 mile radius of the gasifier, or within a 50 mile, or within a 100 mile, or within a 150 mile, or within a 200 mile, or within a 250 mile, or within a 300 mile, or within a 400 mile, or within a 500 mile, or within a 600 mile, or within a 700 mile, or within a 800 mile, or within a 1000 mile, or within a 1250 mile, or within a 1500 mile, or within a 2000 mile radius of the gasifier, or within the same province, state, or country as the location of the gasifier.

In embodiments, the first and/or second feedstocks contain plastics at least a portion of which are obtained from polymers that are colored with a pigment or dye, optionally other than black.

In embodiments, the first and/or second feedstocks contain plastics at least a portion of which are obtained from articles having a layer of a label that is size reduced with the label.

In embodiments, the first and/or second feedstocks contain plastics at least a portion of which are obtained from articles that are not mechanically recycled due to the presence of an additive in article.

The form of the textiles useful to make size reduced textiles and/or plastics, or textile and/or plastic aggregates are not limited, and can include any of the forms of articles or materials used to make textiles described above; e.g. fibers, yarns, fabrics, cloths, finished article forms, or pieces thereof. The textiles can be of varying age and composition.

The source for obtaining post-consumer or post-industrial waste is not limited. A post-consumer plastic source can include plastic present in and/or separated from municipal solid waste streams ("MSW"). For example, an MSW stream can be processed and sorted to several discrete components, including textiles, fibers, mixed plastics, papers, wood, glass, metals, etc. Other sources of textiles and plastics include those obtained by collection agencies, or by or for or on behalf of textile and plastics brand owners or consortiums or organizations, or from brokers, or from post-industrial sources such as scrap from mills or commercial production facilities, unsold fabrics from wholesalers or dealers, from mechanical and/or chemical sorting or separation facilities, from landfills, or stranded on docks or ships.

In embodiments, at least a portion of the plastics in the first and/or second feedstocks contain or is obtained from cellulosic material. Examples of plastics that are cellulosics include cellulose acetate, cellulose diacetate, cellulose triacetate, cellulose acetate propionate, cellulose acetate butyrate, regenerated cellulose such a viscose, rayon, and Lyocel™ products. These cellulosics can be in any form, such as films, sheets, molded or stamped products, and contained in or on any article. Examples of articles containing cellulosics that can be contained in the feedstock or fed to the gasifier or gasification zone include ophthalmic products such as eyeglass frames, tool handles such as screwdriver handles, optical films such as used in the displayers or televisions, computers, mobile phones, photographic film, coatings, buttons, and toys including building bricks.

Plastics and textiles can be used in their size reduced loose form, or they can be densified prior to adding to a feedstock stream to a gasifier. A typical densification process includes a method that compacts the textiles or plastics and heats a thermoplastic polymer in or added to the textile or plastic to provide a binding matrix that encapsulates or otherwise binds thermosetting polymers and/or natural fibers ("densification"). Densification also includes processes that agglomerate the textiles or plastics through heat generated by frictional forces or particles made by extrusion or other external heat applied to the textile or plastics to soften or melt a portion or all of the textile or plastic.

The textiles and/or plastics are fed to a gasifier in combination with other fuel sources for gasification, or fed to a gasifier neat, or slurried and fed to a gasifier.

In one embodiment, the plastics and textiles are within one of the components or streams that are separated from an MSW source.

To obtain size reduced textiles or plastics, the textiles or plastics are reduced in size by any means, including by chopping, shredding, harrowing, confrication, pulverizing, or cutting a feedstock of textiles or plastics to make size reduced textiles or plastics. Optionally, the size reduced textiles or plastics can continue to be cut, comminuted, pulverized, ground or otherwise size reduced to obtain the desired average particle size if one desires to obtain finer particles. The form of the size reduced textiles and/or plastics will depend on the desired method of size reduction. For example, the size reduced textiles can be in the form of coarse or fine particles, even a powder (of any shape other than the original shape of the textile feed). Alternatively, the size reduced textiles or plastics can be in the form of shredded pieces, long strips, or randomly shaped pieces having a wide variety of shapes.

The size reduced textiles and/or plastics can be in the form of a viscous mass that do not have discrete particles. Fluidized bed granulators can be used, optionally with a drying gas, as well as tumbling granulators of disc or drum design connected to high speed mixers having cutting blades on a horizontal or vertical shaft. Examples of different kinds of suitable size reducing processes and equipment as stand-alone or coupled together include air swept mills, knife cutting, fine grinders that can have multiple grinding zones with internal classification systems, choppers with finer knives at the end, disintegrators that can handle shredding of textiles and/or plastics even high moisture feeds and then optional fine cutting or milling into smaller size such as a powder, high speed cutting blades that can have multiple zones for moving coarser material to finer material. The size reducing equipment can also include drying before cutting or simultaneous with drying Following or simultaneous with the process of size reducing the textile and/or plastic feed, the size reduced textiles and/or plastics can be treated to make textile and/or plastic aggregates in which the individual particles in textile and/or plastic aggregates have a bulk density that is higher than the bulk density of the textile and/or plastic feed used to make the size reduced textiles and/or plastics. The densification process increases the bulk density of the textiles and/or plastics. In embodiments, the bulk density of the textile and/or plastic aggregates is higher than the bulk density of the textiles and/or plastics fed to the process for size reduction. In embodiments, the bulk density of the textile and/or plastic aggregates is higher than the bulk density of an isolated size reduced textiles and/or plastics.

One method for densification can be to form agglomerates without application of external heat source (the "agglomeration process"), or by applying external heat energy in a process for forming particles ("heat treated process"). In embodiments, the textile and/or plastic aggregates can be obtained by an agglomeration process that includes pressure. In embodiments, the textile and/or plastic aggregate is obtained by an agglomeration process that does not include application of pressure. In embodiments, the textile and/or plastic aggregates are obtained by a heat-treated process that includes that application of pressure.

Examples of pressure agglomeration include compactors (roll, roll press, double roll press). Compactors roll the material into a sheet, and then feed the material to a flake breaker and granulator. The process is generally a dry process. Another example of pressure agglomeration includes briquetters which produce pillow shape agglomerates in the roll press or double roll press.

Examples of non-pressure agglomeration processes include forming agglomerates with disc pelletizers (also called pan pelletizers or granulators), agglomeration drums, pin mixers, and paddle mixers (pug mills).

Generally, the size of the agglomerates is higher than the size of the size reduced textiles and/or plastics by, for examples, combining or consolidating smaller particles into larger particles to make granules, tablets, briquettes, pellets, or the like. Since agglomerates are consolidated or pressure compacted rather than fused, they can break apart into smaller sizes more easily than extrudates in grinding or milling equipment, such as those used in a coal or petcoke grinder or mill. Agglomerates also produce fewer fines and dust and can easily flow.

The agglomerates, after formed, can be cured, dried, or fired by application of external heat sources.

In embodiments, the size reduction process and the densification process in an agglomeration process can be in different zones in the same equipment, or in the same zone in the same equipment, or the size reduced textiles and/or plastics are not discharged and isolated before the application of a densification process. For example, a single equipment can both reduce the size of the textile or plastic feed and densify either in two zones within the body of the agglomerator or even in one zone within the body of the agglomerator.

In embodiments, the size reduced textiles and/or plastics are discharged from equipment and isolated prior to feeding the size reduced textiles and/or plastics to a process for densification.

As noted, the textile and/or plastic aggregates can be formed by an agglomeration method. This can be accomplished in an agglomerator (also called a densifier) in a batch or continuous mode. The agglomeration method does not include application of external heat energy. In embodiments, the agglomeration occurs with the application of frictional heat, or frictional heat only. There are many types of commercial agglomerators available capable of densifying plastics by similar processes. In embodiments, the formation of size reduction and densification can occur in the same zone by feeding loose textiles and/or plastics to a chamber of spinning blades that shred the material for a time sufficient to frictionally heat the mass of shredded textiles and/or plastics to a softening point $T_g$ of thermoplastic polymer contained in the mass of shredded textiles and/or plastics, or otherwise to at least soften or create a tacky or viscous shredded mass. The softened size reduced viscous mass can optionally be densified and solidified by application of water onto the mass. This process does not isolate the size reduced textiles and/or plastics as particles before densification. The process of size reduction and densification can occur simultaneously. This process can also occur without applied pneumatic or hydraulic pressure during the shredding and densification process. The action of the spinning blades provides the motive force for discharging the textile and/or plastic aggregates. Pressure may be applied to discharge the material from the densification zone.

In another embodiment, the size reduced textiles and/or plastics are fed by a means such as a pneumatic conveyor to a hopper that can be stirred and then fed to an optional discharge auger or screw mounted perpendicular to the hopper or in line and parallel in the vertical plane to the hopper. The rotational speed of the auger or screw is determined by the desired throughput of the agglomeration screw. Optionally, the discharge port, screw, or any location between the hopper and agglomeration screw can be configured to check metal and removed, such as by way of magnets.

The discharge screw or auger feeds the size reduced textiles and/or plastics to an agglomeration zone containing a chamber in which the size reduced textiles and/or plastics are softened, plasticized, sintered, or otherwise compacted. One example of such a chamber is a single or double screw that either is tapered having a diameter that narrows through at least a portion of the shaft length toward the die head or outlet or a variable pitch and/or variable flight straight screw that provides compaction as the textile or plastic material moves toward the die head, or any other screw design that provides compaction. The chamber can optionally be vented. The shearing action of the screw and compaction of the textile or plastic material as it travels down the screw creates frictional heat to soften the textiles and/or plastics to a temperature effective to create an agglomerate. The screw can be a variable or constant pitch screw or have variable or constant flights. If a die is use, the holes can be configured to any shape and size. A set of rotating knives cut the agglomerated textile or plastic material exiting the die to form the textile and/or plastic aggregates.

Alternatively, In embodiments, the textiles and/or plastics, size reduced textiles and/or plastics, and/or textile and/or plastic aggregates are extruded and pelletized or in the form of pellets. The textiles and/or plastics, size reduced textiles and/or plastics can be fed to a chamber or process that applies heat energy to the textiles and/or plastics to melt at least a portion of the textiles and/or plastics. Examples include a hot melt granulator or extruder with a die.

In embodiments, there is provided a molten blend of size reduced textiles and/or plastics obtained by any conventional melt blending techniques. A molten blend includes textiles and/or plastics completely melted or textiles and/or plastics containing a portion of material that is melted and a portion of material that is not melted. Some material in textiles and/or plastics will not melt before they thermally degrade, such as some natural fibers.

The melt blend can be extruded and cooled into sheets or rods and/or pelletized into pellet form before or after cooling. For example, the melt blend can be extruded into any form, such pellets, droplets, or other particles, strands, rods, or sheets, which can, if desired, be further granulated and/or pulverized to the desired size.

The type of textile and/or plastic aggregates is not limited, and can be any one of those mentioned below, but at least a portion of the textiles and/or plastics contain thermoplastic polymer. Thermoplastic polymers assist to retain the shape and particle integrity, allow their processing, and avoid excessive energy costs. Textile and/or plastic aggregates that do not contain any or insufficient thermoplastic polymer content will not retain a consistent discrete shape in downstream size reducing processes, will generate excessive fines, and can have a wide size variation. The amount of thermoplastic polymer, or thermoplastic fibers, in any one of the textile or plastic feed, size reduced textiles and/or plastics, or textile and/or plastic aggregates agglomerates is at least 5 wt. %, or at least 10 wt. %, or at least 25 wt. %, or at least 50 wt. %, or at least 75 wt. %, Y0.98 wt. %, or 100 wt. %, based on the weight of the corresponding textile or plastic, i.e. textile or plastic feed, size reduced textiles and/or plastics, or densified textile and/or plastic agglomerates.

The source of thermoplastic polymer in the textiles and/or plastics, size reduced textiles and/or plastics, or densified agglomerates can be contained in the textiles and/or plastics and optionally no additional source of thermoplastic polymer is added to the textiles and/or plastics in the agglomeration zone or the melt zone of heat applied densification. If the textiles and/or plastics do not contain thermoplastic polymer or insufficient amount of thermoplastic polymer, a source of thermoplastic polymer can be combined with the textiles and/or plastics or size reduced textiles and/or plastics. An example of a source of thermoplastic polymer includes binder powder. Desirably, a source of thermoplastic polymer is a source of recycle plastics other than textiles and/or plastics, whether virgin textiles and/or plastics or recycle textiles and/or plastics ("recycle plastics"). This has the advantage of ensuring that the densified textile and/or plastic agglomerates have a recycle source content of 100%. The source of thermoplastic polymer can be added to the textile or plastic feed prior to size reduction, to the size reduced textiles and/or plastics as a feed to the densification process, or as a separate feed stream into the densification process. At least a portion of the source of recycle plastics can be from the same facility or from a part of the same separation train used to separate the textiles and/or plastics (that are densified) from MSW. For example, a separation facility processing MSW can separate glass, metal, plastics, and textile components from each other and isolate those components. The recycle plastics components and textile components from that facility can be combined in the densification process to provide textile and/or plastic aggregates containing 100% recycle content. Alternatively, a separation facility processing MSW can be configured to separate a plastics and textiles as one component from an MSW stream, to further reduce the cost of mechanical separation. In each of these embodiments, the recycle plastics provide a convenient source of thermoplastic polymer as a material that both binds textiles and/or plastics, and in particular natural fibers, allows the agglomerate or hot melt granules to be further comminuted if desired, and provide a good source of fuel along with textiles and/or plastics in the gasification process.

In embodiments, the recycle source content in the densified textile and/or plastic agglomerates is at least 50%, or at least 60%, or at least 70%, or at least 80%, or at least 85%, or at least 90%, or at least 92%, or at least 95%, or at least 97%, or at least 98%, or at least 99%, or at least 99.5.%, or at even 100%, in each case wt. % based on the weight of the densified textile and/or plastic agglomerates.

If a binder is employed, it can be natural or synthetic. Any conventional thermoplastics known as binders are suitable, as well as whey (or waste whey), sugar, or ligno sulfonates (or waste lignosulfates). The binder desirably is one which can be granulated without disintegrating, and accordingly, thermoplastic textiles and/or plastics binders are more desirable.

In embodiments, the textiles and/or plastics or size reduced textiles and/or plastics are densified without combining them with a feed containing thermoplastic polymer (e.g. binder powders or recycle plastics). Some size reduced textiles and/or plastics contain sufficient thermoplastic textiles and/or plastics synthetic fibers to allow the fibers to be densified by heat energy (whether indirect by frictional energy or external application of a heat energy source) above the $T_g$ of the thermoplastic fibers in the size reduces textiles and/or plastics. Some size reduced textiles and/or plastics contain at least 25 wt. %, or at least 50 wt. %, or at least 75 wt. %, or at least 90 wt. %, or at least 95 wt. % thermoplastic textiles and/or plastics fibers.

In embodiments, the median average size of the textiles and/or plastic aggregates in their longest dimension are smaller than the median average size of the textile and/or plastic aggregates in their longest dimension. This can be the case when the textiles and/or plastics are size reduced down to a fine powder and the agglomerate or hot melt particles are larger. Alternatively, the median average size of the reduced size textiles and/or plastics in their longest dimension are larger than the median average size of the textile and/or plastic aggregates particles.

In embodiments, the densification step includes the application of heat or are processed by a heat-treated process. The size reduced textiles and/or plastics are subjected to an external source of heat energy at or above the $T_g$ of the thermoplastic polymer in the synthetic fibers contained in the size reduced fiber stream, causing the softened or melted thermoplastic textiles and/or plastics to flow around and bind the natural fibers and any thermoset synthetic fibers. Upon cooling, the partially or fully molten textiles and/or plastics are solidified into a desired shape, and optionally further granulated or pulverized to a final desired size in one or more steps), or in the final granulate shape suitable for (i) shipping to a gasification facility for further granulation to a size suitable for introducing into the gasifier or (ii) use as a feed to the gasifier without further granulation.

In embodiments, at least a portion or all of the textile and/or plastic aggregates in the feedstock composition or stream, or the feedstock composition or stream fed to a gasifier or into the gasification zone, are densified textiles and/or plastics aggregates. In embodiments, the densified textile and/or plastic aggregates contain, or as fed to a gasifier or a feedstock to a gasifier contain, at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. %, or at least 70 wt. %, or at least 75 wt. %, or at least 80 wt. %, or at least 85 wt. %, or at least 90 wt. %, or at least 95 wt. % or at least 97 wt. % or at least 98 wt. % or at least 99 wt. % or at least 99.5 wt. % material obtained from textiles and/or plastics, based on the weight of the textile and/or plastic aggregates in the feedstock stream.

In embodiments, at least 20%, or at least 30%, or at least 50%, or at least 75%, or at least 80%, or at least 90%, or at least 95%, or at least 98% of the fibers in the textiles and/or plastics feedstock have an aspect ratio L:D of at least 1.5:1, or at least 1.75:1, or at least 2:1, or at least 2.25:1, or at least 2.5:1, or at least 2.75:1, or at least 3:1, or at least 3.25:1, or at least 3.5:1, or at least 3.75:1, or at least 4:1, or at least 4.5:1, or at least 5:1, or at least 5.5:1, or at least 6:1.

Non-combustible inorganic matter such as metals and minerals may be contained in the textile and/or plastic aggregates for gasification. Examples include tin, cobalt, manganese, antimony, titanium, sodium, calcium, sulfur, zinc, and aluminum, their oxides and other compounds thereof may be present in the textile and/or plastic aggregates because a gasifier, and especially slagging gasifiers, are well equipped to handle minerals and metals in a feedstock. Advantageously, titanium and calcium that may be present in the textile and/or plastic aggregates can be slag modifiers.

In embodiments, the amount of calcium compounds present in the ash textile and/or plastic aggregates is at least 30 wt. %, or at least 40 wt. %, or at least 50 wt. %, or at least 55 wt. %, or at least 60 wt. %, or at least 63 wt. %, based on the weight of textile and/or plastic aggregates ash. The upper amount is desirably not more than 90 wt. %, or not more than 80 wt. %, or not more than 75 wt. %, based on the weight of textile and/or plastic aggregates ash.

In another embodiment, the amount of sodium compounds present in the ash of textile and/or plastic aggregates is at least 2 wt. %, or at least 3 wt. %, or at least 4 wt. %, or at least 5 wt. %, or at least 6 wt. %, based on the weight of the textile and/or plastic aggregates ash. The upper amount is desirably not more than 20 wt. %, or not more than 17 wt. %, or not more than 15 wt. %, based on the weight of textile and/or plastic aggregates ash.

In another embodiment, the amount of titanium compounds present in the ash of textile and/or plastic aggregates is at least 30 wt. %, or at least or at least 75 wt. %, based on the weight of textile and/or plastic aggregates ash. The upper amount is desirably not more than 96 wt. %, or not more than 90 wt. %, or not more than 86 wt. %, based on the weight of the textile and/or plastic aggregates ash.

In another embodiment, the amount of iron compounds present in the ash of textile and/or plastic aggregates used in the feedstock is not more than 5 wt. %, or at least 1.5 wt. %, or at least 2 wt %, based on the weight of textile and/or plastic aggregates ash.

In another embodiment, the amount of aluminum compounds present in the ash of textile and/or plastic aggregates used in the feedstock is not more than 20 wt. %, or not more than 15 wt. %, or not more than 10 wt. %, or not more than 5 wt. %, or not more than 3 wt. %, or not more than 2 wt. %, or not more than 1.5 wt. %, based on the weight of the textile and/or plastic aggregates ash.

In another embodiment, the amount of silicon compounds present in the ash of textile and/or plastic aggregates used in the feedstock is not more than 20 wt. %, or not more than 15 wt. %, or not more than 10 wt. %, or not more than 8 wt. %, or not more than 6 wt. %, based on the weight of the textile and/or plastic aggregates ash.

Desirably, the textile and/or plastic aggregates contain low levels or no halide containing polymers, in particular polyvinyl chloride, polyvinyl fluoride, polyvinylidene fluoride, and polytetrafluoroethane, and other fluorinated or chlorinated polymers, especially if the textile and/or plastic aggregates are fed to a refractory lined gasifier. The release of chlorine or fluorine elements or radicals over time can impact the longevity of refractory lining on gasifiers operating at high temperature and pressure. In embodiments, the textile and/or plastic aggregates contain less than 10 wt. %, or not more than 8 wt. %, or not more than 6 wt. %, or not more than 5 wt. %, or not more than 4 wt. %, or not more than 3.5 wt. %, or not more than 3 wt. %, or not more than 2.5 wt. %, 1.5 wt. %, or not more than 1 wt. %, or not more than 0.5 wt. %, or not more than 0.25 wt. %, or not more than 0.1 wt. %, or not more than 0.05 wt. %, or not more than 0.005 wt. %, or not more than 0.001 wt. %, or not more than 0.0005 wt. %, or not more than 0.0001 wt. %, or not more than 0.00005 wt. % halide containing polymers, based on the weight of the textile and/or plastic aggregates. Desirably, the halide minimized or excluded is chlorine or fluorine.

In embodiments, the textile and/or plastic aggregates (those ground to the final size as combined into the feedstock composition) are desirably not pyrolyzed or torrefied prior to their introduction into the gasifier, and desirably, the textiles and/or plastics are not obtained from a source of textiles and/or plastics which have been pyrolyzed or torrefied.

In another embodiment, the textile and/or plastic aggregates, once made, are not thereafter melted or extruded prior to their entry into the gasifier. In another embodiment, the textile and/or plastic aggregates are not melted or extruded or do not receive a pyrolysis thermal treatment, or do not receive a thermal treatment above 225° C., or above 210° C., or above 200° C., or above 195° C., or above 190° C., or above 175° C., or above 160° C., or above 150° C., or above 140° C., or above 130° C., or above 120° C., or above 110° C., or above 100° C., or above 90° C., or above 80° C., or above 60° C., or above 58° C. or above their nominal temperature at their ambient conditions prior to their introduction into the gasification zone. It is to be noted that the textile and/or plastic aggregates can be dried before their introduction into the solid fossil fuel feedstock composition, however, this would not be necessary in a slurry-based feedstock composition such as in water, or a petroleum-based oil, hydrocarbon or oxygenated hydrocarbon fuel feedstock.

Polymers, intermediates, and articles such as fibers, textiles and molded articles having a recycle content are broadly named as Recycle PIA (recycle polymers, intermediates or articles). The polymers, intermediates and articles are as described throughout this description. Recycle PIA can be obtained in a reaction scheme as described herein, or can be obtained by way of a recycle content allotment, provided that the allotment has its origin in, or withdrawn from an inventory of allotments containing at least one allotment having its origin in, gasifying a feedstock containing a fossil fuel and high concentrated recycle textiles and/or plastics. The "recycle content allotment" is a recycle content value that is transferred from an originating composition, compound or polymer at least a portion of which is obtained by or with the gasification of feedstock a feedstock containing a fossil fuel and high concentrated recycle textiles and/or plastics, to a receiving composition, compound, or polymer (referred to herein as a "composition" for brevity) receiving the allotment.

There is also provided a circular manufacturing process comprising:
 (i) providing recycle textiles and/or plastics, and
 (ii) size reducing, agglomerating, and/or densifying said recycle textile and/or plastic to form textile and/or plastic aggregates, and
 (iii) gasifying said textile and/or plastic aggregates to produce recycle derived syngas, and
 (i) reacting said recycle derived syngas to make a recycle content intermediate, polymer, or article (Recycle PIA) each of which have their origin at least in part to said recycle derived syngas or
 (ii) assigning a recycle content allotment, obtained from said recycle polymer, to an intermediate, polymer, or article to produce a Recycle PIA; and
 (iv) optionally, taking back at least a portion of said Recycle PIA as a feedstock to said gasification process step (i), or (ii), or (iii).

In the above described process, an entirely circular or closed loop process is provided in which textiles and/or plastics can be recycled multiple times to make the same family or classification of textiles and/or plastics.

Examples of articles that are included in PIA are fibers, yarns, tow, continuous filaments, staple fibers, rovings, fabrics, textiles and/or plastics, flake, sheet, compounded sheet, and consumer articles.

In embodiments, the allotment can be assigned to an intermediate, polymer, or article to produce a Recycle PIA directly from a recycle content value taken from the recycle textile and/or plastic aggregates or from the step of gasifying a feedstock containing a fossil fuel and textile and/or plastic aggregates, or the allotment can be assigned to the intermediate, polymer, or article to product a recycle PIA indirectly by assigning the recycle content value taken from a recycle inventory into which recycle content value is deposited from the recycle content present in the recycle textile and/or plastic aggregates or the step of gasifying a feedstock containing a fossil fuel and textile and/or plastic aggregates.

In one embodiment, the Recycle PIA is a polymer or article (e.g. fiber) of the same family or classification of polymers or articles (e.g. fibers) contained in or one the recycle textile and/or plastic used in step (i).

In one embodiment, a Recycle PIA can be made by a process in which textile and/or plastic aggregates are gasified according to any of the processes described herein.

There is also provided a circular manufacturing process comprising:
1. A manufacturer of syngas, or one among its Family of Entities, or an entity contracted with either of them (collectively the "Recipient"), receiving recycle textiles and/or plastics (whether post-industrial or post-consumer), optionally and from an industrial supplier of said articles (e.g. textiles and/or plastics) or fibers contained in or on said textile or plastic, and
2. One or more of the Recipients size reducing said textile or plastic to make textile and/or plastic aggregates, and
3. One or more of the Recipients gasifying said textile and/or plastic aggregates to produce recycle derived syngas, and
4. either
    (i) reacting said recycle derived syngas to make a recycle content intermediate, polymer, or article (Recycle PIA) each of which have their origin at least in part to said recycle derived syngas or
    (ii) assigning a recycle content allotment, obtained from said recycle textile or said textile and/or plastic aggregates, to an intermediate, polymer, or article to thereby produce a Recycle PIA; and
5. optionally, furnishing at least a portion of said Recycle PIA to said industrial supplier, or to an entity contracted with said industrial supplier or with one among the Family of Entities of the industrial supplier for the supply of said Recycle PIA or an article made with said Recycle PIA.

In embodiments, the allotment can be assigned to an intermediate, polymer, or article to produce a Recycle PIA directly from a recycle content value taken from the recycle textile and/or plastic aggregates or from the step of gasifying a feedstock containing a fossil fuel and recycle textiles and/or plastics or textile and/or plastic aggregates, or the allotment can be assigned to the intermediate, polymer, or article to product a recycle PIA indirectly by assigning the recycle content value taken from a recycle inventory into which recycle content value is deposited from the recycle content present in the recycle textile and/or plastic aggregates or the step of gasifying a feedstock containing a fossil fuel and textile and/or plastic aggregates.

In the above described process, an entirely circular or closed loop process is provided in which textiles and/or plastics can be recycled multiple times to make the same family or classification of textiles and/or plastics. The industrial supplier may furnish a processor entity with the textile and/or plastic or articles containing the textile and/or plastic to process those textiles and/or plastics or articles into a form suitable or more suitable for gasification as further described herein to make textile and/or plastic aggregates, and in turn, the processor entity supplies the textile and/or plastic aggregates or precursors thereof to the manufacturer of syngas or one among its Family of Entities who can either feed to textile and/or plastic aggregates as such to a feedstock stream to a gasifier, or can further process the precursors or textile and/or plastic aggregates into a final size suitable for gasification by any suitable process, such as pulverization or grinding. The gasification processes, equipment, and designs used can be any of those mentioned herein. The syngas made using feedstocks containing the textile and/or plastic aggregates can then either by converted through a reaction scheme to make Recycle PIA, or the allotments created by such gasification step or obtained from the recycle textiles and/or plastics or textile and/or plastic aggregates can be stored in an inventory of allotments, and from the inventory of allotments from any source, a portion thereof can be withdrawn and assigned to an intermediate, polymer or article to make Recycle PIA. To close the circularity of the textile and/or plastic, at least a portion of the Recycle PIA can by furnished to the supplier of the textiles and/or plastics, or it can be supplied to any entity contracted with the supplier to process the Recycle PIA into a different form, different size, or to combine with other ingredients or textiles and/or plastics (e.g. compounders and/or sheet extruders), or to make articles containing the PIA, for supply to or on behalf of the supplier. The Recycle PIA furnished to the industrial supplier or one of its contracted entities is desirably in the same family or type of textile and/or plastic as the textile and/or plastic or article containing the textile and/or plastic was supplied by the industrial supplier to the Recipient.

A "recycle content allotment" or "allotment" means a recycle content value that is:
a. transferred from a recycle waste (which is any recycle waste stream whether or not it contains recycle textiles and/or plastics) to a receiving composition (e.g., compound, polymer, article, intermediate, feedstock, product, or stream) that may or may not have a physical component that is traceable to the recycle waste; or
b. deposited into a recycle inventory at least a portion of which originates from recycle waste.

An allotment can be an allocation or a credit. A recycle waste is any one of waste streams identified throughout this disclosure, including the size reduced textiles and/or plastics, densified textiles and/or plastics, the textiles and/or plastics from which they originate, or the feedstock composition containing the densified textiles and/or plastics.

The recycle content value (whether by mass or percentage or any other unit of measure) can optionally be determined according to a standard system for tracking, allocating, and/or crediting recycle content among various compositions.

A "recycle content value" is a unit of measure representative of a quantity of material having its origin in recycle textile and/or plastic. The recycle content value can have its origin in any type of recycled textile and/or plastic or any recycle textile and/or plastic processed in any type of process before being gasified.

The particular recycle content value can be determined by a mass balance approach or a mass ratio or percentage or any other unit of measure and can be determined according to any system for tracking, allocating, and/or crediting recycle content among various compositions. A recycle content value can be deducted from a recycle inventory and applied to a product or composition to attribute recycle content to the product or composition. A recycle content value does not have to originate from gasifying recycle textile and/or plastic, and can be a unit of measure having its known or unknown origin in any technology used to process recycle textile and/or plastic. In one embodiment, at least a portion of the recycle textiles and/or plastics from which an allotment is obtained is also gasified as described throughout the one or more embodiments herein; e.g. combined with a fossil fuel and subjected to gasification.

In one embodiment, at least a portion of the recycle content allotment or allotment or recycle value deposited into a recycle content inventory is obtained from recycle textile and/or plastic aggregates. Desirably, at least 60%, or at least 70%, or at least 80%, or at least 90% or at least 95%, or up to 100% of the:
 a. allotments or
 b. deposits into the recycle inventory, or
 c. recycle content value in the recycle inventory, or
 d. recycle content value applied to compositions to make Recycle PIA are obtained from recycle textile and/or plastic.

A recycle content allotment can include a recycle content allocation or a recycle content credit obtained with the transfer or use of a raw material. In embodiments, the polymer, intermediate, composition, article or stream receiving the recycle content allotment can be or contain a portion of a non-recycle composition (e.g., compound, polymer, feedstock, product, or stream). A "non-recycle" means a composition (e.g., compound, polymer, feedstock, product, or stream) none of which was directly or indirectly derived from recycled waste of any kind, including textile and plastic.

A "recycle content allocation" and "allocation" mean a type of recycle content allotment, where the entity or person supplying a composition sells or transfers the composition to the receiving person or entity, and the person or entity that made the composition has an allotment at least a portion of which can be associated with the composition sold or transferred by the supplying person or entity to the receiving person or entity. The supplying entity or person can be controlled by the same entity or person(s) or a variety of affiliates that are ultimately controlled or owned at least in part by a parent entity ("Family of Entities"), or they can be from a different Family of Entities. Generally, a recycle content allocation travels with a composition and with the downstream derivates of the composition. An allocation may be deposited into a recycle inventory and withdrawn from the recycle inventory as an allocation and applied to a composition to make a Recycle PIA.

A "recycle content credit" and "credit" means a type of recycle content allotment and may or may not contain a physical component that is traceable to high concentration recycle polymer derived syngas. For example, the (i) manufacturer of the product can operate within a legal framework, or an association framework, or an industry recognized framework for making a claim to a recycle content through, for example, a system of credits transferred to the product manufacturer regardless of where or from whom the high concentration recycle polymer derived syngas, or downstream products made thereby, or reactant feedstocks to make the polymer and/or article, is purchased or transferred, or (ii) a supplier of the high concentration recycle polymer derived syngas stream or downstream products made thereby ("supplier") operates within an allocation framework that allows for allocating a recycle content value to a portion or all of the high concentration recycle polymer derived syngas stream or downstream products made thereby and to transfer the allotment to the manufacturer of the product or any intermediary who obtains a supply of high concentration recycle polymer derived syngas stream or a downstream product thereof, from the supplier.

In embodiments, a credit is available for sale or transfer or use, or is sold or transferred or used, either:
 a. without the sale of a composition, or
 b. with the sale or transfer of a composition but the allotment is not associated the sale or transfer of the composition, or
 c. is deposited into or withdrawn from a recycle inventory that does not track the molecules of a recycle content feedstock to the molecules of the resulting compositions which were made with the recycle content feedstocks, or which does have such tracking capability but which did not track the particular allotment as applied to a composition.

In embodiments, an allotment may be deposited into a recycle inventory, and a credit may be withdrawn from the inventory and applied to a composition to make a Recycle PIA. This would be the case where an allotment is created from recycle textiles and/or plastics and deposited into a recycle inventory, and deducting a recycle content value from the recycle inventory and applying it to a composition to make a Recycle PIA that either has no portion originating from syngas or does have a portion originating from syngas but such syngas making up the portion of the composition was not a recycle derived syngas. In this system, one need not trace the source of a reactant compound or composition back to the manufacture of recycle derived syngas stream or back to any atoms contained in the recycle derived syngas stream, but rather can use any reactant compound or composition made by any process and have associated with such reactant compound or composition, or have associated with the Recycle PIA, a recycle content allotment. In an embodiment, the Recycle PIA reactants (the compositions used to make Recycle PIA or the compositions to which an allotment is applied) do not contain recycle content.

In one embodiment, the composition receiving an allotment to make a Recycle PIA originates in part from a syngas stream obtained by any gasification process. The feedstock to the gasification process may optionally contain fossil fuel such as coal. The feedstock may optionally also contain a combination of fossil fuel and recycle textiles and/or plastics or textile and/or plastic aggregates. In one embodiment, there is provided a process in which:
 a. recycle textiles and/or plastics is obtained,
 b. a recycle content value (or allotment) is obtained from the recycle textile and/or plastic and
  i. deposited into a recycle inventory, and an allotment (or credit) is withdrawn from the recycle inventory and applied to a composition to obtain a Recycle PIA, or
  ii. applied to a composition to obtain a Recycle PIA; and
 c. at least a portion of the recycle textile and/or plastic is subjected to a gasification process, optionally by combining it with a fossil fuel as a feedstock to a gasifier, optionally according to any of the designs or processes described herein; and
 d. optionally at least a portion of the composition in step b. originates from a syngas stream, optionally the syngas stream having been obtained by any of the feedstocks and methods described herein.

The steps b. and c. do not have to occur simultaneously. In one embodiment, they occur within a year of each other, or within six (6) months of each other, or within three (3) months of each other, or within one (1) month of each other, or within two (2) weeks of each other, or within one (1) week of each other, or within three (3) days of each other. The process allows for a time lapse between the time an entity or person receiving the recycle textile and/or plastic and creating the allotment (which can occur upon receipt or ownership of the recycle textile and/or plastic) and the actual processing of the recycle textile and/or plastic in a gasifier.

As used herein, "recycle inventory" and "inventory" mean a group or collection of allotments (allocations or credits) from which deposits and deductions of allotments in any units can be tracked. The inventory can be in any form (electronic or paper), using any or multiple software programs, or using a variety of modules or applications that together as a whole tracks the deposits and deductions. Desirably, the total amount of recycle content withdrawn (or applied to the Recycle PIA) does not exceed the total amount of recycle content allotments or credits on deposit in the recycle inventory (from any source, not only from gasification of recycle textiles and/or plastics). However, if a deficit of recycle content value is realized, the recycle content inventory is rebalanced to achieve a zero or positive recycle content value available. The timing for rebalancing can be either determined and managed in accordance with the rules of a particular system of accreditation adopted by the recycle derived syngas manufacturer or by one among its Family of Entities, or alternatively, is rebalanced within one (1) year, or within six (6) months, or within three (3) months, or within one (1) month of realizing the deficit. The timing for depositing an allotment into the recycle inventory, applying an allotment (or credit) to a composition to make a Recycle PIA, and gasifying recycle textiles and/or plastics, need not be simultaneous or in any particular order. In one embodiment, the step of gasifying a particular volume of recycle textiles and/or plastics occurs after the recycle content value or allotment from that volume of recycle textile and/or plastic is deposited into a recycle inventory. Further, the allotments or recycle content values withdrawn from the recycle inventory need not be traceable to recycle textiles and/or plastics or gasifying recycle textiles and/or plastics, but rather can be obtained from any waste recycle stream, and from any method of processing the recycle waste stream. Desirably, at least a portion of the recycle content value in the recycle inventory is obtained from recycle textiles and/or plastics, and optionally at least a portion of recycle textiles and/or plastics are processed in the one or more gasification processes as described herein, optionally within a year of each other and optionally at least a portion of the volume of recycle textiles and/or plastics from which a recycle content value is deposited into the recycle inventory is also processed by any or more of the gasification processes described herein.

The determination of whether a Recycle PIA is derived directly or indirectly from recycled waste is not on the basis of whether intermediate steps or entities do or do not exist in the supply chain, but rather whether at least a portion of the recycle textile and/or plastic molecules fed to the gasifier can be traced into a Recycle PIA. The Recycle PIA is considered to be directly derived from recycle textile and/or plastic or have direct contact with recycle textile and/or plastic if at least a portion of the molecules in the Recycle PIA can be traced back, optionally through one or more intermediate steps or entities, to at least a portion of the recycle derived syngas molecules. Any number of intermediaries and intermediate derivates can be made before the Recycle PIA is made.

A Recycle PIA can be indirectly derived from recycled textiles and/or plastics if no portion of its molecules are obtained from recycle derived syngas molecules or some portion of is molecules are obtained from recycle derived syngas molecules but the Recycle PIA has a recycle content value that exceeds the recycle content value associated with the recycle derived syngas molecules, and in this latter case, a Recycle PIA can be both directly and indirectly derived from recycle textile and/or plastic.

In embodiments, the Recycle PIA is indirectly derived from recycle textile and/or plastic or recycle derived syngas. In another embodiment, the Recycle PIA is directly derived from recycle textile and/or plastic or recycle derived syngas. In another embodiment, the Recycle PIA is indirectly derived from recycle textile and/or plastic or recycle derived syngas and no portion of the Recycle PIA is directly derived from the recycle textile and/or plastic or recycle derived syngas.

In another embodiment, there is provided a variety of methods for apportioning the recycle content among the various Recycle PIA compositions made by any one entity or a combination of entities among the Family of Entities of which the recycle derived syngas manufacturer is a part. For example, the recycle derived syngas manufacturer, of any combination or the entirety of its Family of Entities, or a Site, can:

a. adopt a symmetric distribution of recycle content values among its product(s) based on the same fractional percentage of recycle content in one or more feedstocks, or based on the amount of allotment received. For example, if 5 wt. % of the gasification feedstock is textile and/or plastic aggregates, or if the recycle content value is 5 wt. % of the entire gasifier feedstock, then all Recycle PIA compositions may contain 5 wt. % recycle content value. In this case, the amount of recycle content in the products is proportional to the amount of recycle content in the feedstock to make the products; or b. adopt an asymmetric distribution of recycle content values among its product(s) based on the same fractional percentage of recycle content in the one or more feedstocks, or based on the amount of allotment received. For example, if 5 wt. % of the gasifier feedstock is recycle textile and/or plastic, or if the allotment value is 5 wt. % of the entire gasifier feedstock, then one volume or batch of Recycle PIA can receive a greater amount of recycle content value that other batches or volume of Recycle PIA. One batch of PVA can contain 20% recycle content by mass, and another batch can contain zero 0% recycle content, even though both volumes may be compositionally the same, provided that the amount of recycle content value withdrawn from a recycle inventory and applied to the Recycle PIA does not exceed the amount of recycle content value deposited into the recycle inventory, or if a deficit is realized, the overdraft is rebalanced to zero or a positive credit available status as described above. In the asymmetric distribution of recycle content, a manufacturer can tailor the recycle content to volumes of Recycle PIA sold as needed among customers, thereby providing flexibility among customers some of whom may need more recycle content than others in a PVA volume.

Both the symmetric distribution and the asymmetric distribution of recycle content can be proportional on a Site wide basis, or on a multi-Site basis. In embodiments, the recycle content input (recycle textiles and/or plastics or allotments) can be within a Site, and recycle content values from said inputs are applied to one or more compositions made at the same Site to make Recycle PIA. The recycle content values can be applied symmetrically or asymmetrically to one or more different compositions made at the Site.

In embodiments, the recycle content input or creation (recycle content feedstock or allotments) can be to or at a first Site, and recycle content values from said inputs are transferred to a second Site and applied to one or more compositions made at a second Site. The recycle content values can be applied symmetrically or asymmetrically to the compositions at the second Site.

In an embodiment, the Recycle PIA has associated with it, or contains, or is labelled, advertised, or certified as containing recycle content in an amount of at least 0.01 wt. %, or at least 0.05 wt. %, or at least 0.1 wt. %, or at least 0.5 wt. %, or at least 0.75 wt. %, or at least 1 wt. %, or at least 1.25 wt. %, or at least 1.5 wt. %, or at least 1.75 wt. %, or at least 2 wt. %, or at least 2.25 wt. %, or at least 2.5 wt. %, or at least 2.75 wt. %, or at least 3 wt. %, or at least 3.5 wt. %, or at least 4 wt. %, or at least 4.5 wt. %, or at least 5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. % and/or the amount can be up to 100 wt. %, or up to 95 wt. %, or up to 90 wt. %, or up to 80 wt. %, or up to 70 wt. %, or up to 60 wt. %, or up to 50 wt. %, or up to 40 wt. %, or up to 30 wt. %, or up to 25 wt. %, or up to 22 wt. %, or up to 20 wt. %, or up to 18 wt. %, or up to 16 wt. %, or up to 15 wt. %, or up to 14 wt. %, or up to 13 wt. %, or up to 11 wt. %, or up to 10 wt. %, or up to 8 wt. %, or up to 6 wt. %, or up to 5 wt. %, or up to 4 wt. %, or up to 3 wt. %, or up to 2 wt. %, or up to 1 wt. %, or up to 0.9 wt. %, or up to 0.8 wt. %, or up to 0.7 wt. %. The recycle content associated with the Recycle PIA can be associated by applying an allotment (credit or allocation) to any polymer and/or article made or sold. The allotment can be contained in an inventory of allotments created, maintained or operated by or for the Recycle PIA manufacturer. The allotment can be obtained from any source along any manufacturing chain of products provided that its origin is in gasifying a feedstock containing a fossil fuel and textile and/or plastic aggregates.

The amount of recycle content in a reactant compound or composition, or the amount of recycle content applied to the Recycle PIA, or the amount of textile and/or plastic aggregates needed to feed the gasifier to claim a desired amount of recycle content in the Recycle PIA in the event that all the recycle content from the recycle textile and/or plastic feedstock is applied to the Recycle PIA, can be determined or calculated by any of the following methods:
(i) the amount of an allotment associated with the Recycle PIA is determined by the amount certified or declared by the supplier of transferred Recycle PIA, or
(ii) the amount of allotment declared by the entity using Recycle PIA, or
(iii) using a mass balance approach to back-calculate the minimum amount of recycle content in the feedstock from an amount of recycle content declared, advertised, or accounted for by the manufacturer, whether or not accurate, as applied to the Recycle PIA product,
(iv) blending of non-recycle content with textile and/or plastic aggregates feedstock, or associating recycle content to a portion of the feedstock, using pro-rata mass approach In one embodiment, the Recycle PIA manufacturer can make Recycle PIA, or process a reactant compound or composition and make a Recycle PIA, or make Recycle PIA by obtaining any source of a reactant compound or composition from a supplier, whether or not such reactant compound or composition has any recycle content, and either:

i. from the same supplier of the reactant compound or composition, also obtain a recycle content allotment applied to either syngas or to any product, article, polymer, or composition, or
ii. from any person or entity, obtaining a recycle content allotment without a supply of a reactant compound or composition from said person or entity transferring said recycle content allotment.

The allotment in (i) can be obtained from a supplier of the reactant compound or composition used to make Recycle PIA, and the supplier also supplies and transfers the reactant compound or composition to the Recycle PIA manufacturer or within its Family of Entities. The circumstance described in (i) allows a Recycle PIA manufacturer to obtain a supply of a reactant compound or composition that has non-recycle content, yet obtain a recycle content allotment from the reactant compound or composition. In one embodiment, the reactant compound or composition supplier transfers a recycle content allotment to the Recycle PIA manufacturer as well as a supply of reactant compound or composition to the Recycle PIA manufacturer, where the recycle content allotment is not associated with the reactant compound or composition supplied, provided that the recycle content allotment transferred has its origins in gasifying recycle textile and/or plastic aggregates. The recycle content allotment does not have to be tied to an amount of recycle content in a reactant compound or composition or to any monomer used to make Recycle PIA, but rather the recycle content allotment transferred by the reactant compound or composition supplier can be associated with other products having their origin in a recycle derived syngas stream other than those in a reaction scheme to make polymer and/or articles. This allows flexibility among the reactant compound or composition supplier and Recycle PIA manufacturer to apportion a recycle content among the variety of products they each make. In each of these cases, however, the recycle content allotment has its origins in gasifying recycle textiles and/or plastics.

In one embodiment, the reactant compound or composition supplier transfers a recycle content allotment to the Recycle PIA manufacturer and a supply of reactant compound or composition to the Recycle PIA manufacturer, where the recycle content allotment is associated with reactant compound or composition. Optionally, the reactant compound or composition being supplied can be derived from recycle textile and/or plastic feedstock and at least a portion of the recycle content allotment being transferred can be the recycle content in the reactant compound or composition. The recycle content allotment transferred to the Recycle PIA manufacturer can be up front with the reactant compound or composition supplied, optionally in installments, or with each reactant compound or composition portion supplier, or apportioned as desired among the parties.

The allotment in (ii) is obtained by the Recycle PIA manufacturer (or its Family of Entities) from any person or entity without obtaining a supply of reactant compound or composition from the person or entity. The person or entity can be a reactant compound or composition manufacturer that does not supply reactant compound or composition to the Recycle PIA manufacturer or its Family of Entities, or the person or entity can be a manufacturer that does not make a reactant compound or composition. In either case, the circumstances of (ii) allows a Recycle PIA manufacturer to obtain a recycle content allotment without having to purchase any reactant compound or composition from the entity supplying the recycle content allotment. For example, the person or entity may transfer a recycle content allotment through a buy/sell model or contract to the Recycle PIA manufacturer or its Family of Entities without requiring purchase or sale of an allotment (e.g. as a product swap of products that are not reactant compound or composition), or the person or entity may outright sell the allotment to the Recycle PIA manufacturer or one among its Family of Entities. Alternatively, the person or entity may transfer a product, other than a reactant compound or composition, along with its associated recycle content allotment to the Recycle PIA manufacturer. This can be attractive to a Recycle PIA manufacturer that has a diversified business making a variety of products other than Recycle PIA requiring raw materials other than a reactant compound or composition that the person or entity can supply to the Recycle PIA manufacturer.

The allotment can be deposited into a recycle inventory (e.g. an inventory of allotments). In one embodiment, the allotment is an allocation created by the manufacturer of the recycle derived syngas stream. The Recycle PIA manufacturer can also make a polymer and/or article, whether or not a recycle content is applied to the polymer and/or article and whether or not recycle content, if applied to the polymer and/or article, is drawn from the inventory. For example, either the recycle derived syngas stream manufacturer and/or the Recycle PIA manufacturer may:

a. deposit the allotment into an inventory and merely store it; or
b. deposit the allotment into an inventory and apply allotments from the inventory to products other than:
   i. any products derived directly or indirectly from the recycle derived syngas stream, or
   ii. to a polymer and/or articles made by the Recycle PIA manufacturer, or
c. sell or transfer an allotment from the inventory into which at least one allotment, obtained as noted above, was deposited.

If desired, however, from that inventory, any recycle content allotment can be deducted in any amount and applied to a polymer and/or article to make a Recycle PIA. For example, a Recycle inventory of allotments can be generated having a variety of sources for creating the allotments. Some recycle content allotments (credits) can have their origin in methanolysis of recycle waste, or from mechanical recycling of waste textile and/or plastic or metal recycling, and/or from pyrolyzing recycle waste, or from any other chemical or mechanical recycling technology. The recycle inventory may or may not track the origin or basis of obtaining a recycle content value, or the inventory may not allow one to associate the origin or basis of an allotment to the allotment applied to Recycle PIA. It is sufficient that an allotment is deducted from an allotment inventory and applied to Recycle PIA regardless of the source or origin of the allotment, provided that a recycle content allotment derived from recycle textiles and/or plastics feedstock containing a fossil fuel and textile and/or plastic aggregates is present in the allotment inventory as the time of withdrawal, or a recycle content allotment is obtained by the Recycle PIA manufacturer as specified in step (i) or step (ii), whether or not that recycle content allotment is actually deposited into the inventory. In one embodiment, the recycle content allotment obtained in step (i) or (ii) is deposited into an inventory of allotments. In one embodiment, the recycle content allotment deducted from the inventory and applied to the Recycle PIA originates from recycle textiles and/or plastics or textile and/or plastic aggregates, whereby the textile and/or plastic aggregates are ultimately gasified with a fossil fuel.

As used throughout, the inventory of allotments can be owned by the recycle derived syngas manufacturer, or by the Recycle PIA manufacturer, or operated by either of them, or owned or operated by neither but at least in part for the benefit of either of them, or licensed by either of them. Also, as used throughout, the recycle derived syngas manufacturer or the Recycle PIA manufacturer may also include either of their Family of Entities. For example, while either of them may not own or operate the inventory, one among its Family of Entities may own such a platform, or license it from an independent vendor, or operate it for either of them. Alternatively, an independent entity may own and/or operate the inventory and for a service fee operate and/or manage at least a portion of the inventory for either of them.

In one embodiment, the Recycle PIA manufacturer obtains a supply of reactant compound or composition from a supplier, and also obtains an allotment from the supplier, where such allotment is derived from gasifying a feedstock containing a fossil fuel and textile and/or plastic aggregates, and optionally the allotment is associated with the reactant compound or composition supplied. In one embodiment, at least a portion of the allotment obtained by the Recycle PIA manufacturer is either:

a. applied to Recycle PIA made by the supply of reactant compound or composition;
b. applied to Recycle PIA not made by the supply of reactant compound or composition, such as would be the case where Recycle PIA is already made and stored in inventory or future made Recycle PIA; or
c. deposited into an inventory from which is deducted an allotment applied to Recycle PIA (the Recycle PIA applied allotment) and the deposited allotment either does, or does not, contribute to the amount of allotments from which the Recycle PIA applied allotment is drawn.
d. deposited into an inventory and stored.

It is not necessary in all embodiments that recycle textile and/or plastic feedstock is used to make Recycle PIA composition or that the Recycle PIA was obtained from a recycle content allotment associated with a reactant compound or composition. Further, it is not necessary that an allotment be applied to the recycle textile and/or plastic feedstock for making the Recycle PIA to which recycle content is applied. Rather, as noted above, the allotment, even if associated with a reactant compound or composition when the reactant compound or composition is obtained, can be deposited into an electronic inventory. In one embodiment, however, the reactant compound or composition associated with the allotment is used to make the Recycle PIA compound or composition. In one embodiment, the Recycle PIA is obtained from a recycle content allotment associated with textile and/or plastic aggregates, or with gasifying textile and/or plastic aggregates. In one embodiment, at least a portion of the allotments obtained from recycle textile and/or plastic made into textile and/or plastic aggregates, or the textile and/or plastic aggregates, or gasifying textile and/or plastic aggregates are applied to Recycle PIA to make a Recycle PIA.

In one embodiment, the recycle derived syngas stream manufacturer generates an allotment by gasifying a combination of a fossil fuel and textile and/or plastic aggregates, and either:

a. Applies the allotment to any compound or composition (whether liquid or solid or polymer in any form, including pellets, sheet, fibers, flake, etc.) made directly or indirectly (e.g. through a reaction scheme of several intermediates) from the recycle derived syngas stream; or b. Applies the allotment to a compound or composition not made directly or indirectly from the recycle derived syngas stream, such as would be the case where reactant compounds or compositions are already made and stored in inventory or future made non-recycle content reactant compounds or compositions; or c. deposited into an inventory from which is deducted any allotment that is applied to reactant compounds or compositions; and the deposited allotment either is or is not associated with the particular allotment applied to the reactant compounds or compositions; or d. is deposited into an inventory and stored for use at a later time.

In any of the embodiments described throughout, the timing for taking the allotment, or depositing the allotment into a recycle inventory, can be as early as when recycle textiles and/or plastics is received or owned by a Recipient or one among its Family of Entities, or when it is converted to textile and/or plastic aggregates, or when a Recipient or one among its Family of Entities receives or owns textile and/or plastic aggregates, or when they are combined with a fossil fuel, or when gasified, or when a recycle derived syngas is made. For clarification, an allotment is deemed generated or obtained by or originating from gasifying textile and/or plastic aggregates even though the timing of taking or recognizing the allotment is earlier or later than the actual time the textile and/or plastic aggregates are gasified, provided that the textile and/or plastic aggregates are subjected to gasification.

There is now also be provided a package or a combination of a Recycle PIA and a recycle content identifier associated with Recycle PIA, where the identifier is or contains a representation that the Recycle PIA contains, or is sourced from or associated with a recycle content. The package can be any suitable package for containing a polymer and/or article, such as a drum, railroad car, isotainer, totes, polytote, bale, IBC totes, compressed bale, jerrican, polybag, spools, roving, winding, or cardboard packaging. The identifier can be a certificate document, a product specification stating the recycle content, a label, a logo or certification mark from a certification agency representing that the article or package contains contents or the Recycle PIA contains, or is made from sources or associated with recycle content, or it can be electronic statements by the Recycle PIA manufacturer that accompany a purchase order or the product, or posted on a website as a statement, representation, or a logo representing that the Recycle PIA contains or is made from sources that are associated with or contain recycle content, or it can be an advertisement transmitted electronically, by or in a website, by email, or by television, or through a tradeshow, in each case that is associated with Recycle PIA. The identifier need not state or represent that the recycle content is derived from gasifying a feedstock containing a fossil fuel and textile and/or plastic aggregates. Rather, the identifier can merely convey or communicate that the Recycle PIA has or is sourced from a recycle content, regardless of the source. However, the Recycle PIA has a recycle content allotment that, at least in part, originates from gasifying textile and/or plastic aggregates.

In one embodiment, one may communicate recycle content information about the Recycle PIA to a third party where such recycle content information is based on or derived from at least a portion of the allocation or credit. The third party may be a customer of the recycle derived syngas manufacturer or Recycle PIA manufacturer or supplier, or may be any other person or entity or governmental organization other than the entity owning the either of them. The communication may electronic, by document, by advertisement, or any other means of communication.

In one embodiment, there is provided a system or package comprising:

a. Recycle PIA or article made thereby, and b. an identifier such as a credit, label or certification associated with said Recycle PIA or article made thereby, where the identifier is a representation that the polymer and/or article or article made thereby has, or is sourced from, a recycle content provided that the Recycle PIA or article made thereby has an allotment, or is made from a reactant compound or composition, at least in part originating directly or indirectly from gasifying fossil fuels and textile and/or plastic aggregates.

The system can be a physical combination, such as package having at least Recycle PIA as its contents and the package has a label, such as a logo, that the contents such as the Recycle PIA has or is sourced from a recycle content. Alternatively, the label or certification can be issued to a third party or customer as part of a standard operating procedure of an entity whenever it transfers or sells Recycle PIA having or sourced from recycle content. The identifier does not have to be physically on the Recycle PIA or on a package, and does not have to be on any physical document that accompanies or is associated with the Recycle PIA. For example, the identifier can be an electronic credit transferred electronically by the Recycle PIA manufacturer to a customer in connection with the sale or transfer of the Recycle PIA product, and by sole virtue of being a credit, it is a representation that the Recycle PIA has recycle content. The identifier itself need only convey or communicate that the Recycle PIA has or is sourced from a recycle content, regardless of the source. In one embodiment, articles made from the Recycle PIA may have the identifier, such as a stamp or logo embedded or adhered to the article. In one embodiment, the identifier is an electronic recycle content credit from any source. In one embodiment, the identifier is an electronic recycle content credit having its origin in gasifying a feedstock containing a fossil fuel and textile and/or plastic aggregates.

The Recycle PIA is made from a reactant compound or composition, whether or not the reactant is a recycle content reactant (recycle textile and/or plastic feedstock). Once a Recycle PIA composition is made, it can be designated as having recycle content based on and derived from at least a portion of the allotment, again whether or not the recycle textile and/or plastic feedstock is used to make the Recycle PIA composition. The allotment can be withdrawn or deducted from inventory. The amount of the deduction and/or applied to the Recycle PIA can correspond to any of the methods described above, e.g. a mass balance approach.

In an embodiment, a Recycle PIA compound or composition can be made by having an inventory of allotments, and reacting a reactant compound or composition a synthetic process to make a Recycle PIA, and applying a recycle content to that Recycle PIA to thereby obtain a Recycle PIA by deducting an amount of allotment from an inventory of allotments. A Recycle PIA manufacturer may have an inventory of allotments by itself or one among its Family of Entities owning, possessing, or operating the inventory, or a third party operating at least a portion of the inventory for the Recycle PIA manufacturer or its Family of Entities or as a service provided to the Recycle PIA manufacturer or one among its Family of Entities. The amount of allotment deducted from inventory is flexible and will depend on the amount of recycle content applied to the Recycle PIA. It should be at least sufficient to correspond with at least a portion if not the entire amount of recycle content applied to the Recycle PIA. The method of calculation can be a mass balance approach, or the methods of calculation described above. The inventory of allotments can be established on any basis and may be a mix of basis, provided that at least some amount of allotment in the inventory is attributable to gasifying a feedstock containing a fossil fuel and textile and/or plastic aggregates. The recycle content allotment applied to the Recycle PIA does not have to have its origin in gasifying a feedstock containing a fossil fuel and textile and/or plastic aggregates, and instead can have its origin in any other method of generating allotments from recycle waste, such as through methanolysis or gasification of recycle waste, provided that the inventory of allotments also contains an allotment or has an allotment deposit having its origin in gasifying a feedstock containing a fossil fuel and textile and/or plastic aggregates. In one embodiment, however, the recycle content applied to the Recycle PIA is an allotment obtained from gasifying a feedstock containing at least textile and/or plastic aggregates.

The following are examples of designating or declaring a recycle content to Recycle PIA or a recycle content to a reactant compound or composition:
1. A Recycle PIA manufacturer applies at least a portion of an allotment to a polymer and/or article composition where the allotment is associated with the recycle derived syngas stream, and the reactant compound or composition used to make the Recycle PIA did not contain any recycle content or it did contain recycle content; or
2. A Recycle PIA manufacturer applies at least a portion of an allotment to a polymer and/or article composition where the allotment is derived directly or indirectly with a recycle content reactant compound or composition, whether or not such reactant compound or composition volume is used to make the Recycle PIA; or
3. A Recycle PIA manufacturer applies at least a portion of an allotment to a Recycle PIA composition where the allotment is derived directly or indirectly from recycle textiles and/or plastics aggregates used to make the Recycle PIA to which the allotment is applied, and:
   a. all of the recycle content in the recycle textile and/or plastic feedstock is applied to determine the amount of recycle content in the Recycle PIA, or
   b. only a portion of the recycle content in the recycle textile and/or plastic feedstock is applied to determine the amount of recycle content applied to the Recycle PIA, the remainder stored in inventory for use to future Recycle PIA, or for application to other existing Recycle PIA made from recycle textile and/or plastic feedstock not containing any recycle content, or to increase the recycle content on an existing Recycle PIA, or a combination thereof, or
   c. none of the recycle content in the recycle textile and/or plastic feedstock is applied to the Recycle PIA and instead is stored in an inventory, and a recycle content from any source or origin is deducted from the inventory and applied to Recycle PIA; or
4. A Recycle PIA manufacturer applies at least a portion of an allotment to a reactant compound or composition used to make a Recycle PIA to thereby obtain a Recycle PIA, where the allotment was obtained with the transfer or purchase of the same reactant compound or composition used to make the Recycle PIA and the allotment is associated with the recycle content in a reactant compound or composition; or
5. A Recycle PIA manufacturer applies at least a portion of an allotment to a reactant compound or composition used to make a Recycle PIA to thereby obtain a Recycle PIA, where the allotment was obtained with the transfer or purchase of the same reactant compound or composition used to make the Recycle PIA and the allotment is not associated with the recycle content in a reactant compound or composition but rather on the recycle content of a monomer used to make the reactant compound or composition; or
6. A Recycle PIA manufacturer applies at least a portion of an allotment to a reactant compound or composition used to make a Recycle PIA to thereby obtain a Recycle PIA, where the allotment was not obtained with the transfer or purchase of the reactant compound or composition and the allotment is associated with the recycle content in the reactant compound or composition; or
7. A Recycle PIA manufacturer applies at least a portion of an allotment to a reactant compound or composition used to make a Recycle PIA to thereby obtain a Recycle PIA, where the allotment was not obtained with the transfer or purchase of the reactant compound or composition and the allotment is not associated with the recycle content in the reactant compound or composition but rather with the recycle content of any monomers used to make the reactant compound or composition; or
8. a Recycle PIA manufacturer obtains an allotment having it origin in gasifying a feedstock containing a fossil fuel and textile and/or plastic aggregates, and:
   a. no portion of the allotment is applied to a reactant compound or composition to make Recycle PIA and at least a portion is applied to Recycle PIA to make a Recycle PIA; or
   b. less than the entire portion is applied to a reactant compound or composition used to make Recycle PIA and the remainder is stored in inventory or is applied to future made Recycle PIA or is applied to existing Recycle PIA in inventory.

In one embodiment, the Recycle PIA, or articles made thereby, can be offered for sale or sold as Recycle PIA containing or obtained with recycle content. The sale or offer for sale can be accompanied with a certification or representation of the recycle content claim made in association with the Recycle PIA or article made with the Recycle PIA.

The obtaining of an allotment and designating (whether internally such as through a bookkeeping or an inventory tracking software program or externally by way of declaration, certification, advertising, representing, etc.) can be by the Recycle PIA manufacturer or within the Recycle PIA manufacturer Family of Entities. The designation of at least a portion of the Recycle PIA as corresponding to at least a portion of the allotment (e.g. allocation or credit) can occur through a variety of means and according to the system employed by the Recycle PIA manufacturer, which can vary from manufacturer to manufacturer. For example, the designation can occur internally merely through a log entry in the books or files of the Recycle PIA manufacturer or other inventory software program, or through an advertisement or statement on a specification, on a package, on the product, by way of a logo associated with the product, by way of a certification declaration sheet associated with a product sold, or through formulas that compute the amount deducted from inventory relative to the amount of recycle content applied to a product.

Optionally, the Recycle PIA can be sold. In one embodiment, there is provided a method of offering to sell or selling polymer and/or articles by:
- a. A Recycle PIA manufacturer or its Family of Entities obtaining or generating a recycle content allotment, and the allotment can be obtained by any of the means described herein and can be deposited into inventory, the recycle content allotment having its origin in recycle textiles and/or plastics made into textile and/or plastic aggregates or in the textile and/or plastic aggregates,
- b. converting a reactant compound or composition in a synthetic process to make a compound, composition, polymer and/or article composition,
- c. designating (e.g. assigning or associating) a recycle content to at least a portion of the compound, composition, polymer and/or article composition from an inventory of allotments, where the inventory contains at least one entry that is an allotment associated with gasification of a feedstock containing textile and/or plastic aggregates. The designation can be the amount of allotment deducted from inventory, or the amount of recycle content declared or determined by the Recycle PIA manufacturer in its accounts. Thus, the amount of recycle content does not necessarily have to be applied to the Recycle PIA product in a physical fashion. The designation can be an internal designation to or by the Recycle PIA manufacturer or its Family of Entities or a service provider in contractual relationship to the Recycle PIA manufacturer or its Family of Entities, and
- d. offering to sell or selling the compound, composition, polymer and/or article composition as containing or obtained with recycle content corresponding at least in part with such designation. The amount of recycle content represented as contained in the Recycle PIA sold or offered for sale has a relationship or linkage to the designation. The amount of recycle content can be a 1:1 relationship in the amount of recycle content declared on a Recycle PIA offered for sale or sold and the amount of recycle content assigned or designated to the Recycle PIA by the Recycle PIA manufacturer.

The steps described need not be sequential, and can be independent from each other. For example, the step a) of obtaining an allotment and the step of making Recycle PIA from a reactant compound or composition can be simultaneous.

As used throughout, the step of deducting an allotment from an inventory of allotments does not require its application to a Recycle PIA product. The deduction also does not mean that the quantity disappears or is removed from the inventory logs. A deduction can be an adjustment of an entry, a withdrawal, an addition of an entry as a debit, or any other algorithm that adjusts inputs and outputs based on an amount recycle content associated with a product and one or a cumulative amount of allotments on deposit in the inventory. For example, a deduction can be a simple step of a reducing/debit entry from one column and an addition/credit to another column within the same program or books, or an algorithm that automates the deductions and entries/additions and/or applications or designations to a product slate. The step of applying an allotment to a Recycle PIA product where such allotment was deducted from inventory also does not require the allotment to be applied physically to a Recycle PIA product or to any document issued in association with the Recycle PIA product sold. For example, a Recycle PIA manufacturer may ship Recycle PIA product to a customer and satisfy the "application" of the allotment to the Recycle PIA product by electronically transferring a recycle content credit to the customer.

In one embodiment, the amount of recycle content in the recycle textile and/or plastic feedstock or in the Recycle PIA will be based on the allocation or credit obtained by the manufacturer of the Recycle PIA composition or the amount available in the Recycle PIA manufacturer's inventory of allotments. A portion or all of the allocation or credit obtained by or in the possession of a manufacturer of Recycle PIA can be designated and assigned to recycle textiles and/or plastics feedstock or Recycle PIA on a mass balance basis. The assigned value of the recycle content to the recycle textile and/or plastic feedstock or Recycle PIA should not exceed the total amount of all allocations and/or credits available to the manufacturer of the Recycle PIA or other entity authorized to assign a recycle content value to the Recycle PIA.

There is now also provided a method of introducing or establishing a recycle content in a compound, composition, polymer and/or article without necessarily using reactant compound or composition having recycle content. In this method,
- a. a syngas manufacturer makes recycle derived syngas stream and
- b. a polymer and/or article manufacturer:
    - i. obtains an allotment associated with gasifying textile and/or plastic aggregates,
    - ii. makes a polymer and/or article from any reactant compound or composition, and
    - iii. associates at least a portion of the allotment with at least a portion of the polymer and/or article, whether or not the reactant compound or composition used to make the polymer and/or article contains a recycle content.

In this method, the polymer and/or article manufacturer need not purchase a recycle reactant compound or composition from a particular source or supplier, and does not require the polymer and/or article manufacturer to use or purchase a reactant compound or composition having recycle content in order to successfully establish a recycle content in the polymer and/or article composition. The polymer or article manufacturer may use any source of reactant compound or composition and apply at least a portion of the allocation or credit to at least a portion of the reactant compound or composition feedstock or to at least a portion of the polymer and/or article product. The association by the polymer and/or article manufacturer may come in any form, whether by on in its inventory, internal accounting methods, or declarations or claims made to a third party or the public.

There is also provided a use for a reactant compound or composition, the use including converting textile and/or plastic aggregates in any synthetic process, such as gasification, to make syngas and/or Recycle PIA.

There is also provided a use for recycle textiles and/or plastics and/or plastic aggregates that includes converting a reactant compound or composition in a synthetic process to make polymer and/or articles and applying at least a portion of an allotment to the polymer and/or article to the reactant compound or composition, where the allotment is associated with gasifying a feedstock containing a fossil fuel and textile and/or plastic aggregates or has its origin in an inventory of allotments where at least one deposit made into the inventory is associated with gasifying a feedstock containing a fossil fuel and recycle textile and/or plastic aggregates.

In one embodiment, there is provided a polymer and/or article composition that is obtained by any of the methods described above.

The reactant compound or composition, such a reactant compound or composition can be stored in a storage vessel and transferred to a Recycle PIA manufacturing facility by way of truck, pipe, or ship, or as further described below, the reactant compound or composition production facility can be integrated with the Recycle PIA facility. The reactant compound or composition may be shipped or transferred to the operator or facility that makes the polymer and/or article.

In an embodiment, the process for making Recycle PIA can be an integrated process. One such example is a process to make Recycle PIA by:
  a. gasifying a feedstock containing a fossil fuel and recycle textile and/or plastic aggregates to make a recycle derived syngas stream; and
  b. reacting said recycle derived syngas or a non-recycle derived syngas made in the gasifier in a reaction scheme to make a reactant compound or composition;
  c. reacting any reactant compound or composition in a synthetic process to make a polymer and/or article;
  d. depositing an allotment into an inventory of allotments, said allotment originating from gasifying a feedstock containing a fossil fuel and recycle textile and/or plastic aggregates; and
  e. applying any allotment from said inventory to the polymer and/or article to thereby obtain a recycle content polymer and/or article composition.

In one embodiment, one may integrate two or more facilities and make Recycle PIA. The facilities to make Recycle PIA, the reactant compound or composition, or the syngas can be stand-alone facilities or facilities integrated to each other. For example, one may establish a system of producing and consuming a reactant compound or composition, as follows:
  a. provide a reactant compound or composition manufacturing facility configured to produce a reactant compound or composition;
  b. provide a polymer and/or article manufacturing facility having a reactor configured to accept a reactant compound or composition from the reactant compound or composition manufacturing facility and making a polymer and/or article; and
  c. a supply system providing fluid communication between these two facilities and capable of supplying a reactant compound or composition from the reactant compound or composition manufacturing facility to the polymer and/or article manufacturing facility,
wherein the reactant compound or composition manufacturing facility generates or participates in a process to generate allotments and gasifies a feedstock containing fossil fuel and recycle textile and/or plastic aggregates, and:
  1. said allotments are applied to the reactants compounds or compositions or to the polymer and/or article reactant, or
  2. are deposited into an inventory of allotments, and any allotment is withdrawn from the inventory an applied to the reactant compounds or compositions or to the polymer and/or article.

The reactant compound or composition manufacturing facility can make Recycle PIA by accepting any reactant compound or composition from the reactant compound or composition manufacturing facility and applying a recycle content to a polymer and/or article made with the reactant compound or composition by deducting allotments from its inventory and applying them to the Recycle PIA, optionally in amounts using the methods described above. The allotments withdrawn from inventory and applied can be allotments obtained by any source of recycle content, and need not necessarily be allotments associated with gasifying textile and/or plastic aggregates.

In one embodiment, there is also provided a system for producing Recycle PIA as follows:
  a. provide a gasification manufacturing facility configured to produce an output composition comprising a recycle textile or plastic derived syngas stream;
  b. provide a reactant compound or composition manufacturing facility configured to accept recycle derived syngas stream from the gasification manufacturing facility and making, through a reaction scheme one or more downstream products of said syngas to make an output composition comprising a reactant compound or composition;
  c. provide a polymer and/or article manufacturing facility having a reactor configured to accept a reactant compound or composition and making an output composition comprising a recycle content Recycle PIA; and
  d. a supply system providing fluid communication between at least two of these facilities and capable of supplying the output composition of one manufacturing facility to another one or more of said manufacturing facilities.

The polymer and/or article manufacturing facility can make Recycle PIA. In this system, the gasification manufacturing facility can have its output in fluid communication with the reactant compound or composition manufacturing facility which in turn can have its output in fluid communication with the polymer and/or article manufacturing facility. Alternatively, the manufacturing facilities of a) and b) alone can be in fluid communication, or only b) and c). In the latter case, the polymer and/or article manufacturing facility can make Recycle PIA directly by having the recycle textile and/or plastic content syngas produced in the gasification manufacturing facility converted all the way to Recycle PIA, or indirectly by accepting any reactant compound or composition from the reactant compound or composition manufacturing facility and applying a recycle content to Recycle PIA by deducting allotments from its inventory and applying them to the Recycle PIA, optionally in amounts using the methods described above. The allotments obtained and stored in inventory can be obtained by any of the methods described above, The fluid communication can be gaseous or liquid or both. The fluid communication need not be continuous and can be interrupted by storage tanks, valves, or other purification or treatment facilities, so long as the fluid can be transported from the manufacturing facility to the subsequent facility through an interconnecting pipe network and without the use of truck, train, ship, or airplane. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment, the integrated process includes at least two facilities co-located within 5, or within 3, or within 2, or within 1 mile of each other (measured as a straight line). In one embodiment, at least two facilities are owned by the same Family of Entities.

In an embodiment, there is also provided an integrated Recycle PIA generating and consumption system. This system includes:
a. Provide a gasification manufacturing facility configured to produce an output composition comprising recycle derived syngas stream obtained by gasifying fossil fuel and recycle textile and/or plastic aggregates;
b. provide a reactant compound or composition manufacturing facility configured to accept a recycle derived syngas stream from the gasification manufacturing facility and making, through a reaction scheme, one or more downstream products of said syngas to make an output composition comprising a reactant compound or composition;
c. provide a polymer and/or article manufacturing facility having a reactor configured to accept said reactant compound or composition and making an output composition comprising a polymer and/or article; and
d. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. For example, the recycle derived syngas can be delivered to the reactant compound or composition facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the reactant compound or composition reactor or the cracker, but rather to a delivery and receiving point at the respective facilities. The interconnecting pipework need not connect all three facilities to each other, but rather the interconnecting pipework can be between facilities a)-b), or b)-c), or between a)-b)-c).

In embodiments, the total amount of carbon in the textile and/or plastic aggregate is at least 60 wt. %, or at least 70 wt. %, or at least 75 wt. %, or at least 80 wt. %.

In embodiments, the total amount of hydrogen in the densified textiles and/or plastics is desirably at least 5 wt. %, or at least 8 wt. %, or at least 10 wt. %.

In another embodiment, the ratio of total hydrogen to total carbon in the textile and/or plastic aggregates feed is higher than that of the other source of fuel. In embodiments, the ratio of total hydrogen to total carbon in the textiles and/or plastics is higher than that of any other source of fuel fed to the gasifier. In embodiments, the ratio of total hydrogen to total carbon in the textile and/or plastic aggregates used in the gasifier feedstock is at least 0.075, or at least 0.08, or at least 0.085, or at least 0.09, or at least 0.095, or at least 0.1, or at least 0.11, or at least 0.12, or at least 0.13 by weight.

In embodiments, the textiles and/or plastics aggregates used in the feedstock composition have an average fixed carbon content that is less than the solid fossil fuel used in the one or more first feedstock streams, or less than 75 wt. %, or not more than 70 wt. %, or not more than 65 wt. %, or not more than 60 wt. %, or not more than 55 wt. %, or not more than 45 wt. %, or not more than 40 wt. %, or not more than 35 wt. %, or not more than 30 wt. %, or not more than 25 wt. %, or not more than 20 wt. %, or not more than 15 wt. %, or not more than 10 wt. %, or not more than 8 wt. %, or not more than 6 wt. %, or not more than 5 wt. %, or not more than 4 wt. %, or not more than 3 wt. %, or not more than 2 wt. %, or not more than 1 wt. %, based on the weight of the textiles and/or plastics. The fixed carbon content is the combustible solids remaining (other than ash) after the material is heated and volatiles removed. It can be determined by subtracting the percentages of moisture, volatile matter, and ash from a sample.

In embodiments, the textiles and/or plastics used in the gasifier feedstock composition have an average fixed carbon content that is at least 3% less, or at least 5% less, or at least 7% less, or at least 9% less, or at least 10% less, or at least 13% less, or at least 15% less, or at least 17% less, or at least 20% less, or at least 23% less, or at least 25% less, or at least 27% less, or at least 30% less, or at least 32% less, or at least 35% less, or at least 38% less, or at least 40% less, or at least 43% less, or at least 45% less, or at least 47% less, or at least 50% less, or at least 55% less, or at least 60% less, or at least 70% less, or at least 80% less, or at least 90% less, or at least 95% less, than the fixed carbon content of coal, or optionally all solid fossil fuel employed in the feedstock composition, or optionally any solids other that textile and/or plastic aggregates, or any other fuel fed to the gasifier.

The textile and/or plastic aggregates can have an average sulfur content that is fairly sizable since the high temperature or slagging gasifiers are well equipped to handle sulfur, although in practice textiles and/or plastics have a very low or only trace amounts of sulfur. The textile and/or plastic aggregates can have an average sulfur content of up to 1 wt. %, or up to 0.5 wt. %, or up to 0.25 wt. %, or up to 0.1 wt. %, or up to 0.05 wt. %, or up to 0.01 wt. %, or up to 0.005 wt. %, or up to 0.0001 wt. %, based on the weight of the textile and/or plastic aggregates.

The textile and/or plastic aggregates may have a widely varying ash content depending on the type of textile and/or plastic they are made from and the purity the textile and/or plastic aggregates stream to the select textile and/or plastic aggregates. The textile and/or plastic aggregates may have an average ash content of at least 1 wt. %, or at least 2 wt. %, or at least 3 wt. %, or at least 4 wt. %, or at least 5 wt. %, or at least 5.5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. % based on the weight of the textile and/or plastic aggregates. The textile and/or plastic aggregates may have an average ash content of not more than 60 wt. %, or not more than 55 wt. %, or not more than 55 wt. %, or not more than 55 wt. %, or not more than 55 wt. %, or not more than 40 wt. %, or not more than 30 wt. %, or not more than 20 wt. %, or not more than 15 wt. %, or not more than 10 wt. %, desirably not more than 8 wt. %, or not more than 7 wt. %, or not more than 6 wt. %, or not more than 5.5 wt. %, or not more than 5 wt. %, or not more than 4.5 wt. %, or not more than 4 wt. %, or not more than 3 wt. %, or not more than 2.5 wt. %, based on the weight of the textile and/or plastic aggregates.

In embodiments, the average oxygen content in the textile and/or plastic aggregates can be at zero or at least 0.1 wt. %, or at least 0.5 wt. %, or at least 1 wt. %, or at least 2 wt. %, or at least 4 wt. %, or at least 6 wt. %, or at least 8 wt. %, or at least 10 wt. %, or at least 13 wt. %, or at least 15 wt. %, or at least 18 wt. %, or at least 20 wt. %, based on the weight of the textile and/or plastic aggregates. Desirably, to improve the HHV, the amount of oxygen is kept low, such as not more than 20 wt. %, or not more than 15 wt. %, or not more than 10 wt. %, or not more than 8 wt. %, or not more than 5 wt. %, or not more than 4 wt. %, or not more than 2 wt. %, or not more than 1 wt. %, based on the weight of the textile and/or plastic aggregates.

The content of minerals, metals and elements other than carbon, hydrogen, oxygen, nitrogen, and sulfur, in the textile and/or plastic aggregates can be at least 0.01 wt. %, or at least 0.1 wt. %, or at least 0.5 wt. %, or at least 1 wt. %, or at least 1.5 wt. %, or at least 1.8 wt. %, or at least 2 wt. %, or at least 2.3 wt. %, or at least 2.5 wt. %, or at least 2.8 wt. %, or at least 3 wt. %, based on the weight of the textile and/or plastic aggregates. The upper amount is not particularly limited, and generally would not exceed 8 wt. %, or not exceed 7 wt. %, or not exceed 6 wt. %, or not exceed 5 wt. %, or not exceed 4.5 wt. %, or not exceed 4 wt. %, or not exceed 3.8 wt. %.

If a large amount of textile and/or plastic aggregates is employed, which have a large mismatch in fixed carbon content compared to the fossil fuel used, variations in the syngas composition can be experienced outside of desirable limits. For example, a textile and/or plastic aggregate solid that has a very low fixed carbon content could, in an entrainment flow high temperature gasifier, gasify more readily than coal and proceed to generate more carbon dioxide within the residence time experienced by coal, while a co-feed of solids having a much higher fixed carbon content that coal would take longer to gasify and generate more unconverted solids The degree of syngas compositional variations that can be tolerated will depend on the use of the syngas, and in the case of making chemicals, it is desirably to minimize the factors that could cause wider syngas compositional variations. In the gasification process, there is one or more first feedstock streams fed to a gasifier during a first time period, and one or more second feedstock stream fed to the same gasifier during a second time period. At least one of the one or more first feedstock streams contain a solid fossil fuel and may or may not also contain textiles and/or plastics. At least one of the one or more second feedstock streams contain textiles and/or plastics. The amount by weight of textiles and/or plastics fed to the gasifier during the second time period is more than the amount by weight of textiles and/or plastics fed to the same gasifier during the first time period, based on the weight of all gasifier fuel fed to the gasifier.

The one or more first feedstock streams fed to the gasifier contain a solid fossil fuel fed to the gasifier during a first time period, and one or more of those streams may optionally contain textiles and/or plastics. In embodiments, the amount of solid fossil fuel, such as coal, in the one or more first feedstock streams can be at least at least 80 wt. %, or at least 85 wt. %, or at least 90 wt. %, or at least 93 wt. %, or at least 95 wt. %, or at least 97 wt. %, or at least 98 wt. %, or at least 98.5 wt. %, or at least 99 wt. %, and less than 100 wt. %, or less than 99.5 wt. %, based on the weight of solids in the one or more first feedstock streams or based on the weight of all gasifier fuel in the one or more first feedstock streams.

During the first time period, the gasifier is operated to optimize conditions effective to produce a consistent high-quality syngas with minimal char or carbon dioxide production from a fossil fuel feedstock. In many cases, the chemical production is based on a syngas composition and consistency generated from operating conditions designed for processing the fossil fuel feedstock. However, the gasification operating conditions during the first time period can tolerate the use of plastic and/or textile feedstocks in a form and in amounts that do not disrupt the operations or syngas composition and consistency to the point where the syngas disrupts production of chemicals.

Since textiles and/or plastics have, on average, a much lower fixed carbon content than solid fossil fuels, the amount of carbon dioxide they generate will be more than, and the amount of carbon monoxide they generate in the syngas discharged from the reactor will be lower than, that of the solid fossil fuels at the same residence time as the solid fossil fuels in the gasification zone and on the same weight basis when operating at conditions effective to gasify fossil fuels that favor CO production over carbon dioxide. Accordingly, the amount of the textiles and/or plastics fed to the gasifier in the one or more first feedstock streams or during the first time period are low to obtain the advantage of minimizing the increase in carbon dioxide content or depletion of carbon monoxide content or the CO/hydrogen ratio. While the exact amount of plastics or textiles that can be tolerated without disrupting the production of chemicals is dependent on the kind of fossil fuel being gasified, the gasifier design being a dry feed or slurry feed, the operating conditions, and the downstream purification sections, the amount of textiles and/or plastics fed to the gasifier in the one or more first feedstock streams or during the first time period will be lower than the amount fed during the second time period or in the one or more second feedstock streams. The amount of plastics and/or textiles fed to the gasifier during the second time period or contained in the one or more second feedstock streams can be at least 20% higher, or at least 40% higher, or at least 50% higher, or at least 70% higher, or at least 80% higher, or at least 100% higher, or at least 130% higher, or at least 150% higher, or at least 175% higher, or at least 200% higher, or at least 225% higher, or at least 250% higher, or at least 275% higher, or at least 300% higher, or at least 350% higher, or at least 400% higher, or at least 500% higher, or at least 600% higher, or at least 700% higher, or at least 800% higher, or at least 900% higher, or at least 1000% higher, or at least 1250% higher, or at least 1500% higher, or at least 1750% higher, or at least 2000% higher, or at least 2500% higher, or at least 3000% higher, or at least 4000% higher than the amount fed to the gasifier during the first time period or in the one or more first feedstock streams, on a weight basis and based on the weight of all fuel fed to the gasifier. For example, plastics and/or textiles fed to the gasifier in an amount of 50 wt. % during the second time period would be 2400% higher than plastics and/or textiles fed to the gasifier during the first time period or in one or more first feedstock streams at 2 wt. %: (50−2)/2×100.

In embodiments, the amount of textiles and/or plastics relative to all sources of fuel (solid, liquid or gas) fed to the gasifier in the one or more first feedstock streams or during the first time period is not more than 10 wt. %, or not more than 9 wt. %, or not more than 8 wt. %, or not more than 7 wt %, or not more than 6 wt. %, or not more than 5 wt. %, or not more than 4 wt. %, or not more than 3.5 wt. %, or not more than 3 wt. %, or not more than 2.75 wt. %, or not more than 2.5 wt. %, or not more than 2.25 wt. %, or not more than 2 wt. %, or not more than 1.75 wt. %, or not more than 1.5 wt. %, or not more than 1.25 wt. %, or not more than 1 wt. %, based on the weight of all gasifier fuel fed to the gasifier (and fuel does not include the oxidizer, steam, water, or carbon dioxide gas). Examples of the content of textiles and/or plastics present in the one or more first feedstock stream composition include 0.25 wt. % to less than 5 wt. %, or from 0.25 wt. % to 4 wt. %, or from 0.25 wt. % to 3 wt. %, or from 0.25 wt. % to 2.5 wt. %, or from 0.5 wt. % to 5 wt. %, or from 0.5 wt. % to 4 wt. %, or from 0.5 wt. % to 3 wt. %, or from 0.5 wt. % to 2.5 wt. %, or from 1 wt. % to 5 wt. %, or from 1 wt. % to 4 wt. %, or from 1 wt. % to 3 wt. %, or from 1 wt. % to 2.5 wt. % each based on the weight of the fuel in the first feedstock streams fed to the gasifier.

The production of a high concentrated recycle polymer derived syngas during the first period of time can extend for as long as one desires. The first period of time and the second period of time can be the same time periods or different time period. In embodiments, the second time period is shorter than the first time period. For example, the second time period is shorter than the first time period by at least one day, or by at least 7 days, or by at least 14 days, or by at least 30 days, or by at least 60 days, or by at least 90 days, or by at least 120 days, or by at least 160 days, or by at least 240 days, or by at least 280 days, or by at least 300 days, or by at least 320 days, or by at least 330 days, or by at least 340 days.

The second time period begins when gasifier textiles and/or plastics are added to a feedstock stream and gasified and one or more conditions are present:
  a. the gasification temperature is lowered by at least 50° C., or
  b. the amount of textiles and/or plastics fed to the gasifier is more than 10 wt. %, or any of the amount stated below, based on the weight of all fuel fed to the gasifier.

In embodiments, the amount of textiles and/or plastics present in the one or more second feedstock streams fed to the gasifier or during at least a portion the second time period are more than more than 10 wt. %, or more than 15 wt. %, or more than 20 wt. %, or more than 25 wt. %, or more than 30 wt. %, or more than 35 wt. %, or more than 40 wt. %, or more than 45 wt. %, or more than 50 wt. %, or more than 55 wt. %, or more than 60 wt. %, or more than 65 wt. %, or more than 70 wt. %, or more than 75 wt. %, or more than 80 wt. %, or more than 85 wt. %, or more than 90 wt. %, or more than 95 wt. %, or more than 97 wt. %, or more than 98 wt. %, or more than 99 wt. %, or even 100 wt. %, based on the weight of all fuel fed to the gasifier during the second time period.

In embodiments, the amount of solid fossil fuel, such as coal, in the one or more second feedstock streams fed to the gasifier can be zero, or not more than 1 wt. %, or not more than 2 wt. %, or not more than 3 wt. %, or not more than 5 wt. %, or not more than 10 wt. %, or not more than 15 wt. %, or not more than 20 wt. %, or not more than 25 wt. %, or not more than 30 wt. %, or not more than 35 wt. %, or not more than 40 wt. %, or not more than 45 wt. %, or not more than 50 wt. %, or not more than 55 wt. %, or not more than 60 wt. %, or not more than 65 wt. %, or not more than 70 wt. %, or not more than 75 wt. %, or not more than 80 wt. %, or not more than 85 wt. %, or not more than 90 wt. %, based on the weight of solids in the one or more second feedstock stream or based on the weight of all gasifier fuel in the one or more second feedstock streams.

The transition from the first time period to the second time period can be abrupt, such as the addition of the plastics and/or textiles and discontinuing feeding the same amounts of fossil fuel all in one day (or within 6 hours) or gradually over two or more days or over a week or two weeks. The changeover of fuel during transition can be accompanied by a shutdown of fuel feedstock supply to the gasifier or desirably is conducted by the continuous feed of fuel of fuel to the gasifier during the feedstock changeover. During the transition period, the change in gasifier process conditions, and particularly the gasification temperature, are desirably coordinated with and correspond to the rate of textile and/or plastics addition to the feedstock stream.

The designation of one or more first feedstock streams and one or more second feedstock streams does not imply the use of different physical equipment between the two, or different feed locations, or imply any difference at all between the two, other than the relative amount of textiles and/or plastics will be different. While other physical differences can exist, they are not implied by the use of the terms first feedstock and second feedstock. In embodiments, the same feedstock train or lines, or the same feed locations, or the same injector devices are used for the first and second feedstocks. In embodiments, a different line than used to feed fossil fuel during the first time period can be installed and/or used in as the one or more second feedstocks to the gasifier, optionally and desirably fed to the same location and/or through the same injector. If desired, one or more second feedstock stream can be fed to a second and different location on the gasifier than the feed location for the one or more first feedstock stream.

The same gasifier is used to feed the first and second feedstock streams.

In the second feedstock stream or during the second time period, the amount of textiles and/or plastics fed to the gasifier will be high. During the second time period, the gasifier is operated under one or more conditions that are different from the conditions during the first time period. In embodiments, the gasifier conditions during the second time period are optimized for a low conversion to carbon dioxide and for the production of carbon monoxide. Since textiles and/plastics contain very low amount of fixed carbon, if any, the gasification temperature will be lower to minimize carbon dioxide production, and under those conditions, the presence of fossil fuel in the gasification zone can lead to incomplete gasification and generation of char. To minimize the production of char, desirably the amount of fossil fuel fed to the gasifier in the one or more second feedstock streams or during the second time period is lower than the amount fed in the one or more first feedstock streams or during the first time period. Desirably, the amount of fossil fuel fed to the gasifier in the one or more second feedstock streams or during at least a portion of the second time period is not more than 80 wt. %, or not more than 70 wt. %, or not more than 60 wt. %, or not more than 50 wt. %, or not more than 40 wt. %, or not more than 30 wt. %, or not more than 20 wt. %, or not more than 10 wt. %, or not more than 5 wt. %, or not more than 2 wt. %, or not more than 1 wt. %, or none at all, based on the weight of all solid fuel fed to the gasifier in the one or more second feedstock streams or during the second time period.

To minimize the production of carbon dioxide and maximize the production of carbon monoxide, at least one process condition in the gasifier is different: the gasification temperature during at least a portion of the second time period is lower than the gasification temperature during the first time period. The gasification temperature during the first time period is determined as the first continuous 2-month average operating temperature within gasification zone preceding the second time period during which solid fossil fuel is fed to the gasifier in an amount of at least 95 wt. % based on the weight of all solid fuel fed to the gasifier. The gasification temperature in the second time period is also determined as an average over any continuous portion of time that represents at least 30% of the second time period, or at least 50% of the second time period, or at least 70% of the second time period, or at least 90% of the second time period. Sudden unusual spikes or drops in temperature not normally encountered during steady state operations are discounted when determining an average temperature during the first and second time periods.

In embodiments, the gasification temperature during the second time period at least 25° C. less than the gasification temperature during the first time period, or at least 35° C., or at least 45° C., or at least 60° C., or at least 80° C., or at least 100° C., or at least 125° C., or at least 150° C., or at least 175° C., or at least 200° C., or at least 225° C., or at least 250° C., or at least 275° C., or at least 300° C., or at least 325° C., or at least 350° C., or at least 375° C., or at least 400° C.

To avoid the formation of tar and inordinate amounts of char, the temperature of the gasification zone fed with one or more second feedstocks or during at least a portion of the second time period is maintained at or above the ash fusion temperature of the plastics and/or textiles.

In embodiments, the gasification conditions and feedstock composition during the first time period are effective to generate a molten slag in the gasification zone. Since the plastics and/or textiles may have lower amounts of incombustible elements such as metals and minerals, the amount of slag produced during at least a portion of the second time period is less than the amount produced during the first time period on a daily basis over a 12-day period or the second time period, whichever is shorter. In embodiments, the amount of slag produced during at least a portion of the second time period is at least 10% less, or at least 20% less, or at least 40% less, or at least 60% less, or at least 80% less, or at least 90% less than the amount produced during the first time period. In embodiments, no slag is produced during at least a portion of the second time period. The amount of slag produced can be determined by weighing the solid slag discharged from the gasifier.

Since textiles and/or plastics will have a higher thermal energy demand than coal to gasify, the temperature within the gasification zone at high concentrations can drop lower than desired, below the amount that minimized char formation and even below the ash fusion temperature. To avoid a net thermal energy input, and minimize the temperature drop beyond that desired, the free oxygen:carbon molar ratio can be increased while remaining below the gasification temperature employed in the first time period. In embodiments, the O:C ratio (O being free oxygen) is increased when feeding the one or more second feedstocks or during at least during a portion of the second time period relative to the 0:0 ratio used when feeding the one or more first feedstocks or during at least a portion of the first time period. Such time periods can be determined the same way and for the same time periods as used to determine the average temperatures. The 0:0 ratio when feeding the one or more second feedstocks or during at least during a portion of the second time period, relative to the 0:0 ratio used when feeding the one or more first feedstocks or during at least a portion of the first time period, can be increased by at least 5%, or at least 10%, or at least 12%, or at least 15%, or at least 20%, or at least 25%, or at least 30%.

With many gasifier designs, the fossil fuel (coal or petcoke) and the textiles and/or plastics are size reduced for multiple purposes. The textiles and/or plastics are of a small size as is the fossil fuel source to (i) allow for faster reaction once inside the gasifier due to mass transfer limitations, (ii) to create a slurry that is stable, fluid and flowable at high concentrations of solids to water in slurry fed gasifiers, (iii) to pass through processing equipment such as high-pressure pumps, valves, and feed injectors that have tight clearances, (iv) to flow through screens between the mills or grinders and the gasifier, (vi) to have sufficient density to allow them to form a stable bed or (v) to be conveyed with gases used for conveying solid fossil fuels to dry fed gasifiers.

The form of the textiles and/or plastics feedstocks used to make high concentrated recycle polymer and/or plastics as gasifier feedstocks are not limited, and can include any of the forms of articles or materials used to make textiles described above; e.g. fibers, yarns, fabrics, cloths, finished article forms, or pieces thereof, and for plastics, and can include sheets, extruded shapes, moldings, films, laminates, and foamed, each of varying age and composition The size of the textiles and/or plastics are desirably not larger than the maximum size the gasifier in use can accept. Many coal fed gasifiers can grind or mill the coal to a desired size before feeding them to the gasification zone, particularly with respect to plastics feeds.

The actual particle size of the textiles and/or plastics and textile and/or plastic aggregates can vary with the type of gasifier used. For example, textiles and/or plastics and their aggregates having an average particle size of ¼ inch or less in their largest dimension cannot be processed through an entrained flow coal gasifier. However, fixed bed or moving bed gasifiers can accept larger particle sizes. Examples of suitable sizes of textiles and/or plastics and their aggregates fed to a fixed bed or moving bed gasifier are not more than 12 inches, or not more than 8 inches, or not more than 6 inches, or not more than 5 inches, or not more than 4 inches, or not more than 3.75 inches, or not more than 3.5 inches, or not more than 3.25 inches, or not more than 3 inches, or not more than 2.75 inches, or not more than 2.5 inches, or not more than 2.25 inches, or not more than 2 inches, or not more than 1.75 inches, or not more than 1.5 inches, or not more than 1.25 inches. The size can be at least 2 mm, or at least ⅛ inches, or at least ¼ inches, or at least ½ inches, or at least 1 inch, or at least 1.5 inches, or at least 1.75 inches, or at least 2 inches, or at least 2.5 inches, or at least 3 inches, or at least 3.5 inches, or at least 4 inches, or at least 4.5 inches, or at least 5 inches, or at least 5.5 inches. Such relatively large textile and/or plastic aggregates are better suited for use in fixed or moving bed gasifiers, especially those that are updraft fixed or moving bed gasifiers.

With many gasifier designs, the fossil fuel (coal or petcoke) and the textile and/or plastic aggregates are size reduced for multiple purposes. The textile and/or plastic aggregates are of a small size as is the fossil fuel source to (i) allow for faster reaction once inside the gasifier due to mass transfer limitations, (ii) to create a slurry that is stable, fluid and flowable at high concentrations of solids to water in slurry fed gasifiers, (iii) to pass through processing equipment such as high-pressure pumps, valves, and feed injectors that have tight clearances, (iv) to flow through screens between the mills or grinders and the gasifier, or (v) to be conveyed with gases used for conveying solid fossil fuels to dry fed gasifiers.

In embodiments, the textile and/or plastics and their aggregate particle sizes are desirably not more than 5 inches, or not more than 4 inches, or not more than 1 inch, or not more than ¼ inch, or not more than 2 mm. The larger sizes are useful for addition to a fixed bed or moving bed gasifier, particularly in updraft gasifiers to provide sufficient density to allow them to contact the bed as a solid that has not fully charred or be converted to ash.

In embodiments, the solids in the gasifier feedstock, including the textiles and/or plastics and their aggregates, have a particle size of 2 mm or smaller. This embodiment is particularly attractive to entrained flow gasifiers, including dry feed and slurry fed gasifiers, and to fluidized bed gasifiers. As used throughout, unless a different basis is expressed (e.g. a mean), a stated size means that at least 90 wt. % of the textiles and/or plastics particles have a largest dimension in the stated size, or alternatively that 90 wt. % of the textiles and/or plastics pass through sieve designated for that particle size. Either conditions satisfy the particle size designation. Textiles and/or plastics and their aggregates sized larger than 2 mm for an entrained flow gasifier have the potential for being blown through the gasification zone of entrained flow gasifiers without completely gasifying, particularly when the gasification conditions are established to gasify solid fossil fuel having a particle dimension of 2 mm or smaller.

In embodiments, the size of the textiles and/or plastics as such or as combined with a fossil fuel, or in the gasifier feed, or injected into the gasification zone, is 2 mm or smaller or constitute those particles passing through a 10 mesh, or 1.7 mm or smaller (those particles passing through a 12 mesh), or 1.4 mm or smaller (those particles passing through a 14 mesh), or 1.2 mm or smaller (those particles passing through a 16 mesh), or 1 mm or smaller (those particles passing through a 18 mesh), or 0.85 mm or smaller (those particles passing through a 20 mesh), or 0.7 mm or smaller (those particles passing through a 25 mesh) or 0.6 mm or smaller (those particles passing through a 30 mesh), or 0.5 mm or smaller (those particles passing through a 35 mesh), or 0.4 mm or smaller (those particles passing through a 40 mesh), or 0.35 mm or smaller (those particles passing through a 45 mesh), or 0.3 mm or smaller (those particles passing through a 50 mesh), or 0.25 mm or smaller (those particles passing through a 60 mesh), or 0.15 mm or smaller (those particles passing through a 100 mesh), or 0.1 mm or smaller (those particles passing through a 140 mesh), or 0.07 mm or smaller (those particles passing through a 200 mesh), or 0.044 mm or smaller (those particles passing through a 325 mesh), or 0.037 mm or smaller (those particles passing through a 400 mesh). In embodiments, the size of the textiles and/or plastics particles is at least 0.037 mm (or 90% retained on a 400 mesh).

In embodiments, the bulk density of the textiles and/or plastics after final grinding is within 150%, or within 110%, or within 100%, or within 75%, or within 60%, or within 55%, or within 50%, or within 45%, or within 40%, or within 35% of the bulk density of the ground fossil fuel that is used as a feed introduced to the gasification zone. For example, if the granulated coal has a bulk density of 40 lbs./ft$^3$ and the textiles and/or plastics have a bulk density of 33 lbs./ft$^3$, the bulk density of the textiles and/or plastics would be within 21% of the ground coal. For measurement purposes, the bulk density of the textiles and/or plastics and the fossil fuel is determined on a dry basis (without addition of water) even if they are ultimately used as a slurry.

In embodiments, the maximum particle size of the textile and/or plastic aggregates is selected to be similar (below or above) to the maximum particle size of the ground solid fossil fuel. The maximum particle size of the textile and/or plastic aggregates used in the gasifier feedstock can be not more than 50% larger than the maximum solid fossil fuel size in the gasifier feedstock, or not more than 45%, or not more than 40%, or not more than 35%, or not more than 30%, or not more than 25%, or not more than 20%, or not more than 15%, or not more than 10%, or not more than 5%, or not more than 3%, or not more than 2%, or not more than 1% larger than the maximum solid fossil fuel size in the gasifier feedstock, or not larger than, or smaller than the maximum solid fossil fuel size in the gasifier feedstock. Optionally, the maximum particle size of the textile and/or plastic aggregates used in the gasifier feedstock as stated above can be within (meaning not larger than and not smaller than) the stated values. The maximum particle size is not determined as the maximum size of the particle distribution but rather by sieving through meshes. The maximum particle size is determined as the first mesh which allows at least 90 volume % of a sample of the particles to pass. For example, if less than 90 volume % of a sample passes through a 300 mesh, then a 100 mesh, a 50 mesh, a 30 mesh, a 16 mesh, but succeeds at a 14 mesh, then the maximum particle size of that sample is deemed to correspond to the first mesh size that allowed at least 90 volume % to pass through, and in this case, a 14 mesh corresponding to a maximum particle size of 1.4 mm.

The textile and/or plastic are desirably isolated as textiles and/or plastics feed for ultimate destination to be fed to a gasifier. In embodiments, at least 80 wt. %, or at least 85 wt. %, or at least 90 wt. %, or at least 95 wt. %, or at least 96 wt. %, or at least 97 wt. %, or at least 98 wt. %, or at least 99 wt. %, or at least 99.5 wt. %, or 100 wt. % of all solid feedstock other than solid fossil fuels and sand fed to the gasifier are textiles and/or plastics, based on the cumulative weight of all streams containing solids fed to the gasifier. These ranges are applicable to either the first or second feedstocks or during the first or second time periods.

In embodiments, the textiles and/or plastics can be mixed or co-fed with any other renewable natural (not synthetic) source or recycle source of material (recycle meaning post-consumer and postindustrial). For example, paper and cardboard, biowaste (e.g. food), wastewater sludge, switchgrass, and wood chips can be combined with the waste plastics and/or textiles. In embodiments, the amount renewable natural (not synthetic) source or recycle source of material, other than recycle textiles and/or plastics, can is at 1 wt. %, or at least 2 wt. %, or at least 5 wt. %, or at least 10 wt. %, or at least 15 wt. %, or at least 20 wt. %, but not more than 90 wt. %, or not more than 50 wt. %, or not more than 25 wt. %, or not more than 15 wt. %, or not more than 10 wt. %, or not more than 5 wt. %, or not more than 2 wt. % or not more than 1 wt. %, based on the weight of all solid fuel fed to the gasifier other than solid fossil fuel. Desirably, the amount renewable natural (not synthetic) source or recycle source of material, other than recycle textiles and/or plastics, is less than 1 wt. %, or less than 0.5 wt. %, or zero based on the weight of all solid fuel fed to the gasifier other than solid fossil fuel. These ranges are applicable to either the first or second feedstocks or during the first or second time periods.

The textiles and/or plastics are optionally sieved, and then combined with one or more fossil fuel components of the feedstock stream at any location prior to introducing the feedstock stream into gasification zone within the gasifier. Solid fossil fuel grinding equipment will provide an excellent source of energy for mixing textile and/or plastic aggregates with the solid fossil fuel while reducing the size of the solid fossil fuel particles. Therefore, one of the desirable locations for combining textile and/or plastic aggregates having a target size for feeding into the gasifier is into the equipment used for grinding the other solid fossil fuel sources (e.g. coal, pet-coke). This location is particularly attractive in a slurry fed gasifier because it is desirable to use a feed having the highest stable solids concentration possible, and at higher solids concentration, the viscosity of the slurry is also high. The torque and shear forces employed in fossil fuel grinding equipment is high, and coupled with the shear thinning behavior of a solid fossil fuel (e.g. coal) slurry, good mixing of the textile and/or plastic aggregates with the ground fossil fuel can be obtained in the fossil fuel grinding equipment.

Other locations for combining textile and/or plastic aggregates with fossil fuel sources can be onto the fossil fuel loaded on the main fossil fuel belt feeding a mill or grinder, or onto the main fossil fuel before the fossil fuel is loaded onto the belt to the mill or grinder, or into a fossil fuel slurry storage tank containing a slurry of fossil fuel ground to the final size, particularly if the storage tank is agitated.

Granulators can be used to obtain the desired size reduction. These can include systems for shredding the textiles and/or plastics using high capacity shredders, and if necessary, a fine/powder granulator can be used in a last step. For the last step, the fine/powder granulators can be in communication with a conveying system to transport the textile and/or plastic aggregates to a storage vessel from which the textile and/or plastic aggregates particles can be fed to any location for making the feedstock stream, or the particles can be fed continuously from the fine granulator to the desired location for making the feedstock stream. The feed of granulated textile and/or plastic aggregates particles from a storage vessel can be in a batch mode or in a continuous mode.

In embodiments, during the second time period, a fossil fuel mill or grinder is present but not used to mill or grid any fossil fuel, or is not in operation. Optionally, the textiles and/or plastics are fed downstream of a fossil fuel grinder or mill, such as to a slurry tank.

The solid fossil fuel is typically ground to a size of 2 mm or less, and can be ground to any of the sizes noted above with respect to the textile and/or plastic aggregates of less than 2 mm. The small size of the coal and textile and/or plastic aggregates particles is advantageous to enhance a uniform suspension in the liquid vehicle which will not settle out, to allow sufficient motion relative to the gaseous reactants, to assure substantially complete gasification, and to provide pumpable slurries of high solids content with a minimum of grinding.

In embodiments, both textile and plastic aggregates are fed to the gasifier. For example, a single feedstock composition can contain the textile and/or plastic aggregate particles, or they may be contained in separate streams fed to the gasifier. In embodiments, at least 80 wt. %, or at least 85 wt. %, or at least 90 wt. %, or at least 95 wt. %, or at least 96 wt. %, or at least 97 wt. %, or at least 98 wt. %, or at least 99 wt. %, or at least 99.5 wt. %, or 100 wt. % of all solid feedstock, other than solid fossil fuels, fed to the gasifier is textile and/or plastic aggregate and recycle plastic particles, based on the cumulative weight of all streams containing solids fed to the gasifier.

In embodiments, the solids fed to the gasifier include a combination of textiles and plastic particles as a solid/solid combination, and desirably also solid fossil fuel particles. The weight ratio of textile:plastic can be from 1:99 to 99:1, or 10:90 to 90:10, or 20:80 to 80:20, or from 30:70 to 70:30.

If plastic and textile aggregates are used in combination, the combination is desirably not more than any of the sizes mentioned above applicable to the textile and/or plastic aggregate.

The solids in the feedstock composition desirably do not contain sewage sludge, wastepaper not already embedded in a thermoplastic matrix, or biomass. In embodiments, the feedstock composition contains not more than 10 wt. %, or not more than 6 wt. %, or not more than 5 wt. %, or not more than 4 wt. %, or not more than 3 wt. %, or not more than 2 wt. %, or not more than 1 wt. %, or not more than 0.5 wt. %, or not more than 0.25 wt. %, or not more than 0.1 wt. % of any one of sewage sludge, waste paper not embedded in a thermoplastic matrix, biomass, or a combination of two or more, each based on the weight of the solids in the feedstock composition.

The textiles and/or plastics may contain some level of inorganic materials other than polymer, such as metals, glass (whether in the form of fibers or particles), mineral fillers, and other inorganic materials. The quantity of such materials in the textiles and/or plastics that feed into the feedstock composition, is desirably less than 8 wt. %, or not more than 6 wt. %, or not more than 5 wt. %, or not more than 4 wt. %, or not more than 3.5 wt. %, or not more than 2 wt. %, or not more than 1.5 wt. %, or not more than 1 wt. %, or not more than 0.75 wt. %, or not more than 0.5 wt. %, based on the weight of the textiles and/or plastics.

The amount of solid fossil fuel, such as coal, in the feedstock or fed to the gasifier can be at least 10 wt. %, or at least 98 wt. %, or at least 98.5 wt. %, or at least 99 wt. %, and less than 100 wt. %, or less than 99.5 wt. %, based on the weight of solids in the feedstock.

Coal contains a quantity of ash that also contains elements other than carbon, oxygen, and hydrogen. The quantity of elements other than carbon, hydrogen, oxygen, and sulfur in the fossil fuel, or in the feedstock composition, is desirably not more than 15 wt. %, or not more than 13 wt. %, or not more than 10 wt. %, or not more than 9 wt. %, or not more than 8.5 wt. %, or not more than 8 wt. %, or not more than 7.5 wt. %, or not more than 7 wt. %, or not more than 7.5 wt. %, or not more than 7 wt. %, or not more than 6.5 wt. %, or not more than 6 wt. %, or not more than 5.5 wt. %, or not more than 5 wt. %, or not more than 4.5 wt. %, based on the dry weight of the fossil fuel or alternatively based on the weight of all dry solids in the feedstock composition, or based on the weight of the feedstock composition, respectively.

The caloric heat value of textiles and/or plastics are desirably similar to or better than that of coal. For example, the textiles and/or plastics can have a heat value of at least 13,000, or at least 13,500, or at least 14,000 BTU/lb., or in the range of 13,000 to 15,000 BTU/lb. (30 MJ/Kg-35 MJ/Kg), while bituminous coal can have a heat value in a range of 12,500 to 13,300 BTU/lb. (29-31 MJ/Kg). Further, any ash or non-organic material can be melted and vitrified into the ash or slag matrix that is produced from the inorganics in the coal.

The concentration of solids (e.g. fossil fuel and textiles and/or plastics) in the feedstock composition should not exceed the stability limits of a slurry or a solids/solids mix, or the ability to pump or feed the feedstock at the target solids concentration to the gasifier. However, the concentration of plastics and/or textiles in a slurry should be as high as possible to lower the amount of water fed to the gasifier since water consumes thermal energy. Desirably, the solids content of a fossil fuel containing slurry the first feedstock stream or during the first time period, should be at least 50 wt. %, or at least 55 wt. %, or at least 60 wt. %, or at least 62 wt. %, or at least 65 wt. %, or at least 68 wt. %, or at least 69 wt. %, or at least 70 wt. %, or at least 75 wt. %, based on the weight of the slurry remainder being a liquid phase that can include water and liquid additives. The upper limit is not particularly limited because it is dependent upon the gasifier design. The solids content in the textile and/or plastics containing slurry in the second feedstock stream or during the second time period is also desirably as high as possible, such as at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 65 wt. %, based on the weight of the slurry.

The solids concentration of a dry fossil fuel fed gasifier in the first feedstock stream or during the first time period, is desirably 95 wt. % or more, or 97 wt. % or more, or 98 wt. % or more, or 99 wt. % or more, or 100 wt. %, based on the weight of the solid fuel fed to the gasifier or of all fuel fed to the gasifier (excluding the weight of the gas and moisture contained in the solids). The textile and/or plastic concentration of a dry fossil fuel fed gasifier the second feedstock stream or during the second time period, is desirably in the amounts stated above, e.g. starting at an amount of at least more than 10 wt. % and up to 100 wt. %. weight of the solid fuel fed to the gasifier or of all fuel fed to the gasifier (excluding the weight of the gas and moisture contained in the solids).

A slurry feedstock composition in either or both of the first and second feedstocks streams is desirably stable at 5 minutes, or even 10 minutes, or even 15 minutes, or even 20 minutes, or even ½ hour, or even 1 hour, or even two hours. A slurry feedstock is deemed stable if its initial viscosity is 100,000 cP or less. The initial viscosity can be obtained by the following method. A 500-600 g of a well-mixed sample is allowed to stand still in a 600 mL liter glass beaker at ambient conditions (e.g. 25° C. and about 1 atm). A Brookfield R/S Rheometer equipped with V80-40 vane operating at a shear rate of 1.83/s is submerged into the slurry to the bottom of the beaker after the slurry is well mixed (e.g. a homogeneous distribution of solids was formed). After a designated period of time, a viscosity reading is obtained at the start of rotation, which is the initial viscosity reading. The slurry is considered to be stable if the initial reading on starting a viscosity measurement is not more than 100,000 cP at the designated period of time. Alternatively, the same procedure can be used with a Brookfield viscometer with an LV-2 spindle rotating at a rate of 0.5 rpm. Since different viscosity value will be obtained using the different equipment, the type of equipment used should be reported. However, regardless of the differences, the slurry is considered stable under either method only if its viscosity is not more than 100,000 cP at the reported time.

The quantity of solids in the feedstock composition and their particle size are adjusted to maximize the solids content while maintaining a stable and pumpable slurry. A pumpable slurry is one which has a viscosity under 30,000 cP, or not more than 25,000 cP, or not more than 23,000 cP, and desirably not more than 20,000 cP, or not more than 18,000 cP, or not more than 15,000 cP, or not more than 13,000 cP, in each case at ambient conditions (e.g. 25° C. and 1 atm). At higher viscosities, the slurry becomes too thick to practically pump. The viscosity measurement to determine the pumpability of the slurry is taken by mixing a sample of the slurry until a homogeneous distribution of particles is obtained, thereafter immediately submerging a Brookfield viscometer with an LV-2 spindle rotating at a rate of 0.5 rpm into the well mixed slurry and taking a reading without delay. Alternatively, a Brookfield R/S rheometer with V80-40 vane spindle operating at a shear rate of 1.83/s can be used. The method of measurement is reported since the measured values between the two rheometers at their difference shear rates will generate different values. However, the cP values stated above apply to either of the rheometer devices and procedures.

In embodiments, the slurry feedstock composition in the first, second, or both feedstock streams has a viscosity of 80,000 cP or less, or 70,000 cP or less, or 60,000 cP or less, 50,000 cP or less, or 40,000 cP or less, or 35,000 cP or less, or 25,000 cP or less, or 20,000 cP or less, or 15,000 cP or less, or 10,000 cP or less, in each case, at 5 minutes, or even 10 minutes, or even 15 minutes, or even 20 minutes, desirably at 5 minutes or at 20 minutes, or at 20 minutes and desirably at 60,000 cP or less or 40,000 cP or less.

In embodiments, the fossil fuel is at least coal. The quality of the coal employed is not limited. Anthracite, bituminous, sub-bituminous, brown coal, and lignite coal can be sources of coal feedstock. To increase the thermal efficiency of the gasifier, the coal employed desirably has a carbon content that exceeds 35 wt. %, or at least 42 wt. %, based on the weight of the coal. Accordingly, bituminous or anthracite coal is desirable due to their higher energy content.

Sulfur is also typically present in solid fossil fuels. Desirably, the content of sulfur is less than 5 wt. %, not more than 4 wt. %, or not more than 3 wt. %, or not more than 2.5 wt. %, and also can contain a measure of sulfur, such as at least 0.25 wt. %, or at least 0.5 wt. %, or at least 0.75 wt. %, based on the weight of the solid fossil fuel.

It is also desirable to employ a solid fossil fuel with a low inherent moisture content to improve the thermal efficiency of the gasifier. Using coal having moisture contents less than 25 wt. % or less than 20 wt. % or less than 15 wt. % or not more than 10 wt. % or not more than 8 wt. % is desirable to improve the energy efficiency of the gasifier.

Desirably, the coal feedstock has a heat value of at least 11,000 BTU/lb., or at least 11,500 BTU/lb., or at least 12,500 BTU/lb., or at least 13,000 BTU/lb., or at least 13,500 BTU/lb., or at least 14,000 BTU/lb., or at least 14,250 BTU/lb., or at least 14,500 BTU/lb.

In a slurry fed gasifier, while it is possible that the feedstock composition may contain minor amounts of liquid hydrocarbon oils leached from textiles and/or plastics or coal, the feedstock composition desirably contains less than 5 wt. %, or not more than 3 wt. %, or not more than 1 wt. %, or not more than 0.1 wt. % liquid (at ambient conditions) non-oxygenated hydrocarbon petroleum oils introduced as such into the feedstock composition. Desirably, the feedstock composition contains less than 2 wt. %, or not more than 1 wt. %, or no added liquid fraction from refining crude oil or reforming any such fraction in a slurry feedstock stream or to a slurry fed gasifier.

In a slurry gasifier feedstock, the content of liquids, or the content of water, present in the first and/or second feedstock streams is desirably not more than 50 wt. %, or not more than 35 wt. %, or not more than 32 wt. %, or not more than 31 wt. %, or not more than 30 wt. %, based on the weight of the feedstock stream. Desirably, in each case, the content of liquids or water in the feedstock stream composition for a slurry fed gasifier is desirably at least 10 wt. %, or at least 15 wt. %, or at least 20 wt. %, or at least 25 wt. %, or at least 27 wt. %, or at least 30 wt. %, based on the weight of the feedstock composition. The liquids present in the slurry gasifier feedstock desirably contain at least 95 wt. % water, or at least 96 wt. % water, or at least 97 wt. % water, or at least 98 wt. % water, or at least 99 wt. % water, based on the weight of all liquids fed to the gasifier. In embodiments, other than chemical additives that are chemically synthesized and contain oxygen or sulfur or nitrogen atoms, the liquid content of the feedstock composition is at least 96 wt. % water, or at least 97 wt. % water, or at least 98 wt. % water, or at least 99 wt. % water, based on the weight of all liquids fed to the gasifier.

In embodiments, at least a portion of the fuel feedstock to the gasifier is a liquid at 25° C. and 1 atmosphere, such as organic feedstocks, petroleum oils or fractions from refining or distilling crude oil, hydrocarbons, oxygenated hydrocarbons, or synthetic chemical compounds. These liquid feedstocks can be from any fraction from petroleum distillation or refining, or any chemical synthesized at a chemical manufacturing facility, provided they are liquid. These liquids are a carbon fuel source for gasifying into syngas. In embodiments, there is now also provided a combination of textiles and/or plastics and a hydrocarbon liquid fuel or oxygenated hydrocarbon liquid fuel that are liquid at 25° C. and 1 atmosphere. Depending on the nature of the liquid fuel feedstock, the textile and/or plastic aggregate may be insoluble, partially soluble, or soluble in the liquid fuel feedstock.

In an embodiment, the water present in the feedstock stream is not wastewater, or in other words, the water fed to the solids to make the feedstock stream is not wastewater. Desirably, the water employed has not been industrially discharged from any process for synthesizing chemicals, or it not municipal wastewater. The water is desirably fresh water, or potable water.

In embodiments, the feedstock stream comprises at least ground coal and textile and/or plastic aggregates. Desirably, the feedstock stream also comprises water. The amount of water in the feedstock stream can range from 0 wt. % up to 50 wt. %, or from 10 wt. % to 40 wt. %, or from 20 wt. % to 35 wt. %. The feedstock stream is desirably a slurry containing water.

In addition to solid fossil fuel and textiles and/or plastics, other additives can be added to and contained in the feedstock composition, such as viscosity modifiers and pH modifiers. The total quantity of additives can range from 0.01 wt. % to 5 wt. %, or from 0.05 wt. % to 5 wt. %, or from 0.05 to 3 wt. %, or from 0.5 to 2.5 wt. %, based on the weight of the feedstock composition. The quantity of any individual additive can also be within these stated ranges.

The viscosity modifiers (which includes surfactants) can improve the solids concentration in a slurry gasifier feedstock. Examples of viscosity modifiers include:
  (i) alkyl-substituted amine-based surfactant such as alkyl-substituted aminobutyric acid, alkyl-substituted polyethoxylated amide, and alkyl-substituted polyethoxylated quaternary ammonium salt; and
  (ii) sulfates such as salts of organic sulfonic acids including ammonium, calcium and sodium sulfonates, particularly those with lignin and sulfo-alkylated lignites;
  (iii) phosphate salts;
  (iv) polyoxyalkylene anionic or nonionic surfactants.

More specific examples of alkyl-substituted aminobutyric acid surfactants include N-coco-beta-aminobutyric acid, N-tallow-beta-aminobutyric acid, N-lauryl-beta-aminobutyric acid, and N-oleyl-beta-aminobutyric acid. N-coco-beta-aminobutyric acid.

More specific examples of alkyl-substituted polyethoxylated amide surfactant include polyoxyethylene oleamide, polyoxyethylene tallowamide, polyoxyethylene laurylamide, and polyoxyethylene cocoamide, with 5-50 polyoxyethylene moieties being present.

More specific examples of the alkyl-substituted polyethoxylated quaternary ammonium salt surfactant include methylbis (2-hydroxyethyl) cocoammonium chloride, methylpolyoxyethylene cocoammonium chloride, methylbis (2-hydroxyethyl) oleylammonium chloride, methylpolyoxyethylene oleylammonium chloride, methylbis (2-hydroxyethyl) octadecylammonium chloride, and methylpolyoxyethylene octadecylammonium chloride.

More specific examples of sulfonates include sulfonated formaldehyde condensates, naphthalene sulfonate formaldehyde condensates, benzene sulfonate—phenol—formaldehyde condensates, and lingosulfonates.

More specific examples of phosphate salts include trisodium phosphate, potassium phosphate, ammonium phosphate, sodium tripolyphosphate or potassium tripolyphosphate.

Examples of polyoxyalkylene anionic or nonionic surfactants have 1 or more repeating units derived from ethylene oxide or propylene oxide, or 1-200 oxyalkylene units.

Desirably, the surfactant is an anionic surfactant, such as salts of an organic sulfonic acid. Examples are calcium, sodium and ammonium salts of organic sulfonic acids such as 2,6-dihydroxy naphthalene sulfonic acid, lignite sulfonic acid, and ammonium lignosulfonate.

Examples of pH modifiers include aqueous alkali metal and alkaline earth hydroxides such as sodium hydroxide, and ammonium compounds such as 20-50 wt. % aqueous ammonium hydroxide solutions. The aqueous ammonium hydroxide solution can be added directly to the feedstock composition prior to entry into the gasifier, such as in the coal grinding equipment or any downstream vessels containing the slurry.

In embodiments, the atomic ratio of total oxygen (including reacted oxygen in the plastics and/or textiles) to carbon entering the gasification zone fed with any of the first of second streams, can be a value in the range of 0.70 to less than 2, or from 0.9 to 1.9, or from 0.9 to 1.8, or from 0.9 to 1.5, or from 0.9 to 1.4, or from 0.9 to 1.2, or from 1 to 1.9, or from 1 to 1.8, or from 1 to 1.5, or from 1 to 1.2, or from 1.05 to 1.9, or from 1.05 to 1.8, or from 1.05 to 1.5, or from 1.05 to 1.2. The atomic ratio of free oxygen to carbon entering the gasification zone can also be within these same values. As noted above, the ratio of 0:0 during a feed of one or more second feedstocks or during at least a portion of the second time period is higher than during a first time period. The weight ratio of both total oxygen and free oxygen to carbon in pounds entering the gasification zone can also each be within these stated values.

In embodiments, the total carbon content in the feedstock composition is at least 40 wt. %, or at least 45 wt. %, or at least 50 wt. %, or at least 55 wt. %, or at least 60 wt. %, or at least 65 wt. %, and desirably at least 70 wt. %, or at least 75 wt. %, or at least 80 wt. %, or at least 85 wt. %, or at least 90 wt. %, each based on the total solids content.

In embodiments, any of the gasifier feedstock compositions are desirably injected along with an oxidizer into a refractory-lined combustion chamber (gasification zone) of the synthesis gas generating gasifier. The feedstock stream (desirably a slurry) and oxidizer are desirably sprayed through an injector into a gasification zone. The gasification zone can be under significant pressure, typically about 500 psig or more, or 600 psig or more, or 800 psig or more, or 1000 psig or more. For an entrained flow gasifier, the velocity or flow rate of the feedstock and oxidizer streams ejected from the injector nozzle into the gasification zone (or combustion chamber) will exceed the rate of flame propagation to avoid backflash.

In embodiments, advantageously only one feedstock composition is charged to the gasifier or gasification zone, or in other words, all sources of carbon fuel are fed to the gasifier in only one stream.

In embodiments, only one feedstock stream is necessary or employed to produce a syngas or product stream that is a raw material to synthesize a chemical compound.

The second syngas stream is a recycle derived syngas stream. The first syngas stream may by a recycle derived syngas stream if the first feedstock also contains a recycle textile and/or plastic, or may not be a recycle derived syngas stream if the first feedstock does not contain a recycle waste.

In another embodiment, a chemical is made from a first syngas sourced from a first gasifier fed with a first feedstock composition containing a solid fossil fuel is not combined with a second syngas stream sourced from any other gasifier fed with second fossil fuel feedstock composition where the solid fossil fuel content between the first and second feedstock compositions differ by more than 20%, or more than 10%, or more than 5%, based on the weight of the all solids fed to the gasifiers. For example, a first syngas stream generated from a first feedstock composition containing 90 wt. % coal would not be combined with a syngas stream generated from a different gasifier fed with a feedstock composition containing 70 wt. % coal or no coal, but could be combined with one containing 72 wt. % coal or more.

In embodiments, a first syngas sourced from a first gasifier fed with a first feedstock composition containing a first fixed carbon content is not combined with a second syngas stream sourced from any other gasifier fed with a second feedstock containing a second fixed carbon content, where the difference between the first and second fixed carbon contents is more than 20%, or more than 10%, or more than 5% of each other, based on the weight of the all solids fed to the gasifiers. For example, a first syngas stream generated from a first feedstock composition containing 70 wt. % fixed carbon based on the weight of the solids would not be combined with a syngas stream generated from a different gasifier fed with a feedstock composition containing 30 wt. % fixed carbon, but could be combined with one containing 56 wt. % fixed carbon if the limit of 20% is selected.

Prior to entry into the gasifier, the feedstock composition may be subjected to a variety of other optional processes. For example, a slurry can flow through a thickener in which excess water is eliminated from the slurry to obtain the final desired solids concentration of the slurry entering into the gasifier vessel. The feedstock composition may be preheated to prior to entry into the gasifier. In this embodiment, a slurry feedstock composition is heated to a temperature below the boiling point of water at the operating pressure existing in reaction zone. The preheater, when employed, reduces the heat load on the gasifier and improves the efficiency of utilization of both fuel and oxygen.

In embodiments, at least 80 wt. % of all of the water required for the generation of synthesis gas in reaction zone is supplied in liquid phase. When petroleum coke is employed as fuel for the gas generator, part of the water, e.g., from 1 to about 90 percent by weight based on the weight of water, may be vaporized in the slurry feed preheater or combined with the oxidizing stream as vaporized water.

The oxidizer is desirably an oxidizing gas that can include air, and desirably is a gas enriched in oxygen at quantities greater than that found in air. The reaction of oxygen and solid fossil fuel is exothermic. Desirably, the oxidant gas contains at least 25 mole % oxygen, or at least 35 mole %, or at least 40 mole %, or at least 50 mol %, or at least 70 mole %, or at least 85 mole %, or at least 90 mole %, or at least 95 mole %, or at least 97 mole %, or at least 98 mole % oxygen, or at least 99 mole %, or at least 99.5 mole % based on all moles in the oxidant gas stream injected into the reaction (combustion) zone of the gasifier. In embodiments, the combined concentration of oxygen in all gases supplied to the gasification zone is also in the above stated amount. The particular amount of oxygen as supplied to the reaction zone is desirably sufficient to obtain near or maximum yields of carbon monoxide and hydrogen obtained from the gasification reaction relative to the components in the feedstock composition, considering the amount relative to the feedstock composition, and the amount of feedstock charged, the process conditions, and the gasifier design.

In embodiments, steam is not supplied to the gasification zone in a slurry fed gasifier. The amount of water in a slurry fed system is typically more than sufficient a co-reactant and heat sink to regulate the gasification temperature. The addition of steam in a slurry fed gasifier will generally unduly withdraw heat from the reaction zone and reduce its efficiency. In embodiments, steam is fed to the gasification zone in any type of dry fed gasifier, such as an entrainment flow gasifier, a fluidized bed gasifier, or a fixed or moving bed gasifier. The addition of steam in dry fed gasifiers case is desirable to provide the raw material needed for the production of carbon monoxide.

Other reducible oxygen-containing gases may be supplied to the reaction zone, for example, carbon dioxide, or simply air. In embodiments, no gas stream enriched in carbon dioxide or nitrogen (e.g. greater than the molar quantity found in air, or greater than 2 mole %, or greater than 5 mole %, or greater than 10 mole %, or greater than 40 mole %) is charged into a slurry fed gasifier. Many of these gases serve as carrier gases to propel a dry feed to a gasification zone. Therefore, in embodiments, one or more of these gases are charged to the gasification zone as a carrier gas for the dry feed of solid fossil fuel and textiles and/or plastics. Due to the pressure within the gasification zone, these carrier gases are compressed to provide the motive force for introduction into the gasification zone. The expenditure of energy and equipment for compressing carrier gases to the feedstock composition is avoided is a slurry feed. Accordingly, in yet another embodiment, the feedstock composition containing at least textiles and/or plastics and solid fossil fuel flowing to the gasifier, or this feedstock composition as introduced to an injector or charge pipe, or this feedstock composition as introduced into the gasification zone, or a combination of all the above, does not contain gases compressed in equipment for gas compression. Alternatively, or in addition, other than the oxygen rich stream described above, no gas compressed in equipment for gas compression is fed to the gasification zone or even to the gasifier. It is noteworthy that high pressure charge pumps that process the slurry feed for introduction into the gasification zone are not considered gas compressing equipment.

In embodiments, no gas stream containing more than 0.03 mole %, or more than 0.02 mole %, or more than 0.01 mole % carbon dioxide is charged to the gasifier or gasification zone. In another embodiment, no gas stream containing more than 77 mole %, or more than 70 mole %, or more than 50 mole %, or more than 30 mole %, or more than 10 mole %, or more than 5 mole %, or more than 3 mole % nitrogen is charged to the gasifier or gasification zone. In another embodiment, a gas stream containing more than 77 mole %, or more than 80 mole % nitrogen is charged to the gasifier or gasification zone. In another embodiment, steam is charged into the gasification zone or to the gasifier. In yet another embodiment, a gaseous hydrogen stream (e.g. one containing more than 0.1 mole % hydrogen, or more than 0.5 mole %, or more than 1 mole %, or more than 5 mole %) is not charged to the gasifier or to the gasification zone. In another embodiment, a stream of methane gas (e.g. one containing more than 0.1 mole % methane, or more than 0.5 mole %, or more than 1 mole %, or more than 5 mole % methane) is not charged to the gasifier or to the gasification zone. In another embodiment, the only gaseous stream introduced to the gasification zone is an oxygen rich gas stream as described above.

The gasification process desirably employed is a partial oxidation gasification reaction. To enhance the production of hydrogen and carbon monoxide, the oxidation process involves partial, rather than complete, oxidization of the fossil fuel and textiles and/or plastics and therefore is desirably operated in an oxygen-lean environment, relative to the amount needed to completely oxidize 100% of the carbon and hydrogen bonds. This is in contrast to a combustion reaction which would employ a large stoichiometric excess of oxygen over that needed to make carbon monoxide, leading to the production primarily of carbon dioxide and water. In the particle oxidation gasification process, the total oxygen requirements for the gasifier is desirably at least 5%, or at least 10%, or at least 15%, or at least 20%, in excess of the amount theoretically required to convert the carbon content of the solid fuel and textiles and/or plastics to carbon monoxide. In general, satisfactory operation may be obtained with a total oxygen supply of 10 to 80 percent in excess of the theoretical requirements for carbon monoxide production, but less than that required to make carbon dioxide. An example of a suitable amount of oxygen per pound of carbon is in the range of 0.4 to about 3.0-pound free oxygen per pound of carbon, or from 0.6 to 2.5, or from 0.9 to 2.5, or from 1 to 2.5, or from 1.1 to 2.5, or from 1.2 to 2.5 pounds of free oxygen per pound of carbon.

Mixing of the feedstock composition and the oxidant is desirably accomplished entirely within the reaction zone by introducing the separate streams of feedstock and oxidant so that they impinge upon each other within the reaction zone. Desirably, the oxidant stream is introduced into the reaction zone of the gasifier at high velocity both exceed the rate of flame propagation and to improve mixing with the feedstock composition. The oxidant is desirably injected into the gasification zone in the range of 25 to 500 feet per second, or 50 to 400 ft/s, or 100 to 400 ft/s. These values would be the velocity of the gaseous oxidizing stream at the injector-gasification zone interface, or the injector tip velocity.

One method for increasing the velocity of the oxidant feed to the gasification zone is by reducing the diameter of the oxidant annulus near the tip of the injector or injector. Near the tip of the injector the annular passage converges inwardly in the shape of a hollow cone. The oxidizing gas is thereby accelerated and discharged from the injector as a high velocity conical stream having an apex angle in the desirably range of about 30° to 45°. The streams from the injector converge at a point located about 0-6 inches beyond the injector face. The high velocity stream of oxidizing gas hits the relatively low velocity feedstock stream, atomizing it and forming a fine mist comprising minute particles of water and particulate solid fossil fuel highly dispersed in the oxidizing gas. The particles of solid carboniferous matter impinge against one another and are fragmented further.

The velocity of the fuel feedstock is determined by the desired throughput of syngas generation. Suitable examples of feedstock velocity introduced into gasification zone prior to contact with the oxidizing agent is in the range of 5 to 50 feet per second.

The feedstock composition and the oxidant can optionally be preheated to a temperature above about 200° C., or at least 300° C., or at least 400° C. Advantageously the gasification process does not require preheating the feedstock composition to efficiently gasify the fuel, and a preheat treatment step would result in lowering the energy efficiency of the process. Desirably, the feedstock composition, and optionally the oxidant, are not preheated prior to their introduction into the gasifier. A preheat treatment step would be contacting the feedstock composition or oxidant with equipment that raises the temperature of the feedstock composition sufficiently such that the temperature of the feedstock composition or oxidant stream is above 200° C., or above 190° C., or above 170° C., or above 150° C., or above 130° C., or above 110° C., or above 100° C., or above 98° C., or above 90° C., or above 80° C., or above 70° C., or above 60° C., immediately prior to introduction into an injector on the gasifier. For example, while coal can be dried with hot air above 200° C., this step would not be considered a preheat of the feedstock composition if the feedstock composition is below 200° C. upon its introduction into the injector.

In another embodiment, no thermal energy (other than incidental heat from processing equipment such as mills, grinders or pumps) is applied to the feedstock composition containing both textile and/or plastic aggregates and the solid fossil fuel, or to the oxidant stream, at any point prior to its introduction into the injector, or gasifier, or gasification zone (other than the temperature increase experienced in an injector) that would increase the temperature of the stream by more than 180° C., or more than 170° C., or more than 160° C., or more than 150° C., or more than 140° C., or more than 130° C., or more than 120° C., or more than 110° C., or more than 100° C., or more than 90° C., or more than 80° C., or more than 70° C., or more than 60° C., or more than 50° C., or more than 40° C., or more than 30° C.

The process employs a gasification process, which is distinct from a incineration process that generates primarily carbon dioxide and water, or a pyrolysis process which is a thermal process that degrades a fuel source in the absence of air or oxygen and generates primarily a liquid, or plasma processes in that gasification does not employ a plasma arc.

In one embodiment, the type of gasification technology employed is a partial oxidation entrained flow gasifier that generates syngas. This technology is distinct from fixed bed (alternatively called moving bed) gasifiers and from fluidized bed gasifiers. In fixed bed (or moving bed gasifiers), the feedstock stream moves in a countercurrent flow with the oxidant gas, and the oxidant gas typically employed is air. The feedstock stream falls into the gasification chamber, accumulates, and forms a bed of feedstock. Air (or alternatively oxygen) flows from the bottom of the gasifier up through the bed of feedstock material continuously while fresh feedstock continuously falls down from the top by gravity to refresh the bed as it is being combusted. The combustion temperatures are typically below the fusion temperature of the ash and are non-slagging. Whether the fixed bed operated in countercurrent flow or in some instances in co-current flow, the fixed bed reaction process generates high amount of tars, oils, and methane produced by pyrolysis of the feedstock in the bed, thereby both contaminating the syngas produced and the gasifier. The contaminated syngas requires significant effort and cost to remove tarry residues that would condense once the syngas is cooled, and because of this, such syngas streams are generally not used to make chemicals and are instead used in direct heating applications, or as liquid fuels. Downdraft fixed or moving bed gasifiers produce less or no tar. Fixed or moving bed gasifiers already equipped or built to be equipped with tar removal processes are suitable to accept a feed of the textile and/or plastic aggregate.

In a fluidized bed, the feedstock material in the gasification zone is fluidized by action of the oxidant flowing through the bed at a high enough velocity to fluidize the particles in the bed. In a fluidized bed, the homogeneous reaction temperatures and low reaction temperatures in the gasification zone also promotes the production of high amounts of unreacted feedstock material and low carbon conversion, and operating temperatures in the fluidized bed are typically between 800-1000° C. Further, in a fluidized bed, it is important to operate below slagging conditions to maintain the fluidization of the feedstock particles which would otherwise stick to the slag and agglomerate. By employing an entrained flow gasification, these deficiencies present with fixed (or moving bed) and fluidized bed gasifiers that are typically used to process waste materials is overcome.

In embodiments, the feedstock stream is introduced at the top ⅛ section of the gasifier, desirably at the top 1/12 of the gasifier height defined by the gasifier shell (not including the injector height protruding from the top of the shell or pipes protruding from the bottom of the shell). The feedstock composition is desirably not introduced into a side wall of the gasifier. In embodiments, the feedstock composition is not a tangential feed injector.

In embodiments, oxidant is introduced at the top ⅛ section of the gasifier, desirably at the top 1/12 of the gasifier height defined by the gasifier shell. The oxidant is desirably not introduced into the side wall of the gasifier or bottom of the flow gasifier. In another embodiment, both the feedstock composition and oxidant are introduced at the top ⅛ section of the gasifier, desirably at the top 1/12 of the gasifier height defined by the gasifier shell. Desirably, the oxidant and feedstock composition are fed co-currently to ensure good mixing. In this regard, a co-current feed means that the axis of the feedstock and oxidant streams are substantially parallel (e.g. not more than a 25° deviation, or not more than a 20°, or not more than a 15°, or not more than a 10°, or not more than a 8°, or not more than a 6°, or not more than a 4°, or not more than a 2°, or not more than a 1° deviation from each other) and in the same direction.

The feedstock and oxidant streams are desirably introduced into the gasification zone through one or more injector nozzles. Desirably, the gasifier is equipped with at least one of the injector nozzles in which through that injector nozzle both a feedstock stream and an oxidant stream are introduced into the gasification zone.

While the feedstock stream can be a dry feed or a slurry feed, the feedstock stream is desirably a slurry.

The syngas produced in the gasification process is desirably used at least in part for making chemicals. Many synthetic processes for making chemicals are at high pressure, and to avoid energy input into pressurizing the syngas stream, desirably the gasifier is also run at high pressure, particularly when the syngas stream is directly or indirectly in gaseous communication with a vessel in which a chemical is synthesized. Dry feeds to a gasifier operating at high pressure are specially treated to ensure that the feed can be effectively blown and injected into the high-pressure gasification zone. Some techniques include entraining a flow of nitrogen at high pressure and velocity, which tends to dilute the syngas stream and reduce the concentration of desirably components such as carbon monoxide and hydrogen. Other carrier or motive gases include carbon monoxide, but like nitrogen, these gases are compressed before feeding into or compressed with the solid fossil fuels, adding to the energy requirements and capital cost of feed lock hoppers and/or compressing equipment. To deal with these issues, many dry feed gasifiers will operate at lower pressures, which for the mere production of electricity is sufficient, but is undesirable for gasifiers producing a syngas stream for making chemicals. With a slurry feed, a motive gas is not necessary and can readily be fed to a high-pressure gasifier that produces syngas as high pressure, which is desirable for making chemicals. In embodiments, the feedstock stream is not processed through a lock hopper prior to entering an injector or entering the gasification zone. In another embodiment, the feedstock composition containing size reduced textiles and/or plastics and solid fossil fuel is not pressurized in a lock hopper prior to feeding to the injector or gasification zone.

Desirably, the gasifier is non-catalytic, meaning that gasifier does not contain a catalyst bed, and desirably the gasification process is non-catalytic, meaning that a catalyst is not introduced into the gasification zone as a discrete unbound catalyst (as opposed to captive metals in the textiles and/or plastics or solid fossil fuel that can incidentally have catalytic activity). The gasification process in the reaction zone is desirably conducted in the absence of added catalysts and contains no catalyst bed. The gasification process is also desirably a slagging gasification process; that is, operated under slagging conditions (well above the fusion temperature of ash) such that a molten slag is formed in the gasification zone and runs along and down the refractory walls.

In embodiments, the gasifier is not designed to contain a pyrolysis zone. Desirably, the gasifier is not designed to contain a combustion zone. Most preferably, the gasifier is designed to not contain, or does not contain, either a combustion zone or a pyrolysis zone. The pyrolysis zone incompletely consumes the fuel source leading to potentially high amounts of ash, char, and tarry products. A combustion zone, while absent in tars, produces high amounts of $CO_2$ and lower amounts of the more desirably carbon monoxide and hydrogen. Desirably, the gasifier is a single stage reactor, meaning that there is only one zone for conversion of the carbon in the feedstock to syngas within the gasifier shell.

The gasification zone is void or empty space defined by walls in which oxidation reactions occur and allow gases to form within the space. Desirably, gasification zone does not have a bath of molten material or molten material that accumulates at the bottom of the gasification zone to form a bath. The gasification zone is desirably not enclosed on the bottom but rather is in gaseous communication with other zones below the gasification zone. Slag, while molten, does not accumulate at the bottom of the gasification zone but rather runs down the sides of the refractory and into a zone below the gasification zone, such as a quench zone to solidify the slag.

The flow of hot raw syngas in the gasifier is desirably vertically downward, or a down-flow gasifier. Desirably, the flow of syngas generated in the gasifier is downward from the highest point of injecting the feedstock composition, desirably from the point of all feedstock stream locations. In another embodiment, the location for withdrawing the syngas stream from the gasifier is lower that at least one location for introducing the feedstock stream, desirably lower than all locations for introducing a feedstock stream.

The gasifier can contain refractory lining in the gasification zone. While a steam generating membrane or jacket between the gasifier wall and the surfaces facing the gasification zone can be employed, desirably the gasifier does not contain a membrane wall, or a steam generating membrane, or a steam jacket in the gasification zone or between inner surfaces facing the gasification zone and the gasifier shell walls as this removes heat from the gasification zone. Desirably, the gasification zone is lined with refractory, and optionally there is no air or steam or water jacket between the refractory lining the gasification zone (or optionally in any reaction zone such as combustion or pyrolysis) and the outer shell of the gasifier.

The gasification process is desirably a continuous process meaning that the gasifier operates in a continuous mode. By a continuous mode for gasifier operation is meant that the gasification process is continuous for at least 1 month, or at least 6 months, or at least 1 year. Desirably, the inclusion of textile and/or plastic aggregates in the feedstock composition is continuous for at least 1 day, or at least 3 days, or at least 14 days, or at least 1 month, or at least 6 months, or at least 1 year. A process is deemed continuous despite shutdowns due to maintenance or repair.

The campaign from the one or more first feedstocks to the one or more second feedstocks, or from the first to the second time period, is one cycle. In embodiments, the at least one cycle or at least two cycles or at least three cycles are conducted within one year. In embodiments, the campaign includes 1.5 cycles:
a. from a first time period to a second time period to a third time period, where at least the gasification temperature differences between the first and third time period are closer than between the first and second time periods, or
b. from a first feedstock to a second feedstock to a third feedstock, where the solid fossil fuel content differences between the first and third feedstock are smaller than the first and second feedstock.

In embodiments, the gasification zone, and optionally all reaction zones in the gasifier are operated at a temperature in the range of at least 1000° C., or at least 1100° C., or at least 1200° C., or at least 1250° C., or at least 1300° C., and up to about 2500° C., or up to 2000° C., or up to 1800° C., or up to 1600° C., each of which are well above the fusion temperature of ash, and are desirably operated to form a molten flow of slag in the reaction zone. In embodiments, the reaction temperature is desirably autogenous. Advantageously, the gasifier operating in steady state mode is at an autogenous temperature and does not require application of external energy sources to heat the gasification zone. In a fixed bed, moving bed, or fluidized bed gasifier, the gasification zone is generally below 1000° C., or not above 950° C., or not higher than 800° C.

In embodiments, the gasifier does not contain a zone within the gasifier shell to dry feedstock such as the coal, pet-coke, or textiles and/or plastics prior to gasification. The increase in temperature within the injector is not considered a zone for drying.

Desirably, the gasification zone is not under negative pressure during operations, but rather is under positive pressure during operation. The gasification zone is desirably not equipped with any aspirator or other device to create a negative pressure under steady state operation.

The gasifier can be operated at a pressure within the gasification zone (or combustion chamber) of at least 200 psig (1.38 MPa), or at least 300 psig (2.06 MPa), or at least 350 psig (2.41 MPa), and desirably at least 400 psig (2.76 MPa), or at least 420 psig (2.89 MPa), or at least 450 psig (3.10 MPa), or at least 475 psig (3.27 MPa), or at least 500 psig (3.44 MPa), or at least 550 psig (3.79 MPa), or at least 600 psig (4.13 MPa), or at least 650 psig (4.48 MPa), or at least 700 psig (4.82 MPa), or at least 750 psig (5.17 MPa), or at least 800 psig (5.51 MPa), or at least 900 psig (6.2 MPa), or at least 1000 psig (6.89 MPa), or at least 1100 psig (7.58 MPa), or at least 1200 psig (8.2 MPa). The particular operating pressure on the high end is regulated with a variety of considerations, including operating efficiency, the operating pressures needed in chemical synthesis gasifiers particularly with integrated plants, and process chemistry. Suitable operating pressures in the gasification zone on the high end need not exceed 1300 psig (8.96 MPa), or need not exceed 1250 psig (8.61 MPa), or need not exceed 1200 psig (8.27 MPa), or need not exceed 1150 psig (7.92 MPa), or need not exceed 1100 psig (7.58 MPa), or need not exceed 1050 psig (7.23 MPa), or need not exceed 1000 psig (6.89 MPa), or need not exceed 900 psig (6.2 MPa), or need not exceed 800 psig (5.51 MPa), or need not exceed 750 psig (5.17 MPa). Examples of suitable desirably ranges include 400 to 1000, or 425 to 900, or 450 to 900, or 475 to 900, or 500 to 900, or 550 to 900, or 600 to 900, or 650 to 900, or 400 to 800, or 425 to 800, or 450 to 800, or 475 to 800, or 500 to 800, or 550 to 800, or 600 to 800, or 650 to 800, or 400 to 750, or 425 to 750, or 450 to 750, or 475 to 750, or 500 to 750, or 550 to 750, each in psig.

Desirably, the average residence time of gases in the gasifier reactor are very short to increase throughput. Since the gasifier is operated at high temperature and pressure, substantially complete conversion of the feedstock to gases can occur in a very short time frame. The average residence time of the gases in the gasifier can be as short as less than 30 seconds, or not more than 25 seconds, or not more than 20 seconds, or not more than 15 seconds, or not more than 10 seconds, or not more than 7 seconds. Desirably, the average residence time of gases in all zones designed for conversion of feedstock material to gases is also quite short, e.g. less than 25 seconds, or not more than 15 seconds, or not more than 10 seconds, or not more than 7 seconds, or not more than 4 seconds. In these time frames, at least 85 wt. %, or at least or more than 90 wt. %, or at least 92 wt. %, or at least 94 wt. % of the solids in the feedstock can be converted to gases (substances which remain as a gas if the gas stream were cooled to 25° C. and 1 atm) and liquid (substances which are in liquid state if the gas stream is cooled to 25° C. and 1 atm such as water), or more than 93 wt. %, or more than 95 wt. %, or more than 96 wt. %, or more than 97 wt. %, or more than 98 wt. %, or more than 99 wt. %, or more than 99.5 wt. %.

A portion of ash and/or char in the gasifier can be entrained in the hot raw syngas stream leaving the gasification reaction zone. Ash particles in the raw syngas stream within the gasifier are particles which have not reached the melting temperature of the mineral matter in the solid fuel. Slag is substantially molten ash or molten ash which has solidified into glassy particles and remains within the gasifier. Slag is molten until quenched and then form beads of fused mineral matter. Char are porous particles that are devolatilized and partially combusted (incompletely converted) fuel particles. The particulate matter gathered in the bottom part of the gasifier, or the quench zone, are predominately slag (e.g. above 80 wt. % slag) and the remainder is char and ash. Desirably, only trace amounts of tar or no tar is present in the gasifier, or in the quench zone, or in the gasification zone, or present in the hot raw syngas within the gasifier, or present in the raw syngas discharged from the gasifier (which can be determined by the amount of tar condensing from the syngas stream when cooled to a temperature below 50° C.). Trace amounts are less than 0.1 wt. % (or less than 0.05 wt. % or less than 0.01 wt. %) of solids present in the gasifier, or less than 0.05 volume %, or not more than 0.01 vol %, or not more than 0.005 vol %, or not more than 0.001 volume %, or not more than 0.0005 vol %, or not more than 0.0001 vol % in the raw syngas stream discharged from the gasifier.

In another embodiment, the process does not increase the amount of tar to a substantial extent relative to the same process except replacing the textiles and/or plastics with the same amount and type of solid fossil fuel used in the feedstock composition containing the textiles and/or plastics.

The quantity of tar generated in the process with the feedstock containing the textiles and/or plastics is less than 10% higher, or less than 5% higher, or less than 3% higher, or less than 2% higher, or not higher at all, than the amount of tar generated with the same feedstock replacing the textiles and/or plastics with the same solid fossil fuel under the same conditions.

To avoid fouling downstream equipment from the gasifier (scrubbers, CO/H2 shift reactors, acid gas removal, chemical synthesis), and the piping in-between, the first and second syngas streams should have low or no tar content. The first and second syngas stream as discharged from the gasifier desirably contains no or less than 4 wt. %, or less than 3 wt. %, or not more than 2 wt. %, or not more than 1 wt. %, or not more than 0.5 wt. %, or not more than 0.2 wt. %, or not more than 0.1 wt. %, or not more than 0.08 wt. %, or not more than 0.05 wt. %, or not more than 0.02 wt. %, or not more than 0.01 wt. %, or nor more than 0.005 wt. % tar, based on the weight of all condensable solids in the syngas stream. For purposes of measurement, condensable solids are those compounds and elements that condense at a temperature of 15° C./1 atm.

In embodiments, the tar present, if at all, in each of the first and second syngas stream discharged from the gasifier is less than 10 g/m3 of the syngas discharged, or not more than 9 g/m3, or not more than 8 g/m3, or not more than 7 g/m3, or not more than 6 g/m3, or not more than 5 g/m3, or not more than 4 g/m3, or not more than 3 g/m3, or not more than 2 g/m3, and desirably not more than 1 g/m3, or not more than 0.8 g/m3, or not more than 0.75 g/m3, or not more than 0.7 g/m3, or not more than 0.6 g/m3, or not more than 0.55 g/m3, or not more than 0.45 g/m3, or not more than 0.4 g/m3, or not more than 0.3 g/m3, or not more than 0.2 g/m3, or not more than 0.1 g/m3, or not more than 0.05 g/m3, or not more than 0.01 g/m3, or not more than 0.005 g/m3, or not more than 0.001 g/m3, or not more than 0.0005 g/m3, in each case Normal (15° C./1 atm). For purposes of measurement, the tars are those tars that would condense at a temperature of 15° C./1 atm, and includes primary, secondary and tertiary tars, and are aromatic organic compounds and other than ash, char, soot, or dust. Examples of tar products include naphthalenes, cresols, xylenols, anthracenes, phenanthrenes, phenols, benzene, toluene, pyridine, catechols, biphenyls, benzofurans, benzaldehydes, acenaphthylenes, fluorenes, naphthofurans, benzanthracenes, pyrenes, acephenanthrylenes, benzopyrenes, and other high molecular weight aromatic polynuclear compounds. The tar content can be determined by GC-MSD.

In embodiments, the tar yield of the gasifier from each of the first and second syngas streams (combination of tar in syngas and tar in reactor bottoms and in or on the ash, char, and slag) is not more than 4 wt. %, or not more than 3 wt. %, or not more than 2.5 wt. %, or not more than 2.0 wt. %, or not more than 1.8 wt. %, or not more than 1.5 wt. %, or not more than 1.25 wt. %, or not more than 1 wt. %, or not more than 0.9 wt. %, or not more than 0.8 wt. %, or not more than 0.7 wt. %, or not more than 0.5 wt. %, or not more than 0.3 wt. %, or not more than 0.2 wt. %, or not more than 0.1 wt. %, or not more than 0.05 wt. %, or not more than 0.01 wt. %, or not more than 0.005 wt. %, or not more than 0.001 wt. %, or not more than 0.0005 wt. %, or not more than 0.0001 wt. %, based on the weight of solids in the feedstock composition fed to the gasification zone.

The amount of char (or incompletely converted carbon in the feedstock) generated by conversion of the carbon sources in the feedstock composition is not more than 15 wt. %, or not more than 12 wt. %, or not more than 10 wt. %, or not more than 8 wt. %, or not more than 5 wt. %, or not more than 4.5 wt. %, or not more than 4 wt. %, or not more than 3.5 wt. %, or not more than 3 wt. %, or not more than 2.8 wt. %, or not more than 2.5 wt. %, or not more than 2.3 wt. %, or not more than 4.5 wt. %, or not more than 4.5 wt. %, or not more than 4.5 wt. %.

In the process, char can be recycled back to the feedstock composition to the gasifier containing the textiles and/or plastics. In embodiments, the efficiencies and features can be obtained without recycling char back to the gasification zone.

The total amount of char (or incompletely converted carbon in the feedstock) and slag (if any) generated in the gasifier or by the process is desirably not more than 20 wt. %, or not more than 17 wt. %, or not more than 15 wt. %, or not more than 13 wt. %, or not more than 10 wt. %, or not more than 9 wt. %, or not more than 8.9 wt. %, or not more than 8.5 wt. %, or not more than 8.3 wt. %, or not more than 8 wt. %, or not more than 7.9 wt. %, or not more than 7.5 wt. %, or not more than 7.3 wt. %, or not more than 7 wt. %, or not more than 6.9 wt. %, or not more than 6.5 wt. %, or not more than 6.3 wt. %, or not more than 6 wt. %, or not more than 5.9 wt. %, or not more than 5.5 wt. %, in each case based on the weight of the solids in the feedstock composition. In embodiments, the same values apply with respect to the total amount of ash, slag, and char generated in the gasifier or by the process, based on the weight of the solids in the feedstock composition. In embodiments, the same values apply with respect to the total amount of ash, slag, char and tar generated in the gasifier or by the process, based on the weight of the solids in the feedstock composition.

The raw syngas stream flows from the gasification zone to a quench zone at the bottom of the gasifier where the slag and raw syngas stream are cooled, generally to a temperature below 550° C., or below 500° C., or below 450° C. The quench zone contains water in a liquid state. The hot syngas from the gasification zone may be cooled by directly contacting the syngas stream with liquid water. The syngas stream can be bubbled through the pool of liquid water, or merely contact the surface of the water pool. In addition, the hot syngas stream may be cooled in a water jacketed chamber having a height that above the top surface of the water pool to allow the hot syngas to both contact the water pool and be cooled in the water jacketed chamber. Molten slag is solidified by the quench water and most of the ash, slag and char are transferred to the water in the quench tank. The partially cooled gas stream, having passed through the water in the quench zone, may be then discharged from the gasifier as a raw syngas stream and passed through a water scrubbing operation to remove any remaining entrained particulate matter.

The pressure in the quench zone is substantially the same as the pressure in the gasification zone located above the water level in the gasifier, and a portion of the quench water and solids at the bottom of the quench tank is removed by way of a lock hopper system. A stream of quench water carrying fine particles exits the gasifier quench zone in response to a liquid level controller and can be directed to a settler. The solids and water from the lock hopper may then flow into a water sump or settler where optionally the coarse particulate solids may be removed by screens or filter thereby producing a dispersion of fine particulate solids.

Each of the first and second raw syngas streams discharged from the gasification vessel includes such gasses as hydrogen, carbon monoxide, carbon dioxide and can include other gases such as methane, hydrogen sulfide and nitrogen depending on the fuel source and reaction conditions. Carbon dioxide in each of the first and second raw syngas streams discharged from the gasification vessel are desirably present in an amount of less than 20 mole %, or less than 18 mole %, or less than 15 mole %, or less than 13 mole %, or not more than 11 mole %, based on all moles of gases in the stream. Some nitrogen and argon can be present in the raw syngas stream depending upon the purity of the fuel and oxygen supplied to the process.

In embodiments, the raw syngas stream (the stream discharged from the gasifier and before any further treatment by way of scrubbing, shift, or acid gas removal) can have the following composition in mole % on a dry basis and based on the moles of all gases (elements or compounds in gaseous state at 25° C. and 1 atm) in the raw syngas stream:
a. $H_2$: 15 to 60, or 18 to 50, or 18 to 45, or 18 to 40, or 23 to 40, or 25 to 40, or 23 to 38, or 29 to 40, or 31 to 40
b. CO: 20 to 75, or 20 to 65, or 30 to 70, or 35 to 68, or 40 to 68, or 40 to 60, or 35 to 55, or 40 to 52
c. CO2:1.0 to 30, or 2 to 25, or 2 to 21, or 10 to 25, or 10 to 20
d. H2O: 2.0 to 40.0, or 5 to 35, or 5 to 30, or 10 to 30
e. CH4: 0.0 to 30, or 0.01 to 15, or 0.01 to 10, or 0.01 to 8, or 0.01 to 7, or 0.01 to 5, or 0.01 to 3, or 0.1 to 1.5, or 0.1 to 1
f. H2S: 0.01 to 2.0, or 0.05 to 1.5, or 0.1 to 1, or 0.1 to 0.5
g. COS: 0.05 to 1.0, or 0.05 to 0.7, or 0.05 to 0.3
h. Total sulfur: 0.015 to 3.0, or 0.02 to 2, or 0.05 to 1.5, or 0.1 to 1
i. N2: 0.0 to 5, or 0.005 to 3, or 0.01 to 2, or 0.005 to 1, or 0.005 to 0.5, or 0.005 to 0.3

The gas components can be determined by FID-GC and TCD-GC or any other method recognized for analyzing the components of a gas stream.

The molar hydrogen/carbon monoxide ratio is desirably at least 0.65, or at least 0.68, or at least 0.7, or at least 0.73, or at least 0.75, or at least 0.78, or at least 0.8, or at least 0.85, or at least 0.88, or at least 0.9, or at least 0.93, or at least 0.95, or at least 0.98, or at least 1.

The total amount of hydrogen and carbon monoxide relative to the total amount of syngas discharged from the gasifier on a dry basis is high, on the order of greater than 70 mole %, or at least 73 mole %, or at least 75 mole %, or at least 77 mole %, or at least 79 mole %, or at least 80 mole %, based on the syngas discharged.

In embodiments, each of the first and second dry syngas production expressed as gas volume discharged from the gasifier per kg of solid fuel (e.g. textiles and/or plastics and coal) charged to all locations on the gasifier is at least 1.7, or at least 1.75, or at least 1.8, or at least 1.85, or at least 1.87, or at least 1.9, or at least 1.95, or at least 1.97, or at least 2.0, in each case as N m3 gas/kg solids fed.

The carbon conversion efficiency for the production of each of the first and second syngas in one pass is good and can be calculated according to the following formula:

$$= \frac{\text{total carbon in feed} - \text{total carbon in char and tar}}{\text{total carbon in feed}} \times 100$$

The carbon conversion efficiency in the process in one pass can be at least 70%, or at least 73%, or at least 75%, or at least 77%, or at least 80%, or at least 82%, or at least 85%, or at least 88%, or at least 90%, or at least 93%.

In embodiments, each of the first and second raw syngas stream contains particulate solids in an amount of greater than 0 wt. % up to 30 wt. %, or greater than 0 wt. % up to 10 wt. %, or greater than 0 wt. % up to 5 wt. %, or greater than 0 wt. % up to 1 wt. %, or greater than 0 wt. % up to 0.5 wt. %, or greater than 0 wt. % up to 0.3 wt. %, or greater than 0 wt. % up to 0.2 wt. %, or greater than 0 wt. % up to 0.1 wt. %, or greater than 0 wt. % up to 0.05 wt. %, each based on the weight of solids in the feedstock composition. The amount of particulate solids in this case is determined by cooling the syngas stream to a temperature of below 200° C., such as would occur in a scrubbing operation.

In embodiments, the cold gas efficiency of the process to produce each of the first and second syngases using the textiles and/or plastics/solid fossil fuel as a percent can be calculated as:

$$= \frac{\text{Produced gas (mole)} \times HHV(MJ \text{ per mole})}{\text{Feedstock (kg)} \times HHV(MJ \text{ per kg})} \times 100$$

The cold gas efficiency is at least 60%, or at least 65%, or at least 66%, or at least 67%, or at least 68%, or at least 69%, or desirably at least 70%, or at least 71%, or at least 72%, or at least 73%, or at least 74%, or at least 75%, or at least 76%, or at least 77%, or at least 78%, or at least 79%.

In embodiments, hydrogen and carbon monoxide from the raw syngas stream discharged from the gasifier or from a scrubbed or purified syngas stream are not recycled or recirculated back to a gasification zone in a gasifier. Desirably, carbon dioxide from the raw syngas stream discharged from the gasifier or from a scrubbed or purified syngas stream is not recycled or recirculated back to a gasification zone in a gasifier. Desirably, no portion of the syngas stream discharged from the gasifier or from a scrubbed or purified syngas stream is recycled or recirculated back to a gasification zone in a gasifier. In embodiments, no portion of the syngas discharged from the gasifier is used to heat the gasifier. Desirably, no portion of the syngas made in the gasifier is burned to dry the solid fossil fuel.

The feedstock stream is gasified with the oxidizer such as oxygen desirably in an entrained flow reaction zone under conditions sufficient to generate a molten slag and ash. The molten slag and ash are separated from the syngas and quench cooled and solidified. In a partial oxidation reactor, the coal/size reduced textiles and/or plastics/water mixture is injected with oxygen and the coal/rubber will react with oxygen to generate a variety of gases, including carbon monoxide and hydrogen (syngas). The molten slag and unreacted carbon/size reduced textiles and/or plastics accumulate into a pool of water in the quench zone at the bottom part of the gasifier to cool and solidify these residues.

In embodiments, the gasification process is under slagging conditions, and the slag is discharged from the gasifier as a solid. Slag is cooled and solidified within the gasifier in a quench zone within the shell of the gasifier, and is discharged from the gasifier shell as a solid. The same applies to ash and char. These solids discharged from the gasifier are accumulated into a lock hopper which can then be emptied. The lock hopper is generally isolated from the gasifier and the quench zone within the gasifier.

The process can be practiced on an industrial scale and on a scale sufficient to provide syngas as a raw material to make chemicals on an industrial scale. At least 300 tons/day, or at least 500 t/d, or at least 750 t/d, or at least 850 t/d, or at least 1000 t/d, or at least 1250 t/d, and desirably at least 1500 t/d, or at least 1750 t/d, or even at least 2000 t/d of solids can be fed to the gasifier. The gasifier is desirably not designed to be mobile and is fixed to and above the ground, and desirably stationary during operations.

In embodiments, the syngas compositional variability within the second syngas stream is quite low over time. The compositional variability of the second syngas stream can be determined by taking at least 6 measurements of the concentration of the relevant gaseous compound in moles in across a time period that does not exceed the second time period but in no event exceeds 12 days, and excludes the transition periods. The mean concentration of the gaseous compound is determined over the 6 measurements. The absolute value of the difference between the number farthest away from the mean and the mean number is determined and divided into the mean number×100 to obtain a percent compositional variability.

The compositional variability of any one of:
a. CO amount, or
b. H2 amount, or
c. CO2 amount, or
d. CH4 amount, or
e. H2S amount, or
f. COS amount, or
g. H2+CO amount, or its molar ratio in sequence (e.g. H2:CO ratio), or
h. H2+CO+CO2 amount, or its molar ratio in sequence, or
i. H2+CO+CH4 amount, or its molar ratio in sequence, or
j. H2+CO+CO2+CH4 amount, or its molar ratio in sequence, or
k. H2S+COS amount, or its molar ratio in sequence, or
l. H2+CO+CO2+CH4+H2S+COS, or
m. Tar, or
n. char.

The molar compositional variability can be not more than 20%, or not more than 15%, or not more than 13%, or not more than 10%, or not more than 8%, or not more than 6%, or not more than 5%, or not more than 3%, or not more than 2%, during the shorter of a 12-day period or the time that textiles and/or plastics are gasified during the second time period. Desirably, the compositional elements are measured on (a), (b), (c), (d), (g), (h), (m), or (n), or any combination thereof.

In embodiments, variability within the first syngas stream and the variability within the second syngas stream are compared to each other to obtain a % switching variability, or in other words, the syngas variability generated by switching between the two feedstock compositions. It is desired that the variability present in the first syngas stream is not appreciably increased during the process of generating the second syngas stream. The second syngas variation can be less than, or no different than, or if higher can be similar to the syngas variation of the first syngas stream. The time periods to determine variations is set by the shorter of a 12-day period or the time that second syngas stream is generated during the second time period, and that time period is the same time period used for taking measurements in the solid fossil fuels only case. The measurements for the first syngas stream are taken within 1 month before switching to a second feedstock to make the second syngas stream. The variations in syngas composition made by each of the streams is measured according to the procedures states above. The second syngas variability is less than the first syngas variability, or the same as the first syngas variability, or not more than 25%, or not more than 20%, or not more than 15%, or not more than 10%, or not more than 5%, or not more than 4%, or not more than 3%, or not more than 2%, or not more than 1%, or not more than 0.5%, or not more than 0.25% greater than the first syngas variability. This can be calculated as:

$$\%SV = \frac{V_s - V_f}{V_f} \times 100$$

where % SV is percent syngas switching variability on one or more measured ingredients in the syngas composition; and
$V_s$ is the second syngas compositional variability; and
$V_f$ is the first syngas compositional variability. In the event that the % SV is negative, then the second syngas variability is less than the first syngas variability.

The components in each of the first and second syngas streams that are measured, and calculated into moles, over time to determine the variability within each stream include:
a. $H_2$, or
b. CO, or
c. CO2, or
d. H2O, or
e. CH4, or
f. H2S, or
g. COS, or
a. Total sulfur, or
b. molar ratio of CO2:CO, or
c. molar ratio of H2:CO, or
d. total H2S and COS
e. Char, or
f. Tar, or
g. Any combination of the above.

Desirably, the compositional elements measured (i), (m), or (i) and (j), (a)-(c) and (i)-(j) and (m).

In embodiments, the amount of CO2 generated in a second time period is similar to or less than the amount of carbon dioxide generated from a first time period. The process can be conducted such that the amount of $CO_2$ generated and contained in the second syngas is no more than 25%, or no more than 20%, or no more than 15%, or no more than 13%, or no more than 10%, or no more than 8%, or no more than 7%, or no more than 6%, or no more than 5%, or no more than 4%, or no more than 3%, or no more than 2%, or no more than 1%, or no more than 0.75%, or no more than 0.5%, or nor more than 0.25%, or no more than 0.15%, or no more than 0.1% of the amount of carbon dioxide generated and contained in the first syngas, or less. The percentage similarity can be calculated by subtracting the amount of $CO_2$ in the first syngas stream from the amount of $CO_2$ generated in a first second stream, and dividing that number by the CO2 generated in a syngas stream first syngas stream×100. Advantageously, if the number is negative, then the amount of CO2 generated in the second syngas is less than the amount of CO2 generated in the first syngas stream.

The polymers or articles having a recycle content are broadly named as Recycle PA (recycle polymers or articles). The polymers or articles are as described throughout this description. Recycle PA can be obtained in a reaction scheme as described herein, or can be obtained by way of a recycle content allotment, provided that the allotment has its origin in, or withdrawn from an inventory of allotments containing at least one allotment having its origin in, gasifying a feedstock containing at least some content of recycle plastic and/or recycle textiles. The "recycle content allotment" is a recycle content value that is transferred from an originating composition, compound or polymer at least a portion of which is obtained by or with the gasification of feedstock containing recycle plastic and/or recycle textiles, to a receiving composition, compound, or polymer (referred to herein as a "composition" for brevity) receiving the allotment. The recycle content value (whether by mass or percentage or any other unit of measure) can optionally be determined according to a standard system for tracking, allocating, and/or crediting recycle content among various compositions.

A recycle content allotment can include an allocation or a credit obtained with the transfer or use of a raw material. In embodiments, the composition receiving the recycle content allotment can be a non-recycle composition. As used herein, "non-recycle" means a composition, compound or polymer none of which was directly or indirectly derived from a high concentrated recycle derived syngas stream. As used herein, a "non-recycle feed" in the context of a feed to the gasifier means a feed that does not contain a recycle waste stream of any kind. Once a non-recycle feed, composition, compound, polymer, or article obtains a recycle content allotment (e.g. either through a credit or allocation), it becomes a recycle content feed, composition, compound, polymer or article, or in this case, a Recycle PA.

As used herein, the term "recycle content allocation" is a type of recycle content allotment, where the entity or person supplying the composition sells or transfers the composition to the receiving entity, and the entity that made the composition has an allotment at least a portion of which can be associated with the composition sold or transferred by the supplying entity to the receiving entity. The supplying entity or person can be controlled by the same entity or a variety of affiliates that are ultimately controlled or owned at least in part by a parent entity ("Family of Entities"), or they can be from a different Family of Entities. The term "recycle content credit" is a type of recycle content allotment, where the allotment is available for sale or transfer by other than the supplier of the composition that is transferred to the receiving entity or person.

The Recycle PA can have associated with it a recycle content allotment and may or may not contain a physical component that is traceable to a high concentrated recycle derived syngas stream. For example, the (i) manufacturer of the product can operate within a legal framework, or an association framework, or an industry recognized framework for making a claim to a recycle content through, for example, a system of credits transferred to the product manufacturer regardless of where or from whom the high concentrated recycle derived syngas stream, or downstream products made thereby, or reactant feedstocks to make the polymer and/or article, is purchased or transferred, or (ii) a supplier of the high concentrated recycle derived syngas stream or downstream products made thereby ("supplier") operates within an allocation framework that allows for allocating a recycle content value to a portion or all of the high concentrated recycle derived syngas stream or downstream products made thereby and to transfer the allotment to the manufacturer of the product or any intermediary who obtains a supply of high concentrated recycle derived syngas stream or a downstream product thereof, from the supplier. In this system, one need not trace the source of a polymer/article reactant back to the manufacture of high concentrated recycle derived syngas stream or back to any atoms contained in the high concentrated recycle derived syngas stream, but rather can use any polymer/article reactant made by any process and have associated with such polymer/article reactant, or have associated with the Recycle PA, a recycle content allotment. In an embodiment, the Recycle PA reactants do not contain recycle content.

In an embodiment, the Recycle PA has associated with it, or contains, or is labelled, advertised, or certified as containing recycle content in an amount of at least 0.01 wt. %, or at least 0.05 wt. %, or at least 0.1 wt. %, or at least 0.5 wt. %, or at least 0.75 wt. %, or at least 1 wt. %, or at least 1.25 wt. %, or at least 1.5 wt. %, or at least 1.75 wt. %, or at least 2 wt. %, or at least 2.25 wt. %, or at least 2.5 wt. %, or at least 2.75 wt. %, or at least 3 wt. %, or at least 3.5 wt. %, or at least 4 wt. %, or at least 4.5 wt. %, or at least 5 wt. %, or at least 6 wt. %, or at least 7 wt. %, or at least 10 wt. %, or at least 15 wt. %, or at least 20 wt. %, or at least 25 wt. %, or at least 30 wt. %, or at least 35 wt. %, or at least 40 wt. %, or at least 45 wt. %, or at least 50 wt. %, or at least 55 wt. %, or at least 60 wt. %, or at least 65 wt. % and/or the amount can be up to 100 wt. %, or up to 95 wt. %, or up to 90 wt. %, or up to 80 wt. %, or up to 70 wt. %, or up to 60 wt. %, or up to 50 wt. %, or up to 40 wt. %, or up to 30 wt. %, or up to 25 wt. %, or up to 22 wt. %, or up to 20 wt. %, or up to 18 wt. %, or up to 16 wt. %, or up to 15 wt. %, or up to 14 wt. %, or up to 13 wt. %, or up to 11 wt. %, or up to 10 wt. %, or up to 8 wt. %, or up to 6 wt. %, or up to 5 wt. %, or up to 4 wt. %, or up to 3 wt. %, or up to 2 wt. %, or up to 1 wt. %, or up to 0.9 wt. %, or up to 0.8 wt. %, or up to 0.7 wt. %. The recycle content associated with the Recycle PA can be associated by applying an allotment (credit or allocation) to any polymer and/or article made or sold. The allotment can be contained in an inventory of allotments created, maintained or operated by or for the Recycle PA manufacturer. The allotment can be obtained from any source along any manufacturing chain of products provided that its origin is in gasifying a feedstock containing a recycle plastic and/or recycle textile.

The amount of recycle content in a polymer/article reactant, or the amount of recycle content applied to the Recycle PA, or the amount of recycle content polymer/article reactant (r-reactant) needed to feed the reactor to claim a desired amount of recycle content in the Recycle PA in the event that all the recycle content from the r-reactant is applied to the Recycle PA, can be determined or calculated by any of the following methods:

(i) the amount of an allotment associated with the r-reactant used to feed the reactor is determined by the amount certified or declared by the supplier of the reactant transferred to the manufacturer of the Recycle PA, or (ii) the amount of allocation declared by the Recycle PA manufacturer as fed to the Recycle PA reactor, or (iii) using a mass balance approach to back-calculate the minimum amount of recycle content in the feedstock from an amount of recycle content declared, advertised, or accounted for by the manufacturer, whether or not accurate, as applied to the Recycle PA product, (iv) blending of non-recycle content with recycle content feedstock polymer/article reactant or associating recycle content to a portion of the feedstock, using pro-rata mass approach In one embodiment, the Recycle PA manufacturer can make Recycle PA, or process a polymer/article reactant and make a Recycle PA, or make Recycle PA by obtaining any source of a polymer/article reactant composition from a supplier, whether or not such polymer/article reactant composition has any recycle content, and either:
  i. from the same supplier of the polymer/article reactant composition, also obtain a recycle content allotment, or
  ii. from any person or entity, obtaining a recycle content allotment without a supply of a polymer/article reactant composition from said person or entity transferring said recycle content allotment.

The allotment in (i) is obtained from a polymer/article reactant supplier, and the polymer/article reactant supplier also supplies polymer/article reactant to the Recycle PA manufacturer or within its Family of Entities. The circumstance described in (i) allows a Recycle PA manufacturer to obtain a supply of a polymer/article reactant composition that is a non-recycle content polymer/article reactant, yet obtain a recycle content allotment from the polymer/article reactant supplier. In one embodiment, the polymer/article reactant supplier transfers a recycle content allotment to the Recycle PA manufacturer and a supply of polymer/article reactant to the Recycle PA manufacturer, where the recycle content allotment is not associated with the polymer/article reactant supplied, or even not associated with any polymer/article reactant made by the polymer/article reactant supplier. The recycle content allotment does not have to be tied to an amount of recycle content in a polymer/article reactant composition or to any monomer used to make Recycle PA, but rather the recycle content allotment transferred by the polymer/article reactant supplier can be associated with other products having their origin in high concentrated recycle derived syngas stream other than those in a reaction scheme to make polymer and/or articles. For example, the polymer/article reactant supplier can transfer to the Recycle PA manufacturer a recycle content associated with r-butyraldehyde and also supply a quantity of propionic anhydride even though r-butyraldehyde is not used directly or via downstream products in the synthesis of the polymer and/or article such as a cellulose diacetate. This allows flexibility among the polymer/article reactant supplier and Recycle PA manufacturer to apportion a recycle content among the variety of products they each make.

In one embodiment, the polymer/article reactant supplier transfers a recycle content allotment to the Recycle PA manufacturer and a supply of polymer/article reactant to the Recycle PA manufacturer, where the recycle content allotment is associated with polymer/article reactant. In this case, the polymer/article reactant transferred does not have to be a r-reactant, but can be any polymer/article reactant so long as the allocation is associated with a manufacture of polymer/article reactant. Optionally, the polymer/article reactant being supplied can r-reactant and at least a portion of the recycle content allotment being transferred can be the recycle content in the r-reactant. The recycle content allotment transferred to the Recycle PA manufacturer can be up front with the polymer/article reactant supplied in installments, or with each polymer/article reactant installment, or apportioned as desired among the parties.

The allotment in (ii) is obtained by the Recycle PA manufacturer (or its Family of Entities) from any person or entity without obtaining a supply of polymer/article reactant from the person or entity. The person or entity can be a polymer/article reactant manufacturer that does not supply polymer/article reactant to the Recycle PA manufacturer or its Family of Entities, or the person or entity can be a manufacturer that does not make polymer/article reactant. In either case, the circumstances of (ii) allows a Recycle PA manufacturer to obtain a recycle content allotment without having to purchase any polymer/article reactant from the entity supplying the recycle content allotment. For example, the person or entity may transfer a recycle content allotment through a buy/sell model or contract to the Recycle PA manufacturer or its Family of Entities without requiring purchase or sale of a allotment (e.g. as a product swap of products that are not polymer/article reactant), or the person or entity may outright sell the allotment to the Recycle PA manufacturer or one among its Family of Entities. Alternatively, the person or entity may transfer a product, other than a polymer/article reactant, along with its associated recycle content allotment to the Recycle PA manufacturer. This can be attractive to a Recycle PA manufacturer that has a diversified business making a variety of products other than Recycle PA requiring raw materials other than a polymer/article reactant that the person or entity can supply to the Recycle PA manufacturer.

The allotment can be deposited into a recycle inventory (e.g. an inventory of allotments). In one embodiment, the allotment is an allocation created by the manufacturer of the high concentrated recycle derived syngas stream. The Recycle PA manufacturer cam also make a polymer and/or article, whether or not a recycle content is applied to the polymer and/or article and whether or not recycle content, if applied to the polymer and/or article, is drawn from the inventory. For example, the Recycle PA manufacturer may:
  a. deposit the allotment into an inventory and merely store it; or
  b. deposit the allotment into an inventory and apply allotments from the inventory to products other than polymer and/or articles made by the Recycle PA manufacturer, or
  c. sell or transfer an allocation from the inventory into which at least one allotment, obtained as noted above, was deposited.

If desired, however, from that inventory, any recycle content allotment can be deducted in any amount and applied to a polymer and/or article to make a Recycle PA. For example, a Recycle inventory of allotments can be generated having a variety of sources for creating the allotments. Some recycle content allotments (credits) can have their origin in methanolysis of recycle waste, or from gasification of other types of recycle waste, or from mechanical recycling of waste plastic or metal recycling, and/or from pyrolyzing recycle waste, or from any other chemical or mechanical recycling technology. The recycle inventory may or may not track the origin or basis of obtaining a recycle content value, or the inventory may not allow one to associate the origin or basis of an allocation to the allocation applied to Recycle PA. It is sufficient that an allocation is deducted from an allocation inventory and applied to Recycle PA regardless of the source or origin of the allocation, provided that a recycle content allotment derived from gasifying a solid fossil fuel and recycle plastic and/or recycle textiles is present in the allotment inventory as the time of withdrawal, or a recycle content allotment is obtained by the Recycle PA manufacturer as specified in step (i) or step (ii), whether or not that recycle content allotment is actually deposited into the inventory. In one embodiment, the recycle content allotment obtained in step (i) or (ii) is deposited into an inventory of allotments. In one embodiment, the recycle content allotment deducted from the inventory and applied to the Recycle PA originates from gasifying a feedstock containing solid fossil fuel and recycle plastic and/or recycle textiles.

As used throughout, the inventory of allotments can be owned by the Recycle PA manufacturer, operated by the Recycle PA manufacturer, owned or operated by other than the Recycle PA manufacturer but at least in part for the Recycle PA manufacturer, or licensed by the Recycle PA manufacturer. Also, as used throughout, the Recycle PA manufacturer may also include its Family of Entities. For example, while the Recycle PA manufacturer may not own or operate the inventory, one among its Family of Entities may own such a platform, or license it from an independent vendor, or operate it for the Recycle PA manufacturer. Alternatively, an independent entity may own and/or operate the inventory and for a service fee operate and/or manage at least a portion of the inventory for the Recycle PA manufacturer.

In one embodiment, the Recycle PA manufacturer obtains a supply of polymer/article reactant from a supplier, and also obtains an allotment from the supplier, where such allotment is derived from gasifying a feedstock containing recycle plastic and/or recycle textiles, and optionally the allotment is associated with the polymer/article reactant supplied by the supplier. In one embodiment, at least a portion of the allotment obtained by the Recycle PA manufacturer is either:
   a. applied to Recycle PA made by the supply of polymer/article reactant;
   b. applied to Recycle PA not made by the supply of polymer/article reactant, such as would be the case where Recycle PA is already made and stored in inventory or future made Recycle PA; or
   c. deposited into an inventory from which is deducted an allocation applied to Recycle PA (the Recycle PA applied allocation) and the deposited allocation either does, or does not, contribute to the amount of allocations from which the Recycle PA applied allocation is drawn.
   d. deposited into an inventory and stored.

It is not necessary in all embodiments that r-reactant is used to make Recycle PA composition or that the Recycle PA was obtained from a recycle content allotment associated with a polymer/article reactant composition. Further, it is not necessary that an allotment be applied to the feedstock for making the Recycle PA to which recycle content is applied. Rather, as noted above, the allotment, even if associated with a polymer/article reactant composition when the polymer/article reactant composition is obtained, can be deposited into an electronic inventory. In one embodiment, however, r-reactant is used to make the Recycle PA composition. In one embodiment, the Recycle PA is obtained from a recycle content allotment associated with an r-reactant. In one embodiment, at least a portion of r-reactant allotments are applied to Recycle PA to make a Recycle PA.

There can now also be provided a package or a combination of a Recycle PA and a recycle content identifier associated with Recycle PA, where the identifier is or contains a representation that the Recycle PA contains, or is sourced from or associated with a recycle content. The package can be any suitable package for containing a polymer and/or article, such as a plastic or metal drum, railroad car, isotainer, totes, polytotes, IBC totes, bottles, compressed bales, jerricans, and polybags. The identifier can be a certificate document, a product specification stating the recycle content, a label, a logo or certification mark from a certification agency representing that the article or package contains contents or the Recycle PA contains, or is made from sources or associated with recycle content, or it can be electronic statements by the Recycle PA manufacturer that accompany a purchase order or the product, or posted on a website as a statement, representation, or a logo representing that the Recycle PA contains or is made from sources that are associated with or contain recycle content, or it can be an advertisement transmitted electronically, by or in a website, by email, or by television, or through a tradeshow, in each case that is associated with Recycle PA. The identifier need not state or represent that the recycle content is derived from gasifying a feedstock containing recycle plastic and/or recycle textiles. Rather, the identifier can merely convey or communicate that the Recycle PA has or is sourced from a recycle content, regardless of the source.

In one embodiment, one may communicate recycle content information about the Recycle PA to a third party where such recycle content information is based on or derived from at least a portion of the allocation or credit. The third party may be a customer of the Recycle PA manufacturer or supplier, or may be any other person or entity or governmental organization other than the entity owning the Recycle PA. The communication may electronic, by document, by advertisement, or any other means of communication.

In one embodiment, there is provided a system or package comprising:
   a. Recycle PA or article made thereby, and
   b. an identifier such as a credit, label or certification associated with said Recycle PA or article made thereby, where the identifier is a representation that the polymer and/or article or article made thereby has, or is sourced from, a recycle content.

The system can be a physical combination, such as package having at least Recycle PA as its contents and the package has a label, such as a logo, that the contents such as the Recycle PA has or is sourced from a recycle content. Alternatively, the label or certification can be issued to a third party or customer as part of a standard operating procedure of an entity whenever it transfers or sells Recycle PA having or sourced from recycle content. The identifier does not have to be physically on the Recycle PA or on a package, and does not have to be on any physical document that accompanies or is associated with the Recycle PA. For example, the identifier can be an electronic credit transferred electronically by the Recycle PA manufacturer to a customer in connection with the sale or transfer of the Recycle PA product, and by sole virtue of being a credit, it is a representation that the Recycle PA has recycle content. The identifier itself need only convey or communicate that the Recycle PA has or is sourced from a recycle content, regardless of the source. In one embodiment, articles made from the Recycle PA may have the identifier, such as a stamp or logo embedded or adhered to the article. In one embodiment, the identifier is an electronic recycle content credit from any source. In one embodiment, the identifier is an electronic recycle content credit having its origin in gasifying a feedstock containing recycle plastic and/or recycle textiles.

The polymer and/or article composition is made from any source of a polymer/article reactant composition, whether or not the polymer/article reactant composition is a r-reactant. Once a Recycle PA composition is made, it can be designated as having recycle content based on and derived from at least a portion of the allotment, again whether or not the r-reactant is used to make the Recycle PA composition. The allocation can be withdrawn or deducted from inventory. The amount of the deduction and/or applied to the Recycle PA can correspond to any of the methods described above, e.g. a mass balance approach.

In an embodiment, a Recycle PA composition can be made by having an inventory of allocations, and reacting a polymer/article reactant composition in a synthetic process to make a Recycle PA, and applying a recycle content to that Recycle PA to thereby obtain a Recycle PA by deducting an amount of allocation from an inventory of allocations. A Recycle PA manufacturer may have an inventory of allocations by itself or one among its Family of Entities owning, possessing, or operating the inventory, or a third party operating at least a portion of the inventory for the Recycle PA manufacturer or its Family of Entities or as a service provided to the Recycle PA manufacturer or one among its Family of Entities. The amount of allocation deducted from inventory is flexible and will depend on the amount of recycle content applied to the Recycle PA. It should be at least sufficient to correspond with at least a portion if not the entire amount of recycle content applied to the Recycle PA. The method of calculation can be a mass balance approach or the methods of calculation described above. The inventory of allocations can be established on any basis and may be a mix of basis, provided that at least some amount of allocation in the inventory is attributable to gasifying a feedstock containing recycle plastic and/or recycle textiles. The recycle content allotment applied to the Recycle PA does not have to have its origin in gasifying a feedstock containing recycle plastic and/or recycle textiles, and instead can have its origin in any other method of generating allocations from recycle waste, such as through methanolysis or gasification of recycle waste, provided that the inventory of allotments also contains an allotment or has an allotment deposit having its origin in gasifying a feedstock containing recycle plastic and/or recycle textiles. In one embodiment, however, the recycle content applied to the Recycle PA is an allotment obtained from gasifying a feedstock containing recycle plastic and/or recycle textiles.

The following are examples of designating or declaring a recycle content to Recycle PA or a recycle content to a polymer/article reactant composition:

1. A Recycle PA manufacturer applies at least a portion of an allotment to a polymer and/or article composition where the allotment is associated with a recycle plastic and/or recycle textiles content syngas, and the polymer/article reactant composition used to make the Recycle PA did not contain any recycle content or it did contain recycle content; or
2. A Recycle PA manufacturer applies at least a portion of an allotment to a polymer and/or article composition where the allotment is derived directly or indirectly with a recycle content polymer/article reactant, whether or not such polymer/article reactant volume is used to make the Recycle PA; or
3. A Recycle PA manufacturer applies at least a portion of an allotment to a Recycle PA composition where the allotment is derived directly or indirectly with a recycle content polymer/article reactant, and the recycle content polymer/article reactant is used as a feedstock to make the Recycle PA to which the allotment is applied, and:
   a. all of the recycle content in the r-polymer/article reactant is applied to determine the amount of recycle content in the Recycle PA, or
   b. only a portion of the recycle content in the r-polymer/article reactant is applied to determine the amount of recycle content applied to the Recycle PA, the remainder stored in inventory for use to future Recycle PA, or for application to other existing Recycle PA made from r-polymer/article reactant not containing any recycle content, or to increase the recycle content on an existing Recycle PA, or a combination thereof, or
   c. none of the recycle content in the r-polymer/article reactant is applied to the Recycle PA and instead is stored in an inventory, and a recycle content from any source or origin is deducted from the inventory and applied to Recycle PA; or
4. A Recycle PA manufacturer applies at least a portion of an allotment to a polymer/article reactant composition used to make a Recycle PA to thereby obtain a Recycle PA, where the allotment was obtained with the transfer or purchase of the same polymer/article reactant composition used to make the Recycle PA and the allotment is associated with the recycle content in a polymer/article reactant composition; or
5. A Recycle PA manufacturer applies at least a portion of an allotment to a polymer/article reactant composition used to make a Recycle PA to thereby obtain a Recycle PA, where the allotment was obtained with the transfer or purchase of the same polymer/article reactant composition used to make the Recycle PA and the allotment is not associated with the recycle content in a polymer/article reactant composition but rather on the recycle content of a monomer used to make the polymer/article reactant composition; or
6. A Recycle PA manufacturer applies at least a portion of an allotment to a polymer/article reactant composition used to make a Recycle PA to thereby obtain a Recycle PA, where the allotment was not obtained with the transfer or purchase of the polymer/article reactant composition and the allotment is associated with the recycle content in the polymer/article reactant composition; or
7. A Recycle PA manufacturer applies at least a portion of an allotment to a polymer/article reactant composition used to make a Recycle PA to thereby obtain a Recycle PA, where the allotment was not obtained with the transfer or purchase of the polymer/article reactant composition and the allotment is not associated with the recycle content in the polymer/article reactant composition but rather with the recycle content of any monomers used to make the polymer/article reactant composition, such as an allotment associated with recycle content in propylene or ethylene; or
8. A Recycle PA manufacturer obtains an allotment having it origin in gasifying a feedstock containing recycle plastic and/or recycle textiles, and:
   a. no portion of the allotment is applied to a polymer/article reactant composition to make Recycle PA and at least a portion is applied to Recycle PA to make a Recycle PA; or
   b. less than the entire portion is applied to a polymer/article reactant composition used to make Recycle PA and the remainder is stored in inventory or is applied to future made Recycle PA or is applied to existing Recycle PA in inventory.

In one embodiment, the Recycle PA, or articles made thereby, can be offered for sale or sold as Recycle PA containing or obtained with recycle content. The sale or offer for sale can be accompanied with a certification or representation of the recycle content claim made in association with the Recycle PA or article made with the Recycle PA.

The obtaining of an allocation and designating (whether internally such as through a bookkeeping or an inventory tracking software program or externally by way of declaration, certification, advertising, representing, etc.) can be by the Recycle PA manufacturer or within the Recycle PA manufacturer Family of Entities. The designation of at least a portion of the Recycle PA as corresponding to at least a portion of the allotment (e.g. allocation or credit) can occur through a variety of means and according to the system employed by the Recycle PA manufacturer, which can vary from manufacturer to manufacturer. For example, the designation can occur internally merely through a log entry in the books or files of the Recycle PA manufacturer or other inventory software program, or through an advertisement or statement on a specification, on a package, on the product, by way of a logo associated with the product, by way of a certification declaration sheet associated with a product sold, or through formulas that compute the amount deducted from inventory relative to the amount of recycle content applied to a product.

Optionally, the Recycle PA can be sold. In one embodiment, there is provided a method of offering to sell or selling polymer and/or articles by:
  a. a Recycle PA manufacturer or its Family of Entities obtaining a recycle content allocation, and the allocation can be obtained by any of the means described herein and can be deposited into inventory, the recycle content allocation having its origin in gasification of a feedstock containing a recycle plastic and/or recycle textiles,
  b. converting a polymer/article reactant composition in a synthetic process to make a polymer and/or article composition, and the polymer/article reactant composition can be any polymer/article reactant composition or a r-polymer/article reactant composition,
  c. designating (e.g. assigning or associating) a recycle content to at least a portion of the polymer and/or article composition from an inventory of allocations, where the inventory contains at least one entry that is an allocation having its origin in gasification of a feedstock containing recycle plastic and/or recycle textiles. The designation can be the amount of allocation deducted from inventory, or the amount of recycle content declared or determined by the Recycle PA manufacturer in its accounts. Thus, the amount of recycle content does not necessarily have to be applied to the Recycle PA product in a physical fashion. The designation can be an internal designation to or by the Recycle PA manufacturer or its Family of Entities or a service provider in contractual relationship to the Recycle PA manufacturer or its Family of Entities, and
  d. offering to sell or selling the polymer and/or article composition as containing or obtained with recycle content corresponding at least in part with such designation. The amount of recycle content represented as contained in the Recycle PA sold or offered for sale has a relationship or linkage to the designation. The amount of recycle content can be a 1:1 relationship in the amount of recycle content declared on a Recycle PA offered for sale or sold and the amount of recycle content assigned or designated to the Recycle PA by the Recycle PA manufacturer.

The steps described need not be sequential, and can be independent from each other. For example, the step a) of obtaining an allocation and the step of making Recycle PA from a polymer/article reactant composition can be simultaneous and related if one employs a r-reactant composition to make the Recycle PA since the r-reactant is both a polymer/article reactant composition and has a recycle content allocation associated with it.

As used throughout, the step of deducting an allocation from an inventory of allocations does not require its application to a Recycle PA product. The deduction also does not mean that the quantity disappears or is removed from the inventory logs. A deduction can be an adjustment of an entry, a withdrawal, an addition of an entry as a debit, or any other algorithm that adjusts inputs and outputs based on an amount recycle content associated with a product and one or a cumulative amount of allocations on deposit in the inventory. For example, a deduction can be a simple step of a reducing/debit entry from one column and an addition/credit to another column within the same program or books, or an algorithm that automates the deductions and entries/additions and/or applications or designations to a product slate. The step of applying an allocation to a Recycle PA product where such allocation was deducted from inventory also does not require the allocation to be applied physically to a Recycle PA product or to any document issued in association with the Recycle PA product sold. For example, a Recycle PA manufacturer may ship Recycle PA product to a customer and satisfy the "application" of the allocation to the Recycle PA product by electronically transferring a recycle content credit to the customer.

In one embodiment, the amount of recycle content in the r-reactant or in the Recycle PA will be based on the allocation or credit obtained by the manufacturer of the Recycle PA composition or the amount available in the Recycle PA manufacturer's inventory of allotments. A portion or all of the allocation or credit obtained by or in the possession of a manufacturer of Recycle PA can be designated and assigned to a r-reactant or Recycle PA on a mass balance basis. The assigned value of the recycle content to the r-reactant or Recycle PA should not exceed the total amount of all allocations and/or credits available to the manufacturer of the Recycle PA or other entity authorized to assign a recycle content value to the Recycle PA.

There is now also provided a method of introducing or establishing a recycle content in a polymer and/or article without necessarily using an r-polymer/article reactant feedstock. In this method,
  a. A syngas supplier makes a high concentrated recycle derives syngas stream and
  b. a polymer and/or article manufacturer:
    i. obtains an allotment derived from said recycle plastic and/or recycle textiles content syngas from the supplier or a third-party transferring said allotment,
    ii. makes a polymer and/or article from a polymer/article reactant, and
    iii. associates at least a portion of the allotment with at least a portion of the polymer and/or article, whether or not the polymer/article reactant used to make the polymer and/or article contains a recycle content.

In this method, the polymer and/or article manufacturer need not purchase r-polymer/article reactant from any entity or from the supplier of polymer/article reactant, and does not require the polymer and/or article manufacturer to purchase a polymer/article reactant from a particular source or supplier, and does not require the polymer and/or article manufacturer to use or purchase a polymer/article reactant composition having r-polymer/article reactant in order to successfully establish a recycle content in the polymer and/or article composition. The polymer/article reactant manufacturer may use any source of polymer/article reactant and apply at least a portion of the allocation or credit to at least a portion of the polymer/article reactant feedstock or to at least a portion of the polymer and/or article product. The association by the polymer and/or article manufacturer may come in any form, whether by on in its inventory, internal accounting methods, or declarations or claims made to a third party or the public.

There is also provided a use for a polymer/article reactant, the use including converting r-polymer/article reactant in any synthetic process to make Recycle PA.

There is also provided a use for a polymer/article reactant that includes converting a polymer/article reactant in a synthetic process to make polymer and/or articles and applying at least a portion of an allotment to the polymer and/or article to the polymer/article reactant, where the allotment has its origin in gasifying a feedstock containing recycle plastic and/or recycle textiles or has its origin in an inventory of allotments where at least one deposit made into the inventory has its origin in gasifying a feedstock containing recycle plastic and/or recycle textiles.

In one embodiment, there is provided a polymer and/or article composition that is obtained by any of the methods described above.

The polymer/article reactant, such a polymer/article reactant can be stored in a storage vessel and transferred to a Recycle PA manufacturing facility by way of truck, pipe, or ship, or as further described below, the polymer/article reactant production facility can be integrated with the Recycle PA facility. The polymer/article reactant may be shipped or transferred to the operator or facility that makes the polymer and/or article.

In an embodiment, the process for making Recycle PA can be an integrated process. One such example is a process to make Recycle PA by:
  a. gasifying a feedstock containing recycle plastic and/or recycle textiles to make a high concentrated recycle derived syngas stream;
  b. reacting said syngas or a non-recycle content syngas made in the gasifier in a reaction scheme to make a polymer/article reactant composition;
  c. reacting any polymer/article reactant in a synthetic process to make a polymer and/or article;
  d. depositing an allotment into an inventory of allotments, said allotment originating from gasifying a feedstock containing recycle plastic and/or recycle textiles; and
  e. applying any allotment from said inventory to the polymer and/or article to thereby obtain a recycle content polymer and/or article composition.

In one embodiment, one may integrate two or more facilities and make Recycle PA. The facilities to make Recycle PA, the polymer/article reactant, or the syngas can be stand-alone facilities or facilities integrated to each other. For example, one may establish a system of producing and consuming a polymer/article reactant composition, as follows:
  a. provide a polymer/article reactant manufacturing facility configured to produce a polymer/article reactant composition;
  b. provide a polymer and/or article manufacturing facility having a reactor configured to accept a polymer/article reactant composition from the polymer/article reactant manufacturing facility; and
  c. a supply system providing fluid communication between these two facilities and capable of supplying a polymer/article reactant composition from the polymer/article reactant manufacturing facility to the polymer and/or article manufacturing facility, whether either the polymer and/or article manufacturing facility makes Recycle PA or the polymer/article reactant facility makes a recycle content polymer and/or article reactant.

The Recycle PA manufacturing facility can make Recycle PA by accepting any polymer/article reactant composition from the polymer/article reactant manufacturing facility and applying a recycle content to Recycle PA made with the polymer/article reactant composition by deducting allotments from its inventory and applying them to the Recycle PA, optionally in amounts using the methods described above. The allotments obtained and stored in inventory can be obtained by any of the methods described above, and need not necessarily be allotments associated with r-polymer/article reactant.

In one embodiment, there is also provided a system for producing Recycle PA as follows:
  a. Provide a gasification manufacturing facility configured to produce an output composition comprising a high concentrated recycle derived syngas stream;
  b. provide a polymer/article reactant manufacturing facility configured to accept a high concentrated recycle derived syngas stream from the gasification manufacturing facility and making, through a reaction scheme one or more downstream products of said syngas to make an output composition comprising a polymer/article reactant composition;
  c. provide a polymer and/or article (Recycle PA) manufacturing facility having a reactor configured to accept a polymer/article reactant composition and making an output composition comprising a recycle content Recycle PA; and
  d. a supply system providing fluid communication between at least two of these facilities and capable of supplying the output composition of one manufacturing facility to another one or more of said manufacturing facilities.

The Recycle PA manufacturing facility can make Recycle PA. In this system, the gasification manufacturing facility can have its output in fluid communication with the polymer/article reactant manufacturing facility which in turn can have its output in fluid communication with the Recycle PA manufacturing facility. Alternatively, the manufacturing facilities of a) and b) alone can be in fluid communication, or only b) and c). In the latter case, the Recycle PA manufacturing facility can make Recycle PA directly by having the recycle plastic and/or recycle textiles content syngas produced in the gasification manufacturing facility converted all the way to Recycle PA, or indirectly by accepting any polymer/article reactant composition from the polymer/article reactant manufacturing facility and applying a recycle content to Recycle PA by deducting allotments from its inventory and applying them to the Recycle PA, optionally in amounts using the methods described above. The allotments obtained and stored in inventory can be obtained by any of the methods described above, The fluid communication can be gaseous or liquid or both The fluid communication need not be continuous and can be interrupted by storage tanks, valves, or other purification or treatment facilities, so long as the fluid can be transported from the manufacturing facility to the subsequent facility through an interconnecting pipe network and without the use of truck, train, ship, or airplane. Further, the facilities may share the same site, or in other words, one site may contain two or more of the facilities. Additionally, the facilities may also share storage tank sites, or storage tanks for ancillary chemicals, or may also share utilities, steam or other heat sources, etc., yet also be considered as discrete facilities since their unit operations are separate. A facility will typically be bounded by a battery limit.

In one embodiment, the integrated process includes at least two facilities co-located within 5, or within 3, or within 2, or within 1 mile of each other (measured as a straight line). In one embodiment, at least two facilities are owned by the same Family of Entities.

In an embodiment, there is also provided an integrated r-olefin and Recycle PA generating and consumption system. This system includes:
a. Provide a gasification manufacturing facility configured to produce an output composition comprising a high concentrated recycle derived syngas stream;
b. provide a polymer/article reactant manufacturing facility configured to accept a high concentrated recycle derived syngas stream from the gasification manufacturing facility and making, through a reaction scheme one or more downstream products of said syngas to make an output composition comprising a polymer/article reactant composition;
c. provide a polymer and/or article (Recycle PA) manufacturing facility having a reactor configured to accept a polymer/article reactant composition and making an output composition comprising a recycle content Recycle PA; and
d. a piping system interconnecting at least two of said facilities, optionally with intermediate processing equipment or storage facilities, capable of taking off the output composition from one facility and accept said output at any one or more of the other facilities.

The system does not necessarily require a fluid communication between the two facilities, although fluid communication is desirable. In this system, ethylene or propylene made at the olefin manufacturing facility can be delivered to the polymer/article reactant facility through the interconnecting piping network that can be interrupted by other processing equipment, such as treatment, purification, pumps, compression, or equipment adapted to combine streams, or storage facilities, all containing optional metering, valving, or interlock equipment. The equipment can be a fixed to the ground or fixed to structures that are fixed to the ground. The interconnecting piping does not need to connect to the polymer/article reactant reactor or the cracker, but rather to a delivery and receiving point at the respective facilities. The same concept applies between the polymer/article reactant facility and the Recycle PA facility. The interconnecting pipework need not connect all three facilities to each other, but rather the interconnecting pipework can be between facilities a)-b), or b)-c), or between a)-b)-c).

What we claim is:

1. A process for making a high concentrated recycle derived material comprising:
a. making a first syngas in a gasifier in a first gasification process by gasifying a first feedstock that comprises solid fossil fuel;
b. making a second high concentrated recycle derived syngas in said gasifier in a second gasification process by gasifying a second feedstock that comprises solid fossil fuel and Recycle Polymer;
C. using at least a portion of the second high concentrated recycle derived syngas as a feedstock in a reaction scheme to produce at least one high concentrated recycle derived material;
wherein said second feedstock contains Recycle Polymer in an amount that is higher than the amount of Recycle Polymer used, if any, in a first feedstock; and
wherein the amount of $CO_2$ generated in the second gasification process is no more than 20% greater than the amount of $CO_2$ generated in the first gasification process.

2. The process according to claim 1, wherein the amount of $CO_2$ generated in the second gasification process is no more than 10% greater than the amount of $CO_2$ generated in the first gasification process.

3. The process according to claim 1, wherein the second feedstock contains not more than 0.5 wt % biomass, based on the weight of the solids in the feedstock.

4. The process according to claim 1, wherein the at least one high concentrated recycle derived material is chosen from a high concentrated recycle derived cellulose ester reactant, a high concentrated recycle derived cellulose ester, a high concentrated recycle derived acetic acid, a high concentrated recycle derived acetic anhydride, a high concentrated recycle derived methanol, a high concentrated recycle derived methyl acetate, a high concentrated recycle derived cellulose ester fiber, a high concentrated recycle derived textile, or a high concentrated recycle derived nonwoven web.

5. The process according to claim 4, wherein the at least one high concentrated recycle derived material is a high concentrated recycle derived cellulose ester that is biodegradable and compostable.

6. The process according to claim 1, wherein the at least one high concentrated recycle derived material is a high concentrated recycle derived polymer reactant, wherein said high concentrated recycle derived polymer reactant is made by reacting said second high concentrated recycle derived syngas to make the high concentrated recycle derived polymer reactant optionally through one or more high concentrated recycle derived chemical intermediates.

7. A process of making a high concentrated recycle derived polymer, comprising reacting the high concentrated recycle derived polymer reactant according to claim 6 to make said polymer.

8. A process of making a high concentrated recycle fiber, comprising making a high concentrated recycle derived polymer according to claim 7 and spinning said polymer into the fiber.

9. The process according to claim 1, wherein the second gasification process comprises:
a. charging an oxidant and the second feedstock to a gasification zone within the gasifier;
b. gasifying the second feedstock together with the oxidant in a gasification zone to produce a high concentrated recycle derived syngas composition; and
c. discharging at least a portion of the high concentrated recycle derived syngas composition from the gasifier;
wherein at least 90 wt. % of the high concentrated Recycle Polymer has a particle size in the largest dimension of not more than 2 mm.

10. The process according to claim 9, wherein at least one of the following conditions is present:
(i) gasification within the gasification zone is conducted at a temperature of at least 1000° C., or
(ii) the pressure within the gasification zone greater than 2.7 MPa, or
(iii) the feedstock composition comprises a slurry, or
(iv) the textiles and/or plastics are pre-ground to particles such that at least 90% of the particles have a particle size of less than 2 mm, or
(v) the tar yield is less than 4 wt. %, or
(vi) the gasifier contains no membrane wall in the gasification zone, or
(vii) a combination of two or more of the above conditions.

11. The process according to claim 1, wherein the gasification zone, and optionally all reaction zones, are operated at a temperature of more than 1000° C. and up to 2500° C., and at a pressure within the gasification zone (or combustion chamber) of at least 400 psig (2.76 MPa); wherein said second high concentrated recycle derived syngas stream contains less than 4 wt. % tar, based on the weight of all condensable solids in the high concentrated recycle derived syngas composition, or the amount of char generated by conversion of the carbon sources in the second feedstock composition is not more than 10 wt. %, based on the weight of the solids in the feedstock composition.

12. The process according to claim 1, wherein the high concentrated recycle derived material is a high concentrated recycle derived cellulose ester having at least one substituent on an anhydroglucose unit (AU) obtained, through one or more intermediate steps, from the second high concentrated recycle derived syngas.

13. The process according to claim 12, wherein the high concentrated recycle derived cellulose ester is chosen from a cellulose acetate, cellulose diacetate (CDA), cellulose triacetate (CTA), cellulose butyrate (CB), cellulose propionate (CP), cellulose acetate butyrate (CAB), cellulose acetate propionate (CAP), or combinations thereof.

14. The process according to claim 13, wherein the cellulose ester comprises substituents comprising acetyl and propionyl functional groups.

15. The process according to claim 13, wherein the cellulose ester comprises substituents comprising acetyl and butyryl functional groups.

16. The process according to claim 13, wherein the cellulose ester is cellulose di-acetate (CDA).

17. The process according to claim 1, wherein the second feedstock comprises coal; and wherein the second high concentrated recycle derived syngas stream has a compositional variability that is 5% or less measured over a time period that is the lesser of 12 days or the time period the second feedstock is fed to the gasifier, said high concentrated recycle derived syngas compositional variability satisfied against at least one of the following gaseous compounds (in moles):
  a. CO amount, or
  b. H2 amount, or
  c. CO2 amount, or
  d. CH4 amount, or
  e. H2S amount, or
  f. COS amount, or
  g. H2+CO amount, or its molar ratio in sequence (e.g. H2:CO ratio), or
  h. H2+CO+CO2 amount, or its molar ratio in sequence, or
  i. H2+CO+CH4 amount, or its molar ratio in sequence, or
  j. H2+CO+CO2+CH4 amount, or its molar ratio in sequence, or
  k. H2S+COS amount, or its molar ratio in sequence, or
  l. H2+CO+CO$_2$+CH4+H2S+COS.

18. The process according to claim 1, wherein the second feedstock is a slurry composition, the Recycle Polymer in the second feedstock composition has a particle size of not more than 2 mm, and the solid fossil fuel in the second feedstock composition has a particle size of less than 2 mm, the solids content in the slurry is at least 62 wt. %, the amount of Recycle Polymer present in the second feedstock slurry composition is 0.1 wt. % to less than 5 wt. % based on the weight of all solids, and water is present in an amount of at least 20 wt. % based on the weight of the feedstock slurry composition, and wherein either:
  a. the slurry is stable as determined by having an initial viscosity of 100,000 cP or less at 30 minutes using a Brookfield R/S Rheometer equipped with V80-40 vane operating at a shear rate of 1.83/s or a Brookfield viscometer with an LV-2 spindle rotating at a rate of 0.5 rpm, measured at ambient conditions; or
  b. the slurry is pumpable as determined by having a viscosity of less than 30,000 cP after mixing to obtain a homogeneous distribution of solids throughout the slurry and using a Brookfield R/S Rheometer equipped with V80-40 vane operating at a shear rate of 1.83/s or a Brookfield viscometer with an LV-2 spindle rotating at a rate of 0.5 rpm, measured at ambient conditions, or
  c. both.

19. An integrated process for preparing a high concentrated recycle derived cellulose ester comprising:
  a. making a first syngas in a gasifier in a first gasification process by gasifying a first feedstock that comprises solid fossil fuel;
  b. making a second high concentrated recycle derived syngas in said gasifier in a second gasification process by gasifying a second feedstock that comprises solid fossil fuel and Recycle Polymer;
  c. using at least a portion of the second high concentrated recycle derived syngas as a feedstock in a reaction scheme to produce at least one high concentrated recycle derived chemical intermediate;
  d. reacting said high concentrated recycle derived chemical intermediate in a reaction scheme to prepare at least one high concentrated recycle derived cellulose reactant as a raw material for preparing a high concentrated recycle derived cellulose ester, and/or selecting said high concentrated recycle derived chemical intermediate to be at least one high concentrated recycle derived cellulose reactant for preparing a high concentrated recycle derived cellulose ester; and
  e. reacting said at least one high concentrated recycle derived cellulose reactant to prepare said high concentrated recycle derived cellulose ester;
wherein said second feedstock contains Recycle Polymer in an amount that is higher than the amount of Recycle Polymer used, if any, in a first feedstock; and
wherein the amount of $CO_2$ generated in the second gasification process is no more than 20% greater than the amount of $CO_2$ generated in the first gasification process.

20. The process according to claim 19, wherein the high concentrated recycle derived cellulose reactant is produced by a reaction scheme that comprises one or more of the following reactions: (1) converting said high concentrated recycle derived syngas to methanol; (2) reacting said methanol to produce acetic acid; (3) reacting said methanol and/or said acetic acid to produce methyl acetate; and (4) reacting said methyl acetate and/or said methanol to produce acetic anhydride.

* * * * *